United States Patent
Low et al.

(10) Patent No.: US 12,343,403 B2
(45) Date of Patent: Jul. 1, 2025

(54) TARGETED LIGAND-PAYLOAD BASED DRUG DELIVERY FOR CELL THERAPY

(71) Applicant: Purdue Research Foundation, West Lafayette, IN (US)

(72) Inventors: Philip S. Low, West Lafayette, IN (US); Madduri Srinivasarao, West Lafayette, IN (US); Boning Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1566 days.

(21) Appl. No.: 16/486,632

(22) PCT Filed: Feb. 17, 2018

(86) PCT No.: PCT/US2018/018557
§ 371 (c)(1),
(2) Date: Aug. 16, 2019

(87) PCT Pub. No.: WO2018/152451
PCT Pub. Date: Aug. 23, 2018

(65) Prior Publication Data
US 2020/0054676 A1    Feb. 20, 2020

Related U.S. Application Data

(60) Provisional application No. 62/460,118, filed on Feb. 17, 2017.

(51) Int. Cl.
| | | |
|---|---|---|
| A61K 47/66 | (2017.01) | |
| A61K 40/10 | (2025.01) | |
| A61K 40/11 | (2025.01) | |
| A61K 40/31 | (2025.01) | |
| A61K 40/42 | (2025.01) | |
| A61K 47/69 | (2017.01) | |
| C07K 14/725 | (2006.01) | |
| C12N 9/90 | (2006.01) | |
| C12N 15/62 | (2006.01) | |
| A61K 38/00 | (2006.01) | |

(52) U.S. Cl.
CPC ............. *A61K 47/66* (2017.08); *A61K 40/10* (2025.01); *A61K 40/11* (2025.01); *A61K 40/31* (2025.01); *A61K 40/4211* (2025.01); *A61K 47/6901* (2017.08); *C07K 14/7051* (2013.01); *C12N 9/90* (2013.01); *C12N 15/62* (2013.01); *A61K 38/00* (2013.01); *A61K 2239/31* (2023.05); *A61K 2239/38* (2023.05); *A61K 2239/48* (2023.05); *C07K 2319/03* (2013.01); *C07K 2319/20* (2013.01); *C07K 2319/912* (2013.01); *C12Y 502/01008* (2013.01)

(58) Field of Classification Search
None
See application file for complete search history.

(56) References Cited

U.S. PATENT DOCUMENTS

| | | | |
|---|---|---|---|
| 11,034,752 B2 * | 6/2021 | Irvine ................. | C07K 14/7051 |
| 2003/0185840 A1 | 10/2003 | Ioannides et al. | |
| 2007/0077197 A1 | 4/2007 | Wedeking et al. | |
| 2008/0260812 A1 * | 10/2008 | Matsuyama ....... | C07K 16/3061 |
| | | | 435/177 |
| 2012/0076728 A1 | 3/2012 | Wu et al. | |
| 2019/0359697 A1 * | 11/2019 | Young .............. | C07K 14/70521 |
| 2019/0365806 A1 * | 12/2019 | Jeker ........................ | C12N 9/22 |

FOREIGN PATENT DOCUMENTS

| | | | |
|---|---|---|---|
| AU | 2018221171 | 1/2024 | |
| CA | 3053534 A1 | 8/2018 | |
| CN | 118634339 | 9/2024 | |
| EP | 3583218 A1 | 12/2019 | |
| EP | 3583218 A4 | 12/2020 | |
| JP | 2020508042 | 3/2020 | |
| JP | 7288402 B2 | 5/2023 | |
| KR | 102595249 B1 | 10/2023 | |
| WO | WO-9718307 A1 * | 5/1997 | ....... C07K 14/70575 |
| WO | WO-2011079227 A1 * | 6/2011 | ........... A61K 31/436 |
| WO | WO-2016/098078 A2 | 6/2016 | |
| WO | WO-2016/164745 A1 | 10/2016 | |
| WO | WO-2017123956 A1 * | 7/2017 | ............. A61K 35/12 |
| WO | WO-2018/152451 A1 | 8/2018 | |

OTHER PUBLICATIONS

Nam et al. Structural basis for the function and regulation of the receptor protein tyrosine phosphatase CD45(JEM, 2005, 201:441-452) (Year: 2005).*
Wilbowo et al. Structures of human folate receptors reveal biological trafficking states and diversity in folate and antifolate recognition (PNAS, 2013, 110:15180-15188) (Year: 2013).*
Suen, W. L. L.; Chau, Y. Size-Dependent Internalisation of Folate-Decorated Nanoparticles via the Pathways of Clathrin and Caveolae-Mediated Endocytosis in ARPE-19 Cells J. Pharm. Pharmacol. 2014, 66, 564-573 (Year: 2014).*
Zhang B, Napoleon JV, Liu X, et al. Sensitive manipulation of CAR T cell activity using a chimeric endocytosing receptor. Journal for Immuno Therapy of Cancer, 2020;8:e000756. (Year: 2020).*
Doucette et al., Point Mutations Alter the Cellular Distribution of the Human Folate Receptor in Cultured Chinese Hamster Ovary Cells. J. Nutr. 134: 308-316, 2004 (Year: 2004).*
"European Application Serial No. 18754879.7, Response filed May 25, 2021 to Extended European Search Report mailed Nov. 26, 2020", 11 pgs.
"European Application Serial No. 18754879.7, Response filed Aug. 16, 2022 to Communication Pursuant to Article 94(3) EPC mailed Jul. 18, 2022", 74 pgs.

(Continued)

*Primary Examiner* — Arthur S Leonard
(74) *Attorney, Agent, or Firm* — Schwegman Lundberg & Woessner, P.A.

(57) ABSTRACT

A drug delivery platform providing flexible fine tune of cell therapy is disclosed herein. Particularly, an engineered fusion protein is coupled with a high affinity ligand carrying at least one payload of drug to be internalized by the transplanted cell to observe or regulate transplanted cell therapy effects.

48 Claims, 26 Drawing Sheets
Specification includes a Sequence Listing.

(56) References Cited

OTHER PUBLICATIONS

"Japanese Application Serial No. 2019-544016, Final Notification of Reasons for Refusal mailed Oct. 25, 2022" (w/ English Translation), 10 pgs.
"Japanese Application Serial No. 2019-544016, Response filed Jun. 29, 2022 to Notification of Reasons for Refusal mailed Mar. 29, 2022", 11 pgs.
Shillingford, Jonathan M., et al., J. Am Soc Nephrol, vol. 23, No. 10, (2012), 1674-1681.
"Chinese Application Serial No. 201880024308.6, Voluntary Amendment filed May 15, 2020", (w/ English Translation of Claims), 5 pgs.
"European Application Serial No. 18754879.7, Extended European Search Report mailed Nov. 26, 2020", 8 pgs.
Xia, Wei, et al., "Folate-Targeted Therapies for Cancer", *Journal of Medicinal Chemistry*, 53(19), (Oct. 14, 2010), 6811-6824.
Zhou, Xiaoou, et al., "Improving the safety of T-Cell therapies using an inducible caspase-9 gene", *Experimental Hematology*, 44(11), (Jul. 26, 2016), 1013-1019.
"Japanese Application Serial No. 2019-544016, Notification of Reasons for Refusal mailed Mar. 29, 2022", (w/ English translation), 10 pgs.
"Improving the Safety of T Cell Therapies using an Inducible Caspase-9 Gene", Exp Hematol.,44 (11), (2016), 1013-1019.
"European Application Serial No. 18754879.7, Communication Pursuant to Article 94(3) EPC mailed Jul. 18, 2022", 4 pgs.
"European Application Serial No. 18754879.7, Response to Communication pursuant to Rules 161(2) and 162 EPC filed Apr. 17, 2020", 19 pgs.
"International Application Serial No. PCT/US2018/018557, International Preliminary Report on Patentability mailed Aug. 29, 2019", 9 pgs.
"International Application Serial No. PCT/US2018/018557, International Search Report mailed Jul. 2, 2018", 6 pgs.
"International Application Serial No. PCT/US2018/018557, Written Opinion mailed Jul. 2, 2018", 7 pgs.
Di Stasi, Antonio, et al., "Inducible Apoptosis as a Safety Switch for Adoptive Cell Therapy", *The New England Journal of Medicine*, 365, (2011), 1673-1683.
James, John R., et al., "Biophysical mechanism of T-cell receptor triggering in a reconstituted system", HHMI Author Manuscript, published as: Nature, vol. 487, No. 7405, 65-69, (Jul. 5, 2012), 18 pgs.
Shillingford, Jonathan M., et al., "Folate-Conjugated Rapamycin Slows Progression of Polycystic Kidney Disease", *J. Am Soc Nephrol*, vol. 23, No. 10, (Sep. 28, 2012).
Sun, Jie, et al., "The quest for spatio-temporal control of CAR T cells", *Cell Research*, 25, (2015), 1281-1282.
"Australian Application Serial No. 2018221171, First Examination Report mailed Oct. 31, 2023", 5 pgs.
"Canadian Application Serial No. 3,053,534, Office Action mailed Jun. 20, 2023", 6 pgs.
"Canadian Application Serial No. 3,053,534, Response filed Oct. 20, 2023 to Office Action mailed Jun. 20, 2023", w/ current English claims, 25 pgs.
"Chinese Application Serial No. 201880024308.6, Office Action mailed Jan. 20, 2023", w/ English Translation, 14 pgs.
"Chinese Application Serial No. 201880024308.6, Office Action mailed Jul. 27, 2023", w/ English Claims, 8 pgs.
"Chinese Application Serial No. 201880024308.6, Response filed May 12, 2023 to Office Action mailed Jan. 20, 2023", w/ English claims, 17 pgs.
"Chinese Application Serial No. 201880024308.6, Response filed Oct. 7, 2023 to Office Action mailed Jul. 27, 2023", w/ English claims, 13 pgs.
"Japanese Application Serial No. 2019-544016, Final Notification of Reasons for Refusal mailed Apr. 4, 2023", w/ English Translation, 5 pgs.
"Japanese Application Serial No. 2019-544016, Office Action mailed Mar. 14, 2023", 3 pgs.
"Japanese Application Serial No. 2019-544016, Response filed Mar. 22, 2023 to Final Notification of Reasons for Refusal mailed Oct. 25, 2022", w/ English claims, 8 pgs.
"Japanese Application Serial No. 2019-544016, Response Filed Apr. 4, 2023 to Final Notification of Reasons for Refusal mailed Apr. 4, 2023", w/ English claims, 7 pgs.
"Japanese Application Serial No. 2023-047827, Voluntary Amendment filed May 25, 2023", w/ English claims, 11 pgs.
"Japanese Application Serial No. 2023-047827, Voluntary Amendment filed Jul. 10, 2023", w/ English claims, 16 pgs.
"Korean Application Serial No. 10-2019-7026818, Notice of Preliminary Rejection mailed Jul. 24, 2023", w/ English translation, 13 pgs.
"Korean Application Serial No. 10-2019-7026818, Response filed Sep. 13, 2023 to Notice of Preliminary Rejection mailed Jul. 24, 2023", w/ English claims, 42 pgs.
"New Zealand Application Serial No. 756957, Voluntary Amendment filed Feb. 9, 2023", 22 pgs.
"New Zealand Application Serial No. 797259, Voluntary Amendment filed Feb. 23, 2023", 27 pgs.
Porter, D.L., et al., "Chimeric antigen receptor-modified T cells in chronic lymphoid leukemia", The New England Journal of Medicine 365:725-33. 2011., (Aug. 25, 2011), 9 pgs.
"Australian Application Serial No. 2018221171, Response filed Dec. 22, 2023 to First Examination Report mailed Oct. 31, 2023", 33 pgs.
"Chinese Application Serial No. 201880024308.6, Decision of Rejection mailed Jan. 4, 2024", w English Claims, 16 pgs.
"Indian Application Serial No. 201917036615, First Examination Report mailed Feb. 16, 2024", 8 pgs.
"Japanese Application Serial No. 2023-047827, Notification of Reasons for Rejection mailed Apr. 2, 2024", W English Translation, 12 pgs.
"Japanese Application Serial No. 2023-047827, Response filed Aug. 9, 2024 to Notification of Reasons for Rejection mailed Apr. 2, 2024", W English Claims, 14 pgs.
"Chinese Application Serial No. 202410423409.8, Notification to Make Rectification (210302) mailed Jul. 31, 2024", w Machine English translation, 3 pgs.
"Indian Application Serial No. 201917036615, Response filed Aug. 2, 2024 to First Examination Report mailed Feb. 16, 2024", w English claims, 58 pgs.
"Japanese Application Serial No. 2023-047827, Final Notification of Reasons for Rejection mailed Nov. 26, 2024", W English Translation, 10 pgs.
"Chinese Application Serial No. 202410423409.8, Office Action mailed Nov. 27, 2024", w English Claims, 8 pgs.

* cited by examiner

| Module 1: GPI anchored protein | | Module 2 | |
|---|---|---|---|
| Protein | Ligand | Protein | Ligand |
| FRa |  FA derivitives | FKBP |  FK506 derivitives <br><br> SLF derivitives |
| FRb | | DHFR |  MTX derivitives |
| uPAR |  | scFv against FITC |  FITC derivitives |
| | | scFV against DNP |  DNP-Ser |

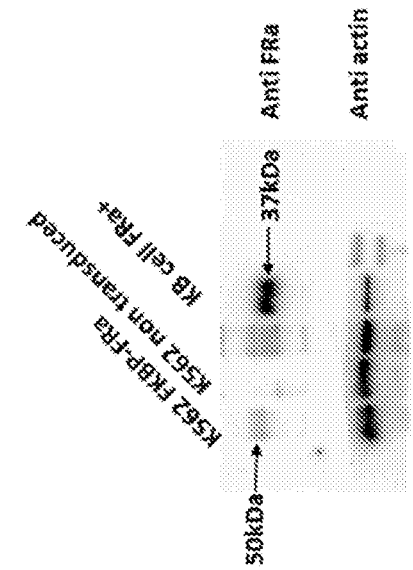
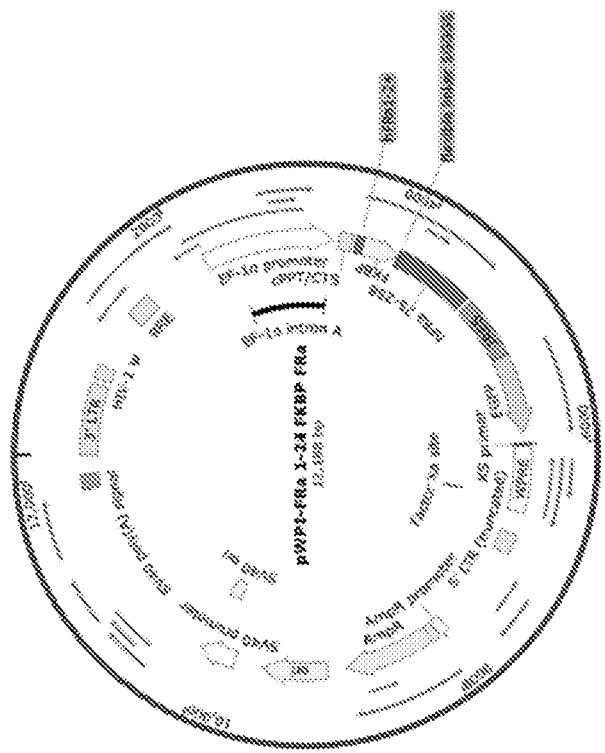
FIG. 4B
FIG. 4A

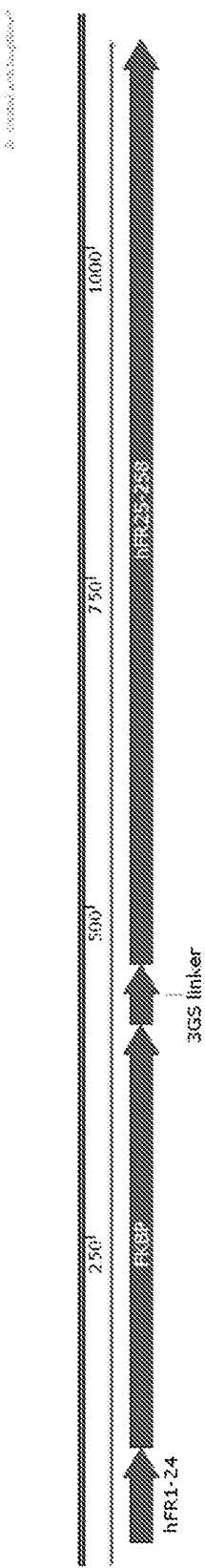
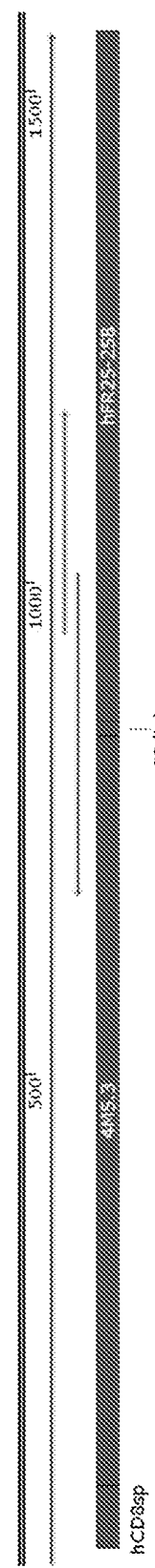
FIG. 4D
FIG. 4E

SEQUENCE LISTING

```
<160> NUMBER OF SEQ ID NOS: 22

<210> SEQ ID NO 1
<211> LENGTH: 367
<212> TYPE: PRT
<213> ORGANISM: Artificial Sequence
<220> FEATURE:
<223> OTHER INFORMATION: A synthetic amino acid sequence for mouse FKBP-
      FRa with linker peptide

<400> SEQUENCE: 1
```

```
Met Ala His Leu Met Thr Val Gln Leu Leu Leu Val Met Trp Met
1               5                   10                  15

Ala Glu Cys Ala Gln Ser Arg Ala Gly Val Gln Val Glu Thr Ile Ser
                20                  25                  30

Pro Gly Asp Gly Arg Thr Phe Pro Lys Arg Gly Gln Thr Cys Val Val
            35                  40                  45

His Tyr Thr Gly Met Leu Glu Asp Gly Lys Lys Phe Asp Ser Ser Arg
50                  55                  60

Asp Arg Asn Lys Pro Phe Lys Phe Thr Leu Gly Lys Gln Glu Val Ile
65                  70                  75                  80

Arg Gly Trp Glu Glu Gly Val Ala Gln Met Ser Val Gly Gln Arg Ala
                85                  90                  95

Lys Leu Ile Ile Ser Ser Asp Tyr Ala Tyr Gly Ala Thr Gly His Pro
                100                 105                 110

Gly Ile Ile Pro Pro His Ala Thr Leu Val Phe Asp Val Glu Leu Leu
            115                 120                 125

Lys Leu Glu Ser Gly Gly Gly Ser Thr Arg Ala Arg Thr Glu Leu Leu
130                 135                 140

Asn Val Cys Met Asp Ala Lys His His Lys Glu Lys Pro Gly Pro Glu
145                 150                 155                 160

Asp Asn Leu His Asp Gln Cys Ser Pro Trp Lys Thr Asn Ser Cys Cys
                165                 170                 175

Ser Thr Asn Thr Ser Gln Glu Ala His Lys Asp Ile Ser Tyr Leu Tyr
            180                 185                 190

Arg Phe Asn Trp Asn His Cys Gly Thr Met Thr Ser Glu Cys Lys Arg
                195                 200                 205

His Phe Ile Gln Asp Thr Cys Leu Tyr Glu Cys Ser Pro Asn Leu Gly
210                 215                 220

Pro Trp Ile Gln Gln Val Asp Gln Ser Trp Arg Lys Glu Arg Ile Leu
225                 230                 235                 240

Asp Val Pro Leu Cys Lys Glu Asp Cys Gln Gln Trp Trp Glu Asp Cys
                245                 250                 255

Gln Ser Ser Phe Thr Cys Lys Ser Asn Trp His Lys Gly Trp Asn Trp
            260                 265                 270

Ser Ser Gly His Asn Glu Cys Pro Val Gly Ala Ser Cys His Pro Phe
        275                 280                 285

Thr Phe Tyr Phe Pro Thr Ser Ala Ala Leu Cys Glu Glu Ile Trp Ser
            290                 295                 300

His Ser Tyr Lys Leu Ser Asn Tyr Ser Arg Gly Ser Gly Arg Cys Ile
305                 310                 315                 320

Gln Met Trp Phe Asp Pro Ala Gln Gly Asn Pro Asn Glu Glu Val Ala
                325                 330                 335

Arg Phe Tyr Ala Glu Ala Met Ser Gly Ala Gly Phe His Gly Thr Trp
            340                 345                 350

Pro Leu Leu Cys Ser Leu Ser Leu Val Leu Leu Trp Val Ile Ser
                355                 360                 365

<210> SEQ ID NO 2
<211> LENGTH: 369
<212> TYPE: PRT
<213> ORGANISM: Artificial Sequence
<220> FEATURE:
<223> OTHER INFORMATION: A synthetic amino acid sequence for human FKBP-
      FRa with linker peptide
```

<400> SEQUENCE: 2

```
Met Ala Gln Arg Met Thr Thr Gln Leu Leu Leu Leu Val Trp Val
1               5                   10                  15

Ala Val Val Gly Glu Ala Gln Thr Gly Val Gln Val Glu Thr Ile Ser
            20                  25                  30

Pro Gly Asp Gly Arg Thr Phe Pro Lys Arg Gly Gln Thr Cys Val Val
        35                  40                  45

His Tyr Thr Gly Met Leu Glu Asp Gly Lys Lys Phe Asp Ser Ser Arg
    50                  55                  60

Asp Arg Asn Lys Pro Phe Lys Phe Met Leu Gly Lys Gln Glu Val Ile
65                  70                  75                  80

Arg Gly Trp Glu Glu Gly Val Ala Gln Met Ser Val Gly Gln Arg Ala
                85                  90                  95

Lys Leu Thr Ile Ser Pro Asp Tyr Ala Tyr Gly Ala Thr Gly His Pro
            100                 105                 110

Gly Ile Ile Pro Pro His Ala Thr Leu Val Phe Asp Val Glu Leu Leu
        115                 120                 125

Lys Leu Glu Ser Gly Gly Gly Ser Arg Ile Ala Trp Ala Arg Thr Glu
    130                 135                 140

Leu Leu Asn Val Cys Met Asn Ala Lys His His Lys Glu Lys Pro Gly
145                 150                 155                 160

Pro Glu Asp Lys Leu His Glu Gln Cys Arg Pro Trp Arg Lys Asn Ala
                165                 170                 175

Cys Cys Ser Thr Asn Thr Ser Gln Glu Ala His Lys Asp Val Ser Tyr
            180                 185                 190

Leu Tyr Arg Phe Asn Trp Asn His Cys Gly Glu Met Ala Pro Ala Cys
        195                 200                 205

Lys Arg His Phe Ile Gln Asp Thr Cys Leu Tyr Glu Cys Ser Pro Asn
    210                 215                 220

Leu Gly Pro Trp Ile Gln Gln Val Asp Gln Ser Trp Arg Lys Glu Arg
225                 230                 235                 240

Val Leu Asn Val Pro Leu Cys Lys Glu Asp Cys Glu Gln Trp Trp Glu
                245                 250                 255

Asp Cys Arg Thr Ser Tyr Thr Cys Lys Ser Asn Trp His Lys Gly Trp
            260                 265                 270

Asn Trp Thr Ser Gly Phe Asn Lys Cys Ala Val Gly Ala Ala Cys Gln
        275                 280                 285

Pro Phe His Phe Tyr Phe Pro Thr Pro Thr Val Leu Cys Asn Glu Ile
    290                 295                 300

Trp Thr His Ser Tyr Lys Val Ser Asn Tyr Ser Arg Gly Ser Gly Arg
305                 310                 315                 320

Cys Ile Gln Met Trp Phe Asp Pro Ala Gln Gly Asn Pro Asn Glu Glu
                325                 330                 335

Val Ala Arg Phe Tyr Ala Ala Ala Met Ser Gly Ala Gly Pro Trp Ala
            340                 345                 350

Ala Trp Pro Phe Leu Leu Ser Leu Ala Leu Met Leu Leu Trp Leu Leu
        355                 360                 365

Ser
```

<210> SEQ ID NO 3
<211> LENGTH: 485
<212> TYPE: PRT
<213> ORGANISM: Artificial Sequence
<220> FEATURE:

<223> OTHER INFORMATION: A synthetic amino acid sequence for mouse antiCD19 CAR T construct

<400> SEQUENCE: 3

```
Met Gly Val Pro Thr Gln Leu Leu Gly Leu Leu Leu Trp Ile Thr
1               5                   10                  15

Asp Ala Ile Cys Glu Gln Lys Leu Ile Ser Glu Glu Asp Leu Asp Ile
            20                  25                  30

Gln Met Thr Gln Ser Pro Ala Ser Leu Ser Thr Ser Leu Gly Glu Thr
        35                  40                  45

Val Thr Ile Gln Cys Gln Ala Ser Glu Asp Ile Tyr Ser Gly Leu Ala
    50                  55                  60

Trp Tyr Gln Gln Lys Pro Gly Lys Ser Pro Gln Leu Leu Ile Tyr Gly
65              70                  75                  80

Ala Ser Asp Leu Gln Asp Gly Val Pro Ser Arg Phe Ser Gly Ser Gly
                85                  90                  95

Ser Gly Thr Gln Tyr Ser Leu Lys Ile Thr Ser Met Gln Thr Glu Asp
            100                 105                 110

Glu Gly Val Tyr Phe Cys Gln Gln Gly Leu Thr Tyr Pro Arg Thr Phe
        115                 120                 125

Gly Gly Gly Thr Lys Leu Glu Leu Lys Gly Gly Gly Ser Gly Gly
    130                 135                 140

Gly Gly Ser Gly Gly Gly Ser Glu Val Gln Leu Gln Gln Ser Gly
145                 150                 155                 160

Ala Glu Leu Val Arg Pro Gly Thr Ser Val Lys Leu Ser Cys Lys Val
                165                 170                 175

Ser Gly Asp Thr Ile Thr Phe Tyr Tyr Met His Phe Val Lys Gln Arg
            180                 185                 190

Pro Gly Gln Gly Leu Glu Trp Ile Gly Arg Ile Asp Pro Glu Asp Glu
        195                 200                 205

Ser Thr Lys Tyr Ser Glu Lys Phe Lys Asn Lys Ala Thr Leu Thr Ala
    210                 215                 220

Asp Thr Ser Ser Asn Thr Ala Tyr Leu Lys Leu Ser Ser Leu Thr Ser
225                 230                 235                 240

Glu Asp Thr Ala Thr Tyr Phe Cys Ile Tyr Gly Gly Tyr Tyr Phe Asp
                245                 250                 255

Tyr Trp Gly Gln Gly Val Met Val Thr Val Ser Ser Ile Glu Phe Met
            260                 265                 270

Tyr Pro Pro Pro Tyr Leu Asp Asn Glu Arg Ser Asn Gly Thr Ile Ile
        275                 280                 285

His Ile Lys Glu Lys His Leu Cys His Thr Gln Ser Ser Pro Lys Leu
    290                 295                 300

Phe Trp Ala Leu Val Val Val Ala Gly Val Leu Phe Cys Tyr Gly Leu
305                 310                 315                 320

Leu Val Thr Val Ala Leu Cys Val Ile Trp Thr Asn Ser Arg Arg Asn
                325                 330                 335

Arg Gly Gly Gln Ser Asp Tyr Met Asn Met Thr Pro Arg Arg Pro Gly
            340                 345                 350

Leu Thr Arg Lys Pro Tyr Gln Pro Tyr Ala Pro Ala Arg Asp Phe Ala
        355                 360                 365

Ala Tyr Arg Pro Arg Ala Lys Phe Ser Arg Ser Ala Glu Thr Ala Ala
    370                 375                 380

Asn Leu Gln Asp Pro Asn Gln Leu Tyr Asn Glu Leu Asn Leu Gly Arg
385                 390                 395                 400
```

-continued

```
Arg Glu Glu Tyr Asp Val Leu Glu Lys Lys Arg Ala Arg Asp Pro Glu
            405                 410                 415

Met Gly Gly Lys Gln Gln Arg Arg Asn Pro Gln Glu Gly Val Tyr
        420                 425                 430

Asn Ala Leu Gln Lys Asp Lys Met Ala Glu Ala Tyr Ser Glu Ile Gly
            435                 440                 445

Thr Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Thr Leu Ala Pro Arg
            485

<210> SEQ ID NO 4
<211> LENGTH: 496
<212> TYPE: PRT
<213> ORGANISM: Artificial Sequence
<220> FEATURE:
<223> OTHER INFORMATION: A synthetic amino acid sequence for human
      antiCD19 CAR T construct

<400> SEQUENCE: 4

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
            85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
            165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
            245                 250                 255

Ser Tyr Ala Met Asp Tyr Trp Gly Gln Gly Thr Ser Val Thr Val Ser
```

```
            260                 265                 270
Ser Ala Ala Ile Glu Val Met Tyr Pro Pro Tyr Leu Asp Asn
            275                 280             285

Glu Lys Ser Asn Gly Thr Ile Ile His Val Lys Gly Lys His Leu Cys
        290                 295             300

Pro Ser Pro Leu Phe Pro Gly Pro Ser Lys Pro Phe Trp Val Leu Val
305                 310              315                 320

Val Val Gly Gly Val Leu Ala Cys Tyr Ser Leu Leu Val Thr Val Ala
                325                 330              335

Phe Ile Ile Phe Trp Val Arg Ser Lys Arg Ser Arg Leu Leu His Ser
            340                 345             350

Asp Tyr Met Asn Met Thr Pro Arg Arg Pro Gly Pro Thr Arg Lys His
        355                 360             365

Tyr Gln Pro Tyr Ala Pro Pro Arg Asp Phe Ala Ala Tyr Arg Ser Arg
    370                 375             380

Val Lys Phe Ser Arg Ser Ala Asp Ala Pro Ala Tyr Gln Gln Gly Gln
385                 390             395                 400

Asn Gln Leu Tyr Asn Glu Leu Asn Leu Gly Arg Arg Glu Glu Tyr Asp
                405                 410              415

Val Leu Asp Lys Arg Arg Gly Arg Asp Pro Glu Met Gly Gly Lys Pro
            420                 425             430

Gln Arg Arg Lys Asn Pro Gln Glu Gly Leu Tyr Asn Glu Leu Gln Lys
        435                 440             445

Asp Lys Met Ala Glu Ala Tyr Ser Glu Ile Gly Met Lys Gly Glu Arg
    450                 455             460

Arg Arg Gly Lys Gly His Asp Gly Leu Tyr Gln Gly Leu Ser Thr Ala
465                 470             475                 480

Thr Lys Asp Thr Tyr Asp Ala Leu His Met Gln Ala Leu Pro Pro Arg
                485                 490             495

<210> SEQ ID NO 5
<211> LENGTH: 12182
<212> TYPE: DNA
<213> ORGANISM: Artificial Sequence
<220> FEATURE:
<223> OTHER INFORMATION: A synthetic vector sequence for pWPI for human
      T cell transduction

<400> SEQUENCE: 5
ttggaagggc taattcactc ccaaagaaga caagatatcc ttgatctgtg gatctaccac     60
acacaaggct acttccctga ttagcagaac tacacaccag ggccaggggt cagatatcca    120
ctgacctttg gatggtgcta caagctagta ccagttgagc cagataaggt agaagaggcc    180
aataaaggag agaacaccag cttgttacac cctgtgagcc tgcatgggat ggatgacccg    240
gagagagaag tgttagagtg gaggtttgac agccgcctag catttcatca cgtggcccga    300
gagctgcatc cggagtactt caagaactgc tgatatcgag cttgctacaa gggactttcc    360 gctgggggact ttccagggag gcgtggcctg ggcgggactg gggagtggcg agccctcaga    420
tcctgcatat aagcagctgc ttttgcctg tactgggtct ctctggttag accagatctg    480
agcctgggag ctctctggct aactagggaa cccactgctt aagcctcaat aaagcttgcc    540
ttgagtgctt caagtagtgt gtgcccgtct gttgtgtgac tctggtaact agagatccct    600
cagacccttt tagtcagtgt ggaaaatctc tagcagtggc gcccgaacag ggacttgaaa    660
gcgaaaggga accagagga gctctctcga cgcaggactc ggcttgctga agcgcgcacg    720
```

```
gcaagaggcg aggggcggcg actggtgagt acgccaaaaa ttttgactag cggaggctag    780
aaggagagag atgggtgcga gagcgtcagt attaagcggg ggagaattag atcgcgatgg    840
gaaaaaattc ggttaaggcc aggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg ctgatcttca gacctggagg aggagatatg agggacaatt ggagaagtga   1200
attatataaa tataaagtag taaaaattga accattagga gtagcaccca ccaaggcaaa   1260
gagaagagtg gtgcagagag aaaaaagagc agtgggaata ggagctttgt tccttgggtt   1320
cttgggagca gcaggaagca ctatgggcgc agcgtcaatg acgctgacgg tacaggccag   1380
acaattattg tctggtatag tgcagcagca gaacaatttg ctgagggcta ttgaggcgca   1440
acagcatctg ttgcaactca cagtctgggg catcaagcag ctccaggcaa gaatcctggc   1500
tgtggaaaga tacctaaagg atcaacagct cctggggatt tggggttgct ctggaaaact   1560
catttgcacc actgctgtgc cttggaatgc tagttggagt aataaatctc tggaacagat   1620
ttggaatcac acgacctgga tggagtggga cagagaaatt aacaattaca caagcttaat   1680
acactcctta attgaagaat cgcaaaacca gcaagaaaag aatgaacaag aattattgga   1740
attagataaa tgggcaagtt tgtggaattg gtttaacata acaaattggc tgtggtatat   1800
aaaattattc ataatgatag taggaggctt ggtaggttta agaatagttt ttgctgtact   1860
ttctatagtg aatagagtta ggcagggata ttcaccatta tcgtttcaga cccacctccc   1920
aaccccgagg ggacccgaca ggcccgaagg aatagaagaa gaaggtggag agagagacag   1980
agacagatcc attcgattag tgaacggatc tcgacggtat cgatgtcgac gataagcttt   2040
gcaaagatgt ataagttttt aaacagagag gaatctttgc agctaatgga ccttctaggt   2100
cttgaaagga gtgggaattg gctccggtgc ccgtcagtgg gcagagcgca catcgcccac   2160
agtccccgag aagttggggg gaggggtcgg caattgaacc ggtgcctaga gaaggtggcg   2220
cggggtaaac tgggaaagtg atgtcgtgta ctggctccgc cttttttccg agggtgggggg   2280 agaaccgtat ataagtgcag tagtcgccgt gaacgttctt tttcgcaacg ggttgccgc   2340 cagaacacag gtaagtgccg tgtgtggttc ccgcgggcct ggcctcttta cgggttatgg   2400
cccttgcgtg ccttgaatta cttccactgg ctgcagtacg tgattcttga tcccgagctt   2460
cgggttggaa gtgggtggga gagttcgagg ccttgcgctt aaggagcccc ttcgcctcgt   2520
gcttgagttg aggcctggcc tgggcgctgg ggccgccgcg tgcgaatctg gtggcacctt   2580
cgcgcctgtc tcgctgcttt cgataagtct ctagccattt aaaattttg atgacctgct   2640 gcgacgcttt ttttctggca agatagtctt gtaaatgcgg gccaagatct gcacactggt   2700
atttcggttt ttggggccgc gggcggcgac ggggcccgtg cgtcccagcg cacatgttcg   2760
gcgaggcggg gcctgcgagc gcggccaccg agaatcggac gggggtagtc tcaagctggc   2820
cggcctgctc tggtgcctgg cctcgcgccg ccgtgtatcg ccccgccctg gcggcaagg   2880 ctggcccggt cggcaccagt tgcgtgagcg gaaagatggc cgcttcccgg ccctgctgca   2940
gggagctcaa aatggaggac gcggcgctcg ggagagcggg cgggtgagtc acccacacaa   3000
aggaaaaggg cctttccgtc ctcagccgtc gcttcatgtg actccacgga gtaccggcg   3060 ccgtccaggc acctcgatta gttctcgagc ttttggagta cgtcgtcttt aggttggggg   3120
```

```
gagggtttt atgcgatgga gtttccccac actgagtggg tggagactga agttaggcca      3180
gcttggcact tgatgtaatt ctccttggaa tttgcccttt ttgagtttgg atcttggttc      3240
attctcaagc ctcagacagt ggttcaaagt ttttttcttc catttcaggt gtcgtgagga      3300
atttcgacat ttaaatttaa ttaatctcga cggtatcggt taacttttaa aagaaaaggg      3360
gggattgggg ggtacagtgc agggaaaga atagtagaca taatagcaac agacatacaa      3420
actaaagaat tacaaaaaca aattacaaaa attcaaaatt ttatcgatca cgagactagc      3480
ctcgaggttt atggctcacc tgatgactgt gcagttgttg ctcctggtga tgtggatggc      3540
cgaatgtgct cagtccagag ctggagtgca ggtggagacc atctctcctg gagacgggcg      3600
caccttccca aagcgcggcc agacctgcgt ggtgcactac acgggatgc ttgaagatgg       3660 aaagaaattt gattcctctc gggacagaaa caagcctttt aagtttacac taggcaagca      3720
ggaggtgatc cgaggctggg aggaaggggt agcccagatg agtgtgggtc agagagccaa      3780
actgataatc tcctcagact atgcctatgg agccaccggg cacccaggca tcatcccacc      3840
acatgccact cttgttttg atgtggagct tctaaaactg gaaagcggcg gcggcagcac       3900
tcgggccagg actgaacttc tcaatgtctg catggatgcc aaacaccaca agaaaaaacc      3960
gggccctgag gacaatttac acgaccagtg cagcccctgg aagacgaatt cctgctgttc      4020
cacgaacaca agccaggaag cacataagga catttcctac ctgtaccggt tcaactggaa      4080
ccactgcgga actatgacat cggaatgcaa acggcacttt atccaagaca cctgcctcta      4140
tgagtgttcc ccgaacttgg gaccctggat ccagcaggtg gaccagagct ggcgcaaaga      4200
gcggatcctt gatgttcccc tgtgcaaaga ggactgtcag cagtggtggg aggactgcca      4260
gagctctttt acctgcaaga gcaattggca caagggatgg aactggtcct cggggcataa      4320
cgagtgtcct gtgggagcct cctgccatcc cttcaccttc tacttcccca catctgctgc      4380
tctgtgtgag gaaatctgga gtcactccta caagctcagc aactacagtc gagggagcgg      4440
ccgctgcatt cagatgtggt tcgacccagc ccagggcaac cccaacgagg aagtggcgag      4500
```

```
gttctatgcc gaggccatga gtggagctgg gtttcatggg acctggccac tcttgtgcag    4560
cctgtcctta gtgctgctct gggtgatcag ctgaaaacta cgggctgcag gaattccgcc    4620 ccccccccc  taacgttact ggccgaagcc gcttggaata aggccggtgt gcgtttgtct    4680
atatgttatt ttccaccata ttgccgtctt ttggcaatgt gagggcccgg aaacctggcc    4740
ctgtcttctt gacgagcatt cctagggtc  tttcccctct cgccaaagga atgcaaggtc    4800
tgttgaatgt cgtgaaggaa gcagttcctc tggaagcttc ttgaagacaa caacgtctg     4860 tagcgaccct ttgcaggcag cggaaccccc cacctggcga caggtgcctc tgcggccaaa    4920
agccacgtgt ataagataca cctgcaaagg cggcacaacc ccagtgccac gttgtgagtt    4980
ggatagttgt ggaaagagtc aaatggctct cctcaagcgt attcaacaag gggctgaagg    5040
atgcccagaa ggtaccccat tgtatggat  ctgatctggg gcctcggtgc acatgcttta    5100
catgtgttta gtcgaggtta aaaaacgtct aggcccccg  aaccacgggg acgtggtttt    5160
cctttgaaaa acacgatgat aataccatgg tgagcaaggg cgaggagctg ttcaccgggg    5220
tggtgcccat cctggtcgag ctggacggcg acgtaaacgg ccacaagttc agcgtgtccg    5280
gcgagggcga gggcgatgcc acctacggca agctgaccct gaagttcatc tgcaccaccg    5340
gcaagctgcc cgtgccctgg cccaccctcg tgaccaccct gacctacggc gtgcagtgct    5400
tcagccgcta ccccgaccac atgaagcagc acgacttctt caagtccgcc atgcccgaag    5460
gctacgtcca ggagcgcacc atcttcttca aggacgacgg caactacaag acccgcgccg    5520
aggtgaagtt cgagggcgac accctggtga accgcatcga gctgaagggc atcgacttca    5580
aggaggacgg caacatcctg ggcacaagc  tggagtacaa ctacaacagc cacaacgtct    5640
atatcatggc cgacaagcag aagaacggca tcaaggtgaa cttcaagatc cgccacaaca    5700
tcgaggacgg cagcgtgcag ctcgccgacc actaccagca gaacacccccc atcggcgacg    5760 gccccgtgct gctgcccgac aaccactacc tgagcaccca gtccgccctg agcaaagacc    5820
ccaacgagaa gcgcgatcac atggtcctgc tggagttcgt gaccgccgcc gggatcactc    5880
tcggcatgga cgagctgtac aagtccggac tcagatctcg actagctagt agctagctag    5940
ctagtcgagc tcaagcttcg aattcgatat caagcttatc gcgataccgt cgacctcgag    6000
ggaattccga taatcaacct ctggattaca aaatttgtga agattgact  ggtattctta    6060 actatgttgc tccttttacg ctatgtggat acgctgcttt aatgcctttg tatcatgcta    6120
ttgcttcccg tatggctttc attttctcct ccttgtataa atcctggttg ctgtctcttt    6180
atgaggagtt gtggcccgtt gtcaggcaac gtggcgtggt gtgcactgtg tttgctgacg    6240
caacccccac tggttgggc  attgccacca cctgtcagct cctttccggg actttcgctt    6300
tccccctccc tattgccacg gcggaactca tcgccgcctg ccttgcccgc tgctggacag    6360
gggctcggct gttgggcact gacaattccg tggtgttgtc ggggaagctg acgtcctttc    6420
catgctgctg cgcctgtgtt gccacctgga ttctgcgcgg gacgtccttc tgctacgtcc    6480
cttcggccct caatccagcg gaccttcctt cccgcggcct gctgccggct ctgcggcctc    6540
ttccgcgtct tcgccttcgc cctcagacga gtcggatctc cctttgggcc gcctccccgc    6600
atcgggaatt cgagctcggt acctttaaga ccaatgactt acaaggcagc tgtagatctt    6660
agccactttt taaaagaaaa ggggggactg aagggctaa  ttcactccca acgaagacaa    6720
gatgggatca attcaccatg gaataacttc gtatagcat  acattatacg aagttatgct    6780 gcttttgct  tgtactgggt ctctctggtt agaccagatc tgagcctggg agctctctgg    6840
```

```
ctaactaggg aacccactgc ttaagcctca ataaagcttg ccttgagtgc ttcaagtagt    6900
gtgtgcccgt ctgttgtgtg actctggtaa ctagagatcc ctcagaccct tttagtcagt    6960
gtggaaaatc tctagcagca tctagaatta attccgtgta ttctatagtg tcacctaaat    7020
cgtatgtgta tgatacataa ggttatgtat taattgtagc cgcgttctaa cgacaatatg    7080
tacaagccta attgtgtagc atctggctta ctgaagcaga ccctatcatc tctctcgtaa    7140
actgccgtca gagtcggttt ggttggacga accttctgag tttctggtaa cgccgtcccg    7200
cacccggaaa tggtcagcga accaatcagc agggtcatcg ctagccagat cctctacgcc    7260
ggacgcatcg tggccggcat caccggcgcc acaggtgcgg ttgctggcgc ctatatcgcc    7320
gacatcaccg atggggaaga tcgggctcgc cacttcgggc tcatgagcgc ttgtttcggc    7380
gtgggtatgg tggcaggccc cgtggccggg ggactgttgg gcgccatctc cttgcatgca    7440
ccattccttg cggcggcggt gctcaacggc ctcaacctac tactgggctg cttcctaatg    7500
caggagtcgc ataagggaga gcgtcgaatg gtgcactctc agtacaatct gctctgatgc    7560
cgcatagtta agccagcccc gacacccgcc aacacccgct gacgcgccct gacgggcttg    7620
tctgctcccg gcatccgctt acagacaagc tgtgaccgtc tccgggagct gcatgtgtca    7680
gaggttttca ccgtcatcac cgaaacgcgc gagacgaaag gcctcgtga tacgcctatt    7740 tttataggtt aatgtcatga taataatggt ttcttagacg tcaggtggca cttttcgggg    7800
aaatgtgcgc ggaacccta tttgttatt tttctaaata cattcaaata tgtatccgct    7860
catgagacaa taaccctgat aaatgcttca ataatattga aaaggaaga gtatgagtat    7920 tcaacatttc cgtgtcgccc ttattccctt ttttgcggca ttttgccttc ctgtttttgc    7980
tcacccagaa acgctggtga agtaaaaga tgctgaagat cagttgggtg cacgagtggg    8040
ttacatcgaa ctggatctca acagcggtaa gatccttgag agttttcgcc ccgaagaacg    8100
ttttccaatg atgagcactt ttaaagttct gctatgtggc gcggtattat cccgtattga    8160
cgccgggcaa gagcaactcg gtcgccgcat acactattct cagaatgact tggttgagta    8220
ctcaccagtc acagaaaagc atcttacgga tggcatgaca gtaagagaat tatgcagtgc    8280
tgccataacc atgagtgata acactgcggc caacttactt ctgacaacga tcggaggacc    8340
gaaggagcta accgcttttt tgcacaacat gggggatcat gtaactcgcc ttgatcgttg    8400
ggaaccggag ctgaatgaag ccataccaaa cgacgagcgt gacaccacga tgcctgtagc    8460
aatggcaaca acgttgcgca aactattaac tggcgaacta cttactctag cttcccggca    8520
acaattaata gactggatgg aggcggataa agttgcagga ccacttctgc gctcggccct    8580
tccggctggc tggtttattg ctgataaatc tggagccggt gagcgtgggt ctcgcggtat    8640
cattgcagca ctggggccag atggtaagcc ctcccgtatc gtagttatct acacgacggg    8700
gagtcaggca actatggatg aacgaaatag acagatcgct gagataggtg cctcactgat    8760
taagcattgg taactgtcag accaagttta ctcatatata ctttagattg atttaaaact    8820 tcattttta tttaaaagga tctaggtgaa gatccttttt gataatctca tgaccaaaat    8880
cccttaacgt gagttttcgt tccactgagc gtcagacccc gtagaaaaga tcaaaggatc    8940
ttcttgagat cctttttttc tgcgcgtaat ctgctgcttg caaacaaaaa aaccaccgct    9000
accagcggtg gtttgtttgc cggatcaaga gctaccaact ctttttccga aggtaactgg    9060
cttcagcaga gcgcagatac caaatactgt ccttctagtg tagccgtagt taggccacca    9120
cttcaagaac tctgtagcac cgcctacata cctcgctctg ctaatcctgt taccagtggc    9180
tgctgccagt ggcgataagt cgtgtcttac cgggttggac tcaagacgat agttaccgga    9240
```

```
taaggcgcag cggtcgggct gaacgggggg ttcgtgcaca cagcccagct tggagcgaac    9300
gacctacacc gaactgagat acctacagcg tgagcattga gaaagcgcca cgcttcccga    9360
agggagaaag gcggacaggt atccggtaag cggcagggtc ggaacaggag agcgcacgag    9420
ggagcttcca gggggaaacg cctggtatct ttatagtcct gtcgggtttc gccacctctg    9480
acttgagcgt cgattttgt gatgctcgtc agggggcgg agcctatgga aaaacgccag      9540
caacgcggcc tttttacggt tcctggcctt tgctggcct tttgctcaca tgttctttcc     9600
tgcgttatcc cctgattctg tggataaccg tattaccgcc tttgagtgag ctgataccgc    9660
tcgccgcagc cgaacgaccg agcgcagcga gtcagtgagc gaggaagcgg aagagcgccc    9720
aatacgcaaa ccgcctctcc ccgcgcgttg ccgattcat taatgcagct gtggaatgtg     9780
tgtcagttag ggtgtggaaa gtccccaggc tccccagcag gcagaagtat gcaaagcatg    9840
catctcaatt agtcagcaac caggtgtgga aagtccccag gctccccagc aggcagaagt    9900
atgcaaagca tgcatctcaa ttagtcagca accatagtcc cgcccctaac tccgcccatc    9960
ccgcccctaa ctccgcccag ttccgcccat tctccgcccc atggctgact aatttttttt    10020
atttatgcag aggccgaggc cgcctcggcc tctgagctat tccagaagta gtgaggaggc    10080
ttttttggag gcctaggctt ttgcaaaaag cttggacaca agacaggctt gcgagatatg    10140
tttgagaata ccactttatc ccgcgtcagg gagaggcagt gcgtaaaaag acgcggactc    10200
atgtgaaata ctggttttta gtcgccaga tctctataat ctcgcgcaac ctattttccc     10260
ctcgaacact tttaagccg tagataaaca ggctgggaca cttcacatga gcgaaaaata     10320
catcgtcacc tgggacatgt tgcagatcca tgcacgtaaa ctcgcaagcc gactgatgcc    10380
ttctgaacaa tggaaaggca ttattgccgt aagccgtggc ggtctgtacc gggtgcgtta    10440
ctggcgcgtg aactgggtat tcgtcatgtc gataccgttt gtatttccag ctacgatcac    10500
gacaaccagc gcgagcttaa agtgctgaaa cgcgcagaag gcgatggcga aggcttcatc    10560
gttattgatg acctggtgga taccggtggt actgcggttg cgattcgtga atgtatcca     10620 aaagcgcact ttgtcaccat cttcgcaaaa ccggctggtc gtccgctggt tgatgactat    10680
gttgttgata tcccgcaaga tacctggatt gaacagccgt gggatatggg cgtcgtattc    10740
gtcccgccaa tctccggtcg ctaatctttt caacgcctgg cactgccggg cgttgttctt    10800
tttaacttca ggcgggttac aatagtttcc agtaagtatt ctggaggctg catccatgac    10860
acaggcaaac ctgagcgaaa ccctgttcaa accccgcttt aaacatcctg aaacctcgac    10920
gctagtccgc cgctttaatc acggcgcaca accgcctgtg cagtcggccc ttgatggtaa    10980
aaccatccct cactggtatc gcatgattaa ccgtctgatg tggatctggc gcggcattga    11040
cccacgcgaa atcctcgacg tccaggcacg tattgtgatg agcgatgccg aacgtaccga    11100
cgatgattta tacgatacgg tgattggcta ccgtggcggc aactggattt atgagtgggc    11160
cccggatctt tgtgaaggaa ccttacttct gtggtgtgac ataattggac aaactaccta    11220
cagagattta aagctctaag gtaaatataa aattttaag tgtataatgt gttaaactac      11280
tgattctaat tgtttgtgta ttttagattc aacctatgg aactgatgaa tgggagcagt      11340
ggtggaatgc ctttaatgag gaaaacctgt tttgctcaga gaaatgcca tctagtgatg      11400 atgaggctac tgctgactct caacattcta ctcctccaaa aagaagaga aggtagaag       11460 accccaagga ctttccttca gaattgctaa gttttttgag tcatgctgtg tttagtaata    11520
gaactcttgc ttgctttgct atttacacca caaaggaaaa agctgcactg ctatacaaga    11580
```

```
aaattatgga aaatattct gtaacctta taagtaggca taacagttat aatcataaca    11640
tactgttttt tcttactcca cacaggcata gagtgtctgc tattaataac tatgctcaaa    11700
aattgtgtac ctttagcttt ttaatttgta aaggggttaa taaggaatat ttgatgtata    11760
gtgccttgac tagagatcat aatcagccat accacatttg tagaggtttt acttgcttta    11820
aaaaacctcc cacacctccc cctgaacctg aaacataaaa tgaatgcaat tgttgttgtt    11880
aacttgttta ttgcagctta taatggttac aaataaagca atagcatcac aaatttcaca    11940
aataaagcat tttttttcact gcattctagt tgtggtttgt ccaaactcat caatgtatct    12000
tatcatgtct ggatcaactg gataactcaa gctaaccaaa atcatcccaa acttcccacc    12060
ccatacccta ttaccactgc caattaccta gtggtttcat ttactctaaa cctgtgattc    12120
ctctgaatta ttttcatttt aaagaaattg tatttgttaa atatgtacta caaacttagt    12180
ag                                                                   12182
```

<210> SEQ ID NO 6
<211> LENGTH: 6939
<212> TYPE: DNA
<213> ORGANISM: Artificial Sequence
<220> FEATURE:
<223> OTHER INFORMATION: A synthetic pMP71 gb NotIEcoRI mouse antiCD19
      for mouse T cell transduction

<400> SEQUENCE: 6

```
tcaaggttag gaacagagag acaggagaat atgggccaaa caggatatct gtggtaagca      60
gttcctgccc cggctcaggg ccaagaacag ttgaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgattga ctgcgtcgcc cgggtacccg tattcccaat aaagcctctt gctgtttgca     420
tccgaatcgt ggactcgctg atccttggga gggtctcctc agattgattg actgcccacc     480
tcgggggtct ttcatttgga ggttccaccg agatttggag acccctgccc agggaccacc     540
gacccccccg ccgggaggta agctggccag cggtcgtttc gtgtctgtct ctgtctttgg     600
gcgtgtttgt gccggcatct aatgtttgcg cctgcgtctg tactagttgg ctaactagat     660
ctgtatctgg cggtcccgcg gaagaactga cgagttcgta ttcccggccg cagcccctgg     720
gagacgtccc agcggcctcg ggggcccgtt ttgtggccca ttctgtatca gttaacctac     780
ccgagtcgga cttttggag ctccgccact gtccgagggg tacgtggctt tgttggggga     840
cgagagacag agacacttcc cgcccccgtc tgaattttg ctttcggttt tacgccgaaa     900
ccgcgccgcg cgtcttgtct gctgcagcat cgttctgtgt tgtctctgtc tgactgtgtt     960
tctgtatttg tctgaaaatt agctcgacaa agttaagtaa tagtccctct ctccaagctc    1020
acttacaggc atggggttc ccacccagct gttgggttg ctgctcctct ggatcactga    1080
tgccatctgc gaacagaagc tcatttctga agaagatctg gacatacaga tgacccagag    1140
tcctgccagc ttgtccacat ccctcggaga gaccgtgaca attcaatgcc aggcctctga    1200
ggacatatat tctggattgg cttggtacca gcaaaagcca ggtaaaagtc ctcagttgtt    1260
gatatacggc gcttctgatt tgcaagacgg ggtgccctca cgatttagcg ggtctggaag    1320
tggcactcag tacagtctga agattacttc aatgcaaaca gaagacgagg gtgtgtattt    1380
```

```
ttgccaacag gggctgacct acccaaggac attcggggc ggtacaaagc ttgaacttaa   1440
gggcggcggt gggtctggag gtggtggatc tggcggaggg ggaagtgagg tacagctgca   1500
acagtccggc gccgaactcg ttcgccctgg aacctcagtc aaattgtcat gcaaggtgag   1560
tggcgacaca ataacctttt actatatgca cttcgttaaa cagaggccag gtcaaggtct   1620
ggaatggata ggcagaattg atccagaaga tgagtccacc aaatactcag aaaagttcaa   1680
aaacaaagcc actcttactg ccgacacctc aagcaacaca gcatatctta agctcagttc   1740
acttaccagc gaagacaccg ccacctattt ttgtatttat ggtggctatt actttgacta   1800
ctggggggcaa ggtgttatgg taacagtttc ttccattgaa ttcatgtatc cacccccta   1860
tttggataat gaacgatcta atgggactat aatacatatc aaggaaaagc atctgtgtca   1920
tacccaaagt tccctaagc ttttctgggc cctcgtcgtt gtggcaggag tgctttttg    1980
ctatggattg ttggttactg tggctctctg cgtcatttgg acaaatagta ggaggaatcg   2040
ggggggacaa tctgattaca tgaacatgac accacggagg ccaggcctta ccagaaagcc   2100
ctaccaacct tatgcaccag cacgagactt cgccgcatac aggccaaggg ctaagtttc    2160
ccgcagcgcc gaaaccgcag ccaacctcca agatcctaat cagctctata acgaattgaa   2220
tcttggccgc agagaggagt acgacgtact tgagaaaaag agagctaggg accctgaaat   2280
gggtgggaag caacagcgaa gaaggaaccc acaggaaggg gtgtataatg cccttcaaaa   2340
ggataaaatg gcagaggcat acagtgaaat cggaaccaag ggggagagac gcagagggaa   2400
aggccatgac ggcctttatc agggtttgtc aactgctact aaagacactt atgatgcctt   2460
gcatatgcaa actctcgcac ccagatgacg agcatcttac cgccatttat tcccatattt   2520
gttctgtttt tcttgatttg ggtatacatt taaatgttaa taaaacaaaa tggtggggca   2580
atcatttaca ttttatggga tatgtaatta ctagttcagg tgtattgcca caagacaaac   2640
atgttaagaa actttcccgt tatttacgct ctgttcctgt taatcaacct ctggattaca   2700
aaatttgtga aagattgact gatattctta actatgttgc tccttttacg ctgtgtggat   2760
atgctgcttt aatgcctctg tatcatgcta ttgcttcccg tacggctttc gttttctcct   2820
ccttgtataa atcctggttg ctgtctcttt atgaggagtt gtggcccgtt gtccgtcaac   2880
gtggcgtggt gtgctctgtg tttgctgacg caaccccac tggctggggc attgccacca   2940
cctgtcaact cctttctggg actttcgctt ccccctccc gatcgccacg cagaactca    3000
tcgccgcctg ccttgcccgc tgctggacag gggctaggtt gctgggcact gataattccg   3060
tggtgttgtc ggggaagctg acgtcctttc catggctgct cgcctgtgtt gccaactgga   3120
tcctgcgcgg gacgtccttc tgctacgtcc cttcggctct caatccagcg gacctccctt   3180
cccgaggcct tctgccggtt ctgccggcctc tcccgcgtct tcgctttcgg cctccgacga   3240
gtcggatctc cctttgggcc gcctcccgc ctgtttcgcc tcggcgtccg gtccgtgttg   3300
cttggtcgtc acctgtgcag aattgcgaac catggattcc accgtgaact ttgtctcctg   3360
gcatgcaaat cgtcaacttg gcatgccaag aattaattcg gatccaagct taggcctgct   3420
cgctttcttg ctgtcccatt tctattaaag gttccttgt tccctaagtc caactactaa    3480
actgggggat attatgaagg gccttgagca tctggattct gcctagcgct aagcttccta   3540
acacgagcca tagatagaat aaaagatttt atttagtctc cagaaaaagg ggggaatgaa   3600
agaccccacc tgtaggtttg gcaagctagc ttaagtaagc cattttgcaa ggcatggaaa   3660
aatacataac tgagaataga gaagttcaga tcaaggttag gaacagagag acaggagaat   3720
atgggccaaa caggatatct gtggtaagca gttcctgccc cggctcaggg ccaagaacag   3780
```

```
ttggaacagc agaatatggg ccaaacagga tatctgtggt aagcagttcc tgccccggct    3840
cagggccaag aacagatggt ccccagatgc ggtcccgccc tcagcagttt ctagagaacc    3900
atcagatgtt tccagggtgc cccaaggacc tgaaatgacc ctgtgcctta tttgaactaa    3960
ccaatcagtt cgcttctcgc ttctgttcgc gcgcttctgc tccccgagct caataaaaga    4020
gcccacaacc cctcactcgg cgcgccagtc ctccgataga ctgcgtcgcc cggggtaccc    4080
gtattcccaa taaagcctct tgctgtttgc atccgaatcg tggactcgct gatccttggg    4140
agggtctcct cagattgatt gactgcccac ctcgggggtc tttcattctc gagagctttg    4200
gcgtaatcat ggtcatagct gtttcctgtg tgaaattgtt atccgctcac aattccacac    4260
aacatacgag ccggaagcat aaagtgtaaa gcctggggtg cctaatgagt gagctaactc    4320
acattaattg cgttgcgctc actgcccgct ttccagtcgg gaaacctgtc gtgccagctg    4380
cattaatgaa tcggccaacg cgcggggaga ggcggtttgc gtattgggcg ctcttccgct    4440
tcctcgctca ctgactcgct gcgctcggtc gttcggctgc ggcgagcggt atcagctcac    4500
tcaaaggcgg taatacggtt atccacagaa tcaggggata acgcaggaaa gaacatgtga    4560
gcaaaaggcc agcaaaaggc caggaaccgt aaaaaggccg cgttgctggc gtttttccat    4620
aggctccgcc cccctgacga gcatcacaaa aatcgacgct caagtcagag gtggcgaaac    4680
ccgacaggac tataaagata ccaggcgttt ccccctggaa gctccctcgt gcgctctcct    4740
gttccgaccc tgccgcttac cggatacctg tccgcctttc tcccttcggg aagcgtggcg    4800
ctttctcaat gctcacgctg taggtatctc agttcggtgt aggtcgttcg ctccaagctg    4860
ggctgtgtgc acgaaccccc cgttcagccc gaccgctgcg ccttatccgg taactatcgt    4920
cttgagtcca acccggtaag acacgactta tcgccactgg cagcagccac tggtaacagg    4980
attagcagag cgaggtatgt aggcggtgct acagagttct tgaagtggtg gcctaactac    5040
ggctacacta aaggacagt atttggtatc tgcgctctgc tgaagccagt taccttcgga    5100
aaaagagttg gtagctcttg atccggcaaa caaaccaccg ctggtagcgg tggtttttt    5160 gtttgcaagc agcagattac gcgcagaaaa aaaggatctc aagaagatcc tttgatcttt    5220
tctacggggt ctgacgctca gtggaacgaa aactcacgtt aagggatttt ggtcatgaga    5280
ttatcaaaaa ggatcttcac ctagatcctt ttaaattaaa aatgaagttt taaatcaatc    5340
taaagtatat atgagtaaac ttggtctgac agttaccaat gcttaatcag tgaggcacct    5400
atctcagcga tctgtctatt tcgttcatcc atagttgcct gactccccgt cgtgtagata    5460
actacgatac gggagggctt accatctggc cccagtgctg caatgatacc gcgagaccca    5520
cgctcaccgg ctccagattt atcagcaata accagccag ccggaagggc cgagcgcaga    5580
agtggtcctg caactttatc cgcctccatc cagtctatta attgttgccg gaagctaga    5640 gtaagtagtt cgccagttaa tagtttgcgc aacgttgttg ccattgctgc tggcatcgtg    5700
gtgtcacgct cgtcgtttgg tatggcttca ttcagctccg gttcccaacg atcaaggcga    5760
gttacatgat cccccatgtt gtgcaaaaaa gcggttagct ccttcggtcc tccgatcgtt    5820
gtcagaagta agttggccgc agtgttatca ctcatggtta tggcagcact gcataattct    5880
cttactgtca tgccatccgt aagatgcttt tctgtgactg gtgagtactc aaccaagtca    5940
ttctgagaat agtgtatgcg gcgaccgagt tgctcttgcc cggcgtcaat acgggataat    6000
accgcgccac atagcagaac tttaaaagtg ctcatcattg gaaaacgttc ttcggggcga    6060
aaactctcaa ggatcttacc gctgttgaga tccagttcga tgtaacccac tcgtgcaccc    6120
```

| | |
|---|---|
| aactgatctt cagcatcttt tactttcacc agcgtttctg ggtgagcaaa acaggaagg | 6180 |
| caaaatgccg caaaaaggg aataagggcg acacggaaat gttgaatact catactcttc | 6240 |
| cttttcaat attattgaag catttatcag ggttattgtc tcatgagcgg atacatattt | 6300 |
| gaatgtattt agaaaaataa acaaataggg gttccgcgca catttccccg aaaagtgcca | 6360 |
| cctgacgtct aagaaaccat tattatcatg acattaacct ataaaaatag gcgtatcacg | 6420 |
| aggcccttc gtcttcaagc tgcctcgcgc gtttcggtga tgacggtgaa aacctctgac | 6480 |
| acatgcagct cccggagacg gtcacagctt gtctgtaagc ggatgccggg agcagacaag | 6540 |
| cccgtcaggg cgcgtcagcg ggtgttggcg ggtgtcgggg cgcagccatg acccagtcac | 6600 |
| gtagcgatag ttactatgcg gcatcagagc agattgtact gagagtgcac catatgcggt | 6660 |
| gtgaaatacc gcacagatgc gtaaggagaa aataccgcat caggcgccat tcgccattca | 6720 |
| ggctgcgcaa ctgttgggaa gggcgatcgg tgcgggcctc ttcgctatta cgccagctgg | 6780 |
| cgaaaggggg atgtgctgca aggcgattaa gttgggtaac gccagggttt cccagtcac | 6840 |
| gacgttgtaa aacgacggcc agtgaattag tactctagct taagtaagcc attttgcaag | 6900 |
| gcatggaaaa atacataact gagaatagag aagttcaga | 6939 |

<210> SEQ ID NO 7
<211> LENGTH: 12188
<212> TYPE: DNA
<213> ORGANISM: Artificial Sequence
<220> FEATURE:
<223> OTHER INFORMATION: A synthetic pWPI-FRa 1-24 FKBP FRa

<400> SEQUENCE: 7

| | |
|---|---|
| ttggaagggc taattcactc ccaaagaaga caagatatcc ttgatctgtg gatctaccac | 60 |
| acacaaggct acttccctga ttagcagaac tacacaccag gccagggt cagatatcca | 120 |
| ctgacctttg gatggtgcta caagctagta ccagttgagc cagataaggt agaagaggcc | 180 |
| aataaaggag agaacaccag cttgttacac cctgtgagcc tgcatgggat ggatgacccg | 240 |
| gagagagaag tgttagagtg gaggtttgac agccgcctag catttcatca cgtggcccga | 300 |
| gagctgcatc cggagtactt caagaactgc tgatatcgag cttgctacaa gggactttcc | 360 |
| gctggggact ttccagggag gcgtggcctg ggcgggactg ggagtggcg agccctcaga | 420 |
| tcctgcatat aagcagctgc tttttgcctg tactgggtct ctctggttag accagatctg | 480 |
| agcctgggag ctctctggct aactagggaa cccactgctt aagcctcaat aaagcttgcc | 540 |
| ttgagtgctt caagtagtgt gtgcccgtct gttgtgtgac tctggtaact agagatccct | 600 |
| cagaccctt tagtcagtgt ggaaaatctc tagcagtggc gcccgaacag ggacttgaaa | 660 |
| gcgaaaggga accagagga gctctctcga cgcaggactc ggcttgctga gcgcgcacg | 720 |
| gcaagaggcg agggcggcg actggtgagt acgccaaaaa ttttgactag cggaggctag | 780 |
| aaggagagag atgggtgcga gagcgtcagt attaagcggg ggagaattag atcgcgatgg | 840 |
| gaaaaaattc ggttaaggcc agggggaaag aaaaaatata aattaaaaca tatagtatgg | 900 |
| gcaagcaggg agctagaacg attcgcagtt aatcctggcc tgttagaaac atcagaaggc | 960 |
| tgtagacaaa tactgggaca gctacaacca tcccttcaga caggatcaga agaacttaga | 1020 |
| tcattatata atacagtagc aaccctctat tgtgtgcatc aaaggataga gataaaagac | 1080 |
| accaaggaag ctttagacaa gatagaggaa gagcaaaaca aaagtaagac caccgcacag | 1140 |
| caagcggccc ctgatcttca gacctggagg aggagatatg agggacaatt ggagaagtga | 1200 |
| attatataaa tataaagtag taaaaattga accattagga gtagcaccca ccaaggcaaa | 1260 |

```
gagaagagtg gtgcagagag aaaaaagagc agtgggaata ggagctttgt tccttgggtt   1320
cttgggagca gcaggaagca ctatgggcgc agcgtcaatg acgctgacgg tacaggccag   1380
acaattattg tctggtatag tgcagcagca gaacaatttg ctgagggcta ttgaggcgca   1440
acagcatctg ttgcaactca cagtctgggg catcaagcag ctccaggcaa gaatcctggc   1500
tgtggaaaga tacctaaagg atcaacagct cctgggggatt tggggttgct ctggaaaact   1560
catttgcacc actgctgtgc cttggaatgc tagttggagt aataaatctc tggaacagat   1620
ttggaatcac acgacctgga tggagtggga cagagaaatt aacaattaca caagcttaat   1680
acactcctta attgaagaat cgcaaaacca gcaagaaaag aatgaacaag aattattgga   1740
attagataaa tgggcaagtt tgtggaattg gtttaacata caaaattggc tgtggtatat   1800
aaaattattc ataatgatag taggaggctt ggtaggttta agaatagttt ttgctgtact   1860
ttctatagtg aatagagtta ggcagggata ttcaccatta tcgtttcaga cccacctccc   1920
aaccccgagg ggacccgaca ggcccgaagg aatagaagaa gaaggtggag agagagacag   1980
agacagatcc attcgattag tgaacggatc tcgacggtat cgatgtcgac gataagcttt   2040
gcaaagatgt ataagttttt aaacagagag gaatctttgc agctaatgga ccttctaggt   2100
cttgaaagga gtgggaattg gctccggtgc ccgtcagtgg gcagagcgca catcgcccac   2160
agtccccgag aagttggggg gaggggtcgg caattgaacc ggtgcctaga gaaggtggcg   2220
cggggtaaac tgggaaagtg atgtcgtgta ctggctccgc cttttcccg agggtggggg   2280 agaaccgtat ataagtgcag tagtcgccgt gaacgttctt tttcgcaacg ggtttgccgc   2340
cagaacacag gtaagtgccg tgtgtggttc ccgcgggcct ggcctcttta cgggttatgg   2400
cccttgcgtg ccttgaatta cttccactgg ctgcagtacg tgattcttga tcccgagctt   2460
cgggttggaa gtgggtggga gagttcgagg ccttgcgctt aaggagcccc ttcgcctcgt   2520
gcttgagttg aggcctggcc tgggcgctgg ggccgccgcg tgcgaatctg gtggcacctt   2580
cgcgcctgtc tcgctgcttt cgataagtct ctagccattt aaaattttg atgacctgct   2640 gcgacgcttt ttttctggca agatagtctt gtaaatgcgg gccaagatct gcacactggt   2700
atttcggttt ttggggccgc gggcggcgac ggggcccgtg cgtcccagcg cacatgttcg   2760
gcgaggcggg gcctgcgagc gcggccaccg agaatcggac gggggtagtc tcaagctggc   2820
cggcctgctc tggtgcctgg cctcgcgccg ccgtgtatcg ccccgccctg ggcggcaagg   2880
ctggcccggt cggcaccagt tgcgtgagcg gaaagatggc cgcttcccgg ccctgctgca   2940
gggagctcaa aatggaggac gcggcgctcg ggagagcggg cgggtgagtc acccacacaa   3000
aggaaaaggg cctttccgtc ctcagccgtc gcttcatgtg actccacgga gtaccgggcg   3060 ccgtccagge acctcgatta gttctcgagc ttttggagta cgtcgtcttt aggttggggg   3120 gagggtttt atgcgatgga gtttccccac actgagtggg tggagactga agttaggcca   3180
gcttggcact tgatgtaatt ctccttggaa tttgcccttt ttgagtttgg atcttggttc   3240
attctcaagc ctcagacagt ggttcaaagt ttttttcttc catttcaggt gtcgtgagga   3300
atttcgacat ttaaatttaa ttaatctcga cggtatcggt taactttaa aagaaagggg   3360 gggattgggg ggtacagtgc aggggaaaga atagtagaca taatagcaac agacatacaa   3420
actaaagaat tacaaaaaca aattacaaaa attcaaaatt ttatcgatca cgagactagc   3480
ctcgaggttt atggctcagc ggatgacaac acagctgctg ctccttctag tgtgggtggc   3540
tgtagtaggg gaggctcaga caggagtgca ggtggagact atctccccag gagacgggcg   3600
```

```
caccttcccc aagcgcggcc agacctgcgt ggtgcactac accgggatgc ttgaagatgg    3660
aaagaaattt gattcctccc gggacagaaa caagcccttt aagtttatgc taggcaagca    3720
ggaggtgatc cgaggctggg aagaaggggt tgcccagatg agtgtgggtc agagagccaa    3780
actgactata tctccagatt atgcctatgg tgccactggg cacccaggca tcatcccacc    3840
acatgccact ctcgtcttcg atgtggagct tctaaaactg gaatctggcg gtggatccag    3900
gattgcatgg gccaggactg agcttctcaa tgtctgcatg aacgccaagc accacaagga    3960
aaagccaggc cccgaggaca agttgcatga gcagtgtcga ccctggagga agaatgcctg    4020
ctgttctacc aacaccagcc aggaagccca taaggatgtt tcctacctat atagattcaa    4080
ctggaaccac tgtggagaga tggcacctgc ctgcaaacgg catttcatcc aggacacctg    4140
cctctacgag tgctccccca acttggggcc ctggatccag caggtggatc agagctggcg    4200
caaagagcgg gtactgaacg tgcccctgtg caaagaggac tgtgagcaat ggtgggaaga    4260
ttgtcgcacc tcctacacct gcaagagcaa ctggcacaag ggctggaact ggacttcagg    4320
gtttaacaag tgcgcagtgg gagctgcctg ccaacctttc catttctact tccccacacc    4380
cactgttctg tgcaatgaaa tctggactca ctcctacaag gtcagcaact acagccgagg    4440
gagtggccgc tgcatccaga tgtggttcga cccagcccag ggcaacccca atgaggaggt    4500
ggcgaggttc tatgctgcag ccatgagtgg ggctgggccc tgggcagcct ggccttccct    4560
gcttagcctg gccctaatgc tgctgtggct gctcagctga aaactacggg ctgcaggaat    4620
tccgcccccc cccccctaac gttactggcc gaagccgctt ggaataaggc cggtgtgcgt    4680
ttgtctatat gttattttcc accatattgc cgtcttttgg caatgtgagg gcccggaaac    4740
ctggccctgt cttcttgacg agcattccta ggggtctttc cctctcgcc aaaggaatgc    4800 aaggtctgtt gaatgtcgtg aaggaagcag ttcctctgga agcttcttga agacaaacaa    4860
cgtctgtagc gaccctttgc aggcagcgga accccccacc tggcgacagg tgcctctgcg    4920
gccaaaagcc acgtgtataa gatacacctg caaaggcggc acaaccccag tgccacgttg    4980
tgagttggat agttgtggaa agagtcaaat ggctctcctc aagcgtattc aacaaggggc    5040
tgaaggatgc ccagaaggta ccccattgta tgggatctga tctggggcct cggtgcacat    5100
gctttacatg tgtttagtcg aggttaaaaa acgtctaggc cccccgaacc acggggacgt    5160
ggttttcctt tgaaaaacac gatgataata ccatggtgag caaggcgag gagctgttca    5220 ccggggtggt gcccatcctg gtcgagctgg acggcgacgt aaacggccac aagttcagcg    5280
tgtccggcga gggcgagggc gatgccacct acggcaagct gaccctgaag ttcatctgca    5340
ccaccggcaa gctgcccgtg ccctggccca cccctcgtgac cacccctgacc tacggcgtgc    5400 agtgcttcag ccgctacccc gaccacatga gcagcacga cttcttcaag tccgccatgc    5460
ccgaaggcta cgtccaggag cgcaccatct tcttcaagga cgacggcaac tacaagaccc    5520
gcgccgaggt gaagttcgag ggcgacaccc tggtgaaccg catcgagctg aagggcatcg    5580
acttcaagga ggacggcaac atcctggggc acaagctgga gtacaactac aacagccaca    5640
acgtctatat catggccgac aagcagaaga acggcatcaa ggtgaacttc aagatccgcc    5700
acaacatcga ggacggcagc gtgcagctcg ccgaccacta ccagcagaac ccccccatcg    5760
gcgacggccc cgtgctgctg cccgacaacc actacctgag cacccagtcc gccctgagca    5820
aagaccccaa cgagaagcgc gatcacatgg tcctgctgga gttcgtgacc gccgccggga    5880
tcactctcgg catggacgag ctgtacaagt ccggactcag atctcgacta gctagtagct    5940
agctagctag tcgagctcaa gcttcgaatt cgatatcaag cttatcgcga taccgtcgac    6000
```

```
ctcgagggaa ttccgataat caacctctgg attacaaaat ttgtgaaaga ttgactggta      6060
ttcttaacta tgttgctcct tttacgctat gtggatacgc tgctttaatg cctttgtatc      6120
atgctattgc ttcccgtatg gctttcattt tctcctcctt gtataaatcc tggttgctgt      6180
ctctttatga ggagttgtgg cccgttgtca ggcaacgtgg cgtggtgtgc actgtgtttg      6240
ctgacgcaac ccccactggt tggggcattg ccaccacctg tcagctcctt tccgggactt      6300
tcgctttccc cctccctatt gccacggcgg aactcatcgc cgcctgcctt gcccgctgct      6360
ggacaggggc tcggctgttg ggcactgaca attccgtggt gttgtcgggg aagctgacgt      6420
cctttccatg gctgctcgcc tgtgttgcca cctggattct gcgcgggacg tccttctgct      6480
acgtcccttc ggccctcaat ccagcggacc ttccttcccg cggcctgctg ccggctctgc      6540
ggcctcttcc gcgtcttcgc cttcgccctc agacgagtcg gatctccctt tgggccgcct      6600
ccccgcatcg ggaattcgag ctcggtacct ttaagaccaa tgacttacaa ggcagctgta      6660
gatcttagcc acttttaaa agaaaagggg ggactggaag gctaattca ctcccaacga      6720
agacaagatg ggatcaattc accatgggaa taacttcgta tagcatacat tatacgaagt      6780
tatgctgctt tttgcttgta ctgggtctct ctggttagac cagatctgag cctgggagct      6840
ctctggctaa ctagggaacc cactgcttaa gcctcaataa agcttgcctt gagtgcttca      6900
agtagtgtgt gcccgtctgt tgtgtgactc tggtaactag agatccctca gacccttta      6960
gtcagtgtgg aaaatctcta gcagcatcta gaattaattc cgtgtattct atagtgtcac      7020
ctaaatcgta tgtgtatgat acataaggtt atgtattaat tgtagccgcg ttctaacgac      7080
aatatgtaca agcctaattg tgtagcatct ggcttactga agcagaccct atcatctctc      7140
tcgtaaactg ccgtcagagt cggtttggtt ggacgaacct tctgagtttc tggtaacgcc      7200
gtcccgcacc cggaaatggt cagcgaacca atcagcaggg tcatcgctag ccagatcctc      7260
tacgccggac gcatcgtggc cggcatcacc ggcgccacag gtgcggttgc tggcgcctat      7320
atcgccgaca tcaccgatgg ggaagatcgg gctcgccact tcgggctcat gagcgcttgt      7380
ttcggcgtgg gtatggtggc aggccccgtg gccggggac tgttgggcgc catctccttg      7440
catgcaccat tccttgcggc ggcggtgctc aacggcctca acctactact gggctgcttc      7500
ctaatgcagg agtcgcataa gggagagcgt cgaatggtgc actctcagta caatctgctc      7560
tgatgccgca tagttaagcc agccccgaca cccgccaaca cccgctgacg cgccctgacg      7620
ggcttgtctg ctcccggcat ccgcttacag acaagctgtg accgtctccg ggagctgcat      7680
gtgtcagagg ttttcaccgt catcaccgaa acgcgcgaga cgaaagggcc tcgtgatacg      7740
cctattttta taggttaatg tcatgataat aatggtttct tagacgtcag gtggcacttt      7800
tcggggaaat gtgcgcggaa cccctatttg tttattttc taaatacatt caaatatgta      7860
tccgctcatg agacaataac cctgataaat gcttcaataa tattgaaaaa ggaagagtat      7920
gagtattcaa catttccgtg tcgcccttat tcccttttt gcggcatttt gccttcctgt      7980
ttttgctcac ccagaaacgc tggtgaaagt aaaagatgct gaagatcagt tgggtgcacg      8040
agtgggttac atcgaactgg atctcaacag cggtaagatc cttgagagtt ttcgccccga      8100
agaacgtttt ccaatgatga gcacttttaa agttctgcta tgtggcgcgg tattatcccg      8160
tattgacgcc gggcaagagc aactcggtcg ccgcatacac tattctcaga atgacttggt      8220
tgagtactca ccagtcacag aaaagcatct tacggatggc atgacagtaa gagaattatg      8280
cagtgctgcc ataaccatga gtgataacac tgcggccaac ttacttctga caacgatcgg      8340
```

```
aggaccgaag gagctaaccg ctttttttgca caacatgggg gatcatgtaa ctcgccttga    8400
tcgttgggaa ccggagctga atgaagccat accaaacgac gagcgtgaca ccacgatgcc    8460
tgtagcaatg gcaacaacgt tgcgcaaact attaactggc gaactactta ctctagcttc    8520
ccggcaacaa ttaatagact ggatggaggc ggataaagtt gcaggaccac ttctgcgctc    8580
ggcccttccg gctggctggt ttattgctga taaatctgga gccggtgagc gtgggtctcg    8640
cggtatcatt gcagcactgg ggccagatgg taagccctcc cgtatcgtag ttatctacac    8700
gacggggagt caggcaacta tggatgaacg aaatagacag atcgctgaga taggtgcctc    8760
actgattaag cattggtaac tgtcagacca agtttactca tatatacttt agattgattt    8820
aaaacttcat ttttaattta aaaggatcta ggtgaagatc ctttttgata atctcatgac    8880
caaaatccct taacgtgagt tttcgttcca ctgagcgtca gaccccgtag aaaagatcaa    8940
aggatcttct tgagatcctt ttttttctgcg cgtaatctgc tgcttgcaaa caaaaaaacc    9000
accgctacca gcggtggttt gtttgccgga tcaagagcta ccaactcttt ttccgaaggt    9060
aactggcttc agcagagcgc agataccaaa tactgtcctt ctagtgtagc cgtagttagg    9120
ccaccacttc aagaactctg tagcaccgcc tacataccct gctctgctaa tcctgttacc    9180
agtggctgct gccagtggcg ataagtcgtg tcttaccggg ttggactcaa gacgatagtt    9240
accggataag gcgcagcggt cgggctgaac ggggggttcg tgcacacagc ccagcttgga    9300
gcgaacgacc tacaccgaac tgagatacct acagcgtgag cattgagaaa gcgccacgct    9360
tcccgaaggg agaaaggcgg acaggtatcc ggtaagcggc agggtcggaa caggagagcg    9420
cacgagggag cttccagggg gaaacgcctg gtatctttat agtcctgtcg ggtttcgcca    9480
cctctgactt gagcgtcgat ttttgtgatg ctcgtcaggg gggcggagcc tatggaaaaa    9540
cgccagcaac gcggcctttt tacgttcct ggccttttgc tggccttttg ctcacatgtt    9600
ctttcctgcg ttatcccctg attctgtgga taaccgtatt accgcctttg agtgagctga    9660
taccgctcgc cgcagccgaa cgaccgagcg cagcgagtca gtgagcgagg aagcggaaga    9720
gcgcccaata cgcaaaccgc ctctccccgc gcgttggccg attcattaat gcagctgtgg    9780
aatgtgtgtc agttagggtg tggaaagtcc ccaggctccc cagcaggcag aagtatgcaa    9840
agcatgcatc tcaattagtc agcaaccagg tgtggaaagt ccccaggctc cccagcaggc    9900
agaagtatgc aaagcatgca tctcaattag tcagcaacca tagtcccgcc ctaactccg    9960
cccatcccgc ccctaactcc gcccagttcc gcccattctc cgccccatgg ctgactaatt   10020
ttttttattt atgcagaggc cgaggccgcc tcggcctctg agctattcca gaagtagtga   10080
ggaggctttt ttggaggcct aggcttttgc aaaaagcttg gacacaagac aggcttgcga   10140
gatatgtttg agaataccac tttatcccgc gtcaggagga ggcagtgcgt aaaaagacgc   10200
ggactcatgt gaaatactgg ttttttagtgc gccagatctc tataatctcg cgcaacctat   10260
tttccctcg aacactttt aagccgtaga taaacaggct gggacacttc acatgagcga   10320
aaaatacatc gtcacctggg acatgttgca gatccatgca cgtaaactcg caagccgact   10380
gatgccttct gaacaatgga aaggcattat tgccgtaagc cgtggcggtc tgtaccgggt   10440
gcgttactgg cgcgtgaact gggtattcgt catgtcgata ccgtttgtat ttccagctac   10500
gatcacgaca accagcgcga gcttaaagtg ctgaaacgcg cagaaggcga tggcgaaggc   10560
ttcatcgtta ttgatgacct ggtggatacc ggtggtactg cggttgcgat tcgtgaaatg   10620
tatccaaaag cgcactttgt caccatcttc gcaaaaccgg ctggtcgtcc gctggttgat   10680
gactatgttg ttgatatccc gcaagatacc tggattgaac agccgtggga tatgggcgtc   10740
```

```
gtattcgtcc cgccaatctc cggtcgctaa tcttttcaac gcctggcact gccgggcgtt    10800 gttctttta  acttcaggcg ggttacaata gtttccagta agtattctgg aggctgcatc    10860
catgacacag gcaaacctga gcgaaaccct gttcaaaccc cgctttaaac atcctgaaac    10920
ctcgacgcta gtccgccgct ttaatcacgg cgcacaaccg cctgtgcagt cggcccttga    10980
tggtaaaacc atccctcact ggtatcgcat gattaaccgt ctgatgtgga tctggcgcgg    11040
cattgaccca cgcgaaatcc tcgacgtcca ggcacgtatt gtgatgagcg atgccgaacg    11100
taccgacgat gatttatacg atacggtgat tggctaccgt ggcggcaact ggatttatga    11160
gtgggccccg gatctttgtg aaggaacctt acttctgtgg tgtgacataa ttggacaaac    11220
tacctacaga gatttaaagc tctaaggtaa atataaaatt tttaagtgta taatgtgtta    11280
aactactgat tctaattgtt tgtgtatttt agattccaac ctatgaact  gatgaatggg    11340 agcagtggtg gaatgccttt aatgaggaaa acctgttttg ctcagaagaa atgccatcta    11400
gtgatgatga ggctactgct gactctcaac attctactcc tccaaaaaag aagagaaagg    11460
tagaagaccc caaggacttt ccttcagaat tgctaagttt tttgagtcat gctgtgttta    11520
gtaatagaac tcttgcttgc tttgctattt acaccacaaa ggaaaaagct gcactgctat    11580
acaagaaaat tatggaaaaa tattctgtaa cctttataag taggcataac agttataatc    11640
ataacatact gttttttctt actccacaca ggcatagagt gtctgctatt aataactatg    11700
ctcaaaaatt gtgtaccttt agcttttaa  tttgtaaagg ggttaataag gaatatttga    11760
tgtatagtgc cttgactaga gatcataatc agccatacca catttgtaga ggttttactt    11820
gctttaaaaa acctcccaca cctcccctg  aacctgaaac ataaaatgaa tgcaattgtt    11880
gttgttaact tgtttattgc agcttataat ggttacaaat aaagcaatag catcacaaat    11940
ttcacaaata aagcattttt ttcactgcat tctagttgtg gtttgtccaa actcatcaat    12000
gtatcttatc atgtctggat caactggata actcaagcta accaaaatca tcccaaactt    12060 cccacccccat accctattac cactgccaat tacctagtgg tttcatttac tctaaacctg    12120
tgattcctct gaattatttt cattttaaag aaattgtatt tgttaaatat gtactacaaa    12180
cttagtag                                                              12188
```

<210> SEQ ID NO 8
<211> LENGTH: 12182
<212> TYPE: DNA
<213> ORGANISM: Artificial Sequence
<220> FEATURE:
<223> OTHER INFORMATION: A synthetic pWPI mFKBP-mFRa SGGGS

<400> SEQUENCE: 8

```
ttggaagggc taattcactc ccaaagaaga caagatatcc ttgatctgtg gatctaccac      60
acacaaggct acttccctga ttagcagaac tacacaccag ggccaggggt cagatatcca     120
ctgacctttg gatggtgcta caagctagta ccagttgagc cagataaggt agaagaggcc     180
aataaaggag agaacaccag cttgttacac cctgtgagcc tgcatgggat ggatgacccg     240
gagagagaag tgttagagtg gaggtttgac agccgcctag catttcatca cgtggcccga     300
gagctgcatc cggagtactt caagaactgc tgatatcgag cttgctacaa gggactttcc     360
gctggggact ttccagggag gcgtggcctg ggcgggactg ggagtggcg  agccctcaga     420 tcctgcatat aagcagctgc tttttgcctg tactgggtct ctctggttag accagatctg     480
agcctgggag ctctctggct aactagggaa cccactgctt aagcctcaat aaagcttgcc     540
```

```
ttgagtgctt caagtagtgt gtgcccgtct gttgtgtgac tctggtaact agagatccct    600
cagacccttt tagtcagtgt ggaaaatctc tagcagtggc gcccgaacag ggacttgaaa    660
gcgaaaggga aaccagagga gctctctcga cgcaggactc ggcttgctga agcgcgcacg    720
gcaagaggcg aggggcggcg actggtgagt acgccaaaaa ttttgactag cggaggctag    780
aaggagagag atgggtgcga gagcgtcagt attaagcggg ggagaattag atcgcgatgg    840
gaaaaaattc ggttaaggcc agggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg ctgatcttca gacctggagg aggagatatg agggacaatt ggagaagtga   1200
attatataaa tataaagtag taaaaattga accattagga gtagcaccca ccaaggcaaa   1260
gagaagagtg gtgcagagag aaaaaagagc agtgggaata ggagctttgt tccttgggtt   1320
cttgggagca gcaggaagca ctatgggcgc agcgtcaatg acgctgacgg tacaggccag   1380
acaattattg tctggtatag tgcagcagca gaacaatttg ctgagggcta ttgaggcgca   1440
acagcatctg ttgcaactca cagtctgggg catcaagcag ctccaggcaa gaatcctggc   1500
tgtggaaaga tacctaaagg atcaacagct cctgggaatt tggggttgct ctggaaaact   1560
catttgcacc actgctgtgc cttggaatgc tagttggagt aataaatctc tggaacagat   1620
ttggaatcac acgacctgga tggagtggga cagagaaatt aacaattaca caagcttaat   1680
acactcctta attgaagaat cgcaaaacca gcaagaaaag aatgaacaag aattattgga   1740
attagataaa tgggcaagtt tgtggaattg gtttaacata acaaattggc tgtggtatat   1800
aaaattattc ataatgatag taggaggctt ggtaggttta agaatagttt ttgctgtact   1860
ttctatagtg aatagagtta ggcagggata ttcaccatta tcgtttcaga cccacctccc   1920
aaccccgagg ggacccgaca ggcccgaagg aatagaagaa gaaggtggag agagagacag   1980
agacagatcc attcgattag tgaacggatc tcgacggtat cgatgtcgac gataagcttt   2040
gcaaagatgg ataaagtttt aaacagagag gaatctttgc agctaatgga ccttctaggt   2100
cttgaaagga gtgggaattg gctccggtgc ccgtcagtgg gcagagcgca catcgcccac   2160
agtccccgag aagttggggg gaggggtcgg caattgaacc ggtgcctaga aaggtggcg    2220 cggggtaaac tgggaaagtg atgtcgtgta ctggctccgc cttttttccg agggtggggg   2280
agaaccgtat ataagtgcag tagtcgccgt gaacgttctt tttcgcaacg ggtttgccgc   2340
cagaacacag gtaagtgccg tgtgtggttc ccgcgggcct ggcctcttta cgggttatgg   2400
cccttgcgtg ccttgaatta cttccactgg ctgcagtacg tgattcttga tcccgagctt   2460
cgggttggaa gtgggtggga gagttcgagg ccttgcgctt aaggagcccc ttcgcctcgt   2520
gcttgagttg aggcctggcc tgggcgctgg ggccgccgcg tgcgaatctg gtggcacctt   2580
cgcgcctgtc tcgctgcttt cgataagtct ctagccattt aaaattttg atgacctgct    2640 gcgacgcttt ttttctggca agatagtctt gtaaatgcgg gccaagatct gcacactggt   2700
atttcggttt ttggggccgc gggcggcgac ggggcccgtg cgtcccagcg cacatgttcg   2760
gcgaggcggg gcctgcgagc gcggccaccg agaatcggac gggggtagtc tcaagctggc   2820
cggcctgctc tggtgcctgg cctcgcgccg ccgtgtatcg ccccgccctg gcggcaagg    2880 ctggcccggt cggcaccagt tgcgtgagcg gaaagatggc cgcttcccgg ccctgctgca   2940
```

```
gggagctcaa aatggaggac gcggcgctcg ggagagcggg cgggtgagtc acccacacaa    3000
aggaaaaggg cctttccgtc ctcagccgtc gcttcatgtg actccacgga gtaccgggcg    3060
ccgtccaggc acctcgatta gttctcgagc ttttggagta cgtcgtcttt aggttggggg    3120
gaggggtttt atgcgatgga gtttccccac actgagtggg tggagactga agttaggcca    3180
gcttggcact tgatgtaatt ctccttggaa tttgcccttt ttgagtttgg atcttggttc    3240
attctcaagc ctcagacagt ggttcaaagt ttttttcttc catttcaggt gtcgtgagga    3300
atttcgacat ttaaatttaa ttaatctcga cggtatcggt taacttttaa aagaaaaggg    3360
gggattgggg ggtacagtgc aggggaaaga atagtagaca taatagcaac agacatacaa    3420
actaaagaat tacaaaaaca aattacaaaa attcaaaatt ttatcgatca cgagactagc    3480
ctcgaggttt atggctcacc tgatgactgt gcagttgttg ctcctggtga tgtggatggc    3540
cgaatgtgct cagtccagag ctggagtgca ggtggagacc atctctcctg gagacgggcg    3600
caccttccca aagcgcggcc agacctgcgt ggtgcactac acggggatgc ttgaagatgg    3660
aaagaaattt gattcctctc gggacagaaa caagcctttt aagtttacac taggcaagca    3720
ggaggtgatc cgaggctggg aggaaggggt agcccagatg agtgtgggtc agagagccaa    3780
actgataatc tcctcagact atgcctatgg agccaccggg cacccaggca tcatcccacc    3840
acatgccact cttgtttttg atgtggagct tctaaaactg gaaagcggcg gcggcagcac    3900
tcgggccagg actgaacttc tcaatgtctg catggatgcc aaacaccaca agaaaaacc    3960 gggccctgag gacaatttac acgaccagtg cagcccctgg aagacgaatt cctgctgttc    4020
cacgaacaca agccaggaag cacataagga catttcctac ctgtaccggt tcaactggaa    4080
ccactgcgga actatgacat cggaatgcaa acggcacttt atccaagaca cctgcctcta    4140
tgagtgttcc ccgaacttgg gaccctggat ccagcaggtg accagagct ggcgcaaaga    4200 gcggatcctt gatgttcccc tgtgcaaaga ggactgtcag cagtggtggg aggactgcca    4260
gagctctttt acctgcaaga gcaattggca aagggatgg aactggtcct cggggcataa    4320
cgagtgtcct gtgggagcct cctgccatcc cttcaccttc tacttcccca catctgctgc    4380
tctgtgtgag gaaatctgga gtcactccta caagctcagc aactacagtc gagggagcgg    4440
ccgctgcatt cagatgtggt tcgacccagc ccagggcaac cccaacgagg aagtggcgag    4500
gttctatgcc gaggccatga gtggagctgg gtttcatggg acctggccac tcttgtgcag    4560
cctgtcctta gtgctgctct gggtgatcag ctgaaaacta cgggctgcag gaattccgcc    4620
cccccccccc taacgttact ggccgaagcc gcttggaata aggccggtgt gcgtttgtct    4680
atatgttatt ttccaccata ttgccgtctt ttggcaatgt gagggcccgg aaacctggcc    4740
ctgtcttctt gacgagcatt cctagggtc tttcccctct cgccaaagga atgcaaggtc    4800
tgttgaatgt cgtgaaggaa gcagttcctc tggaagcttc ttgaagacaa caacgtctg    4860 tagcgaccct ttgcaggcag cggaaccccc cacctggcga caggtgcctc tgcggccaaa    4920
agccacgtgt ataagataca cctgcaaagg cggcacaacc ccagtgccac gttgtgagtt    4980
ggatagttgt ggaaagagtc aaatggctct cctcaagcgt attcaacaag ggctgaagg    5040 atgcccagaa ggtaccccat tgtatgggat ctgatctggg gcctcggtgc acatgcttta    5100
catgtgttta gtcgaggtta aaaacgtct aggcccccg aaccacgggg acgtggtttt    5160
cctttgaaaa acacgatgat aataccatgg tgagcaaggg cgaggagctg ttcaccgggg    5220
tggtgcccat cctggtcgag ctggacggcg acgtaaacgg ccacaagttc agcgtgtccg    5280
```

```
gcgagggcga gggcgatgcc acctacggca agctgaccct gaagttcatc tgcaccaccg    5340
gcaagctgcc cgtgccctgg cccaccctcg tgaccaccct gacctacggc gtgcagtgct    5400
tcagccgcta ccccgaccac atgaagcagc acgacttctt caagtccgcc atgcccgaag    5460
gctacgtcca ggagcgcacc atcttcttca aggacgacgg caactacaag acccgcgccg    5520
aggtgaagtt cgagggcgac accctggtga accgcatcga gctgaagggc atcgacttca    5580
aggaggacgg caacatcctg ggcacaagc tggagtacaa ctacaacagc cacaacgtct    5640
atatcatggc cgacaagcag aagaacggca tcaaggtgaa cttcaagatc cgccacaaca    5700
tcgaggacgg cagcgtgcag ctcgccgacc actaccagca gaacacccc atcggcgacg    5760
gccccgtgct gctgcccgac aaccactacc tgagcaccca gtccgccctg agcaaagacc    5820
ccaacgagaa gcgcgatcac atggtcctgc tggagttcgt gaccgccgcc gggatcactc    5880
tcggcatgga cgagctgtac aagtccggac tcagatctcg actagctagt agctagctag    5940
ctagtcgagc tcaagcttcg aattcgatat caagcttatc gcgataccgt cgacctcgag    6000
ggaattccga taatcaacct ctggattaca aaatttgtga agattgact ggtattctta    6060
actatgttgc tccttttacg ctatgtggat acgctgcttt aatgcctttg tatcatgcta    6120
ttgcttcccg tatggctttc attttctcct ccttgtataa atcctggttg ctgtctcttt    6180
atgaggagtt gtggcccgtt gtcaggcaac gtggcgtggt gtgcactgtg tttgctgacg    6240
caaccccac tggttgggc attgccacca cctgtcagct ccttccggg actttcgctt    6300
tccccctccc tattgccacg gcggaactca tcgccgcctg ccttgcccgc tgctggacag    6360
gggctcggct gttgggcact gacaattccg tggtgttgtc ggggaagctg acgtccttc    6420
catggctgct cgcctgtgtt gccacctgga ttctgcgcgg gacgtccttc tgctacgtcc    6480
cttcggccct caatccagcg gaccttcctt cccgcggcct gctgccggct ctgcggcctc    6540
ttccgcgtct tcgccttcgc cctcagacga gtcggatctc cctttgggcc gcctccccgc    6600
atcgggaatt cgagctcggt acctttaaga ccaatgactt acaaggcagc tgtagatctt    6660
agccacttt taaaagaaaa ggggggactg aagggctaa ttcactccca acgaagacaa    6720
gatgggatca attcaccatg gaataactt cgtatagcat acattatacg aagttatgct    6780
gctttttgct tgtactgggt ctctctggtt agaccagatc tgagcctggg agctctctgg    6840
ctaactaggg aacccactgc ttaagcctca ataaagcttg ccttgagtgc ttcaagtagt    6900
gtgtgcccgt ctgttgtgtg actctggtaa ctagagatcc ctcagaccct tttagtcagt    6960
gtggaaaatc tctagcagca tctagaatta attccgtgta ttctatagtg tcacctaaat    7020
cgtatgtgta tgatacataa ggttatgtat taattgtagc cgcgttctaa cgacaatatg    7080
tacaagccta attgtgtagc atctggctta ctgaagcaga ccctatcatc tctctcgtaa    7140
actgccgtca gagtcggttt ggttggacga accttctgag tttctggtaa cgccgtcccg    7200
cacccggaaa tggtcagcga accaatcagc agggtcatcg ctagccagat cctctacgcc    7260
ggacgcatcg tggccggcat caccggcgcc acaggtgcgg ttgctggcgc ctatatcgcc    7320
gacatcaccg atggggaaga tcgggctcgc cacttcgggc tcatgagcgc ttgtttcggc    7380
gtgggtatgg tggcaggccc cgtggccggg ggactgttgg gcgccatctc cttgcatgca    7440
ccattccttg cggcggcggt gctcaacggc ctcaacctac tactgggctg cttcctaatg    7500
caggagtcgc ataagggaga gcgtcgaatg gtgcactctc agtacaatct gctctgatgc    7560
cgcatagtta agccagcccc gacacccgcc aacacccgct gacgcgccct gacgggcttg    7620
tctgctcccg gcatccgctt acagacaagc tgtgaccgtc tccgggagct gcatgtgtca    7680
```

```
gaggttttca ccgtcatcac cgaaacgcgc gagacgaaag ggcctcgtga tacgcctatt    7740
tttataggtt aatgtcatga taataatggt ttcttagacg tcaggtggca cttttcgggg    7800
aaatgtgcgc ggaacccta tttgtttatt tttctaaata cattcaaata tgtatccgct    7860
catgagacaa taaccctgat aaatgcttca ataatattga aaaggaaga gtatgagtat    7920 tcaacatttc cgtgtcgccc ttattccctt ttttgcggca ttttgccttc ctgttttgc    7980 tcacccagaa acgctggtga agtaaaaga tgctgaagat cagttgggtg cacgagtggg    8040
ttacatcgaa ctggatctca acagcggtaa gatccttgag agttttcgcc ccgaagaacg    8100
ttttccaatg atgagcactt ttaaagttct gctatgtggc gcggtattat cccgtattga    8160
cgccgggcaa gagcaactcg gtcgccgcat acactattct cagaatgact tggttgagta    8220
ctcaccagtc acagaaaagc atcttacgga tggcatgaca gtaagagaat tatgcagtgc    8280
tgccataacc atgagtgata acactgcggc caacttactt ctgacaacga tcggaggacc    8340
gaaggagcta accgcttttt tgcacaacat gggggatcat gtaactcgcc ttgatcgttg    8400
ggaaccggag ctgaatgaag ccataccaaa cgacgagcgt gacaccacga tgcctgtagc    8460
aatggcaaca acgttgcgca aactattaac tggcgaacta cttactctag cttcccggca    8520
acaattaata gactggatgg aggcggataa agttgcagga ccacttctgc gctcggccct    8580
tccggctggc tggtttattg ctgataaatc tggagccggt gagcgtgggt ctcgcggtat    8640
cattgcagca ctggggccag atggtaagcc ctcccgtatc gtagttatct acacgacggg    8700
gagtcaggca actatggatg aacgaaatag acagatcgct gagataggtg cctcactgat    8760
taagcattgg taactgtcag accaagttta ctcatatata ctttagattg atttaaaact    8820
tcatttttaa tttaaaagga tctaggtgaa gatcctttt gataatctca tgaccaaaat    8880
cccttaacgt gagttttcgt tccactgagc gtcagacccc gtagaaaaga tcaaaggatc    8940
ttcttgagat cctttttttc tgcgcgtaat ctgctgcttg caaacaaaaa aaccaccgct    9000
accagcggtg gtttgtttgc cggatcaaga gctaccaact cttttccga aggtaactgg    9060 cttcagcaga gcgcagatac caaatactgt ccttctagtg tagccgtagt taggccacca    9120
cttcaagaac tctgtagcac cgcctacata cctcgctctg ctaatcctgt taccagtggc    9180
tgctgccagt ggcgataagt cgtgtcttac cgggttggac tcaagacgat agttaccgga    9240
taaggcgcag cggtcgggct gaacggggg ttcgtgcaca cagcccagct tggagcgaac    9300
gacctacacc gaactgagat acctacagcg tgagcattga gaaagcgcca cgcttcccga    9360
agggagaaag gcggacaggt atccggtaag cggcagggtc ggaacaggag agcgcacgag    9420
ggagcttcca gggggaaacg cctggtatct ttatagtcct gtcgggtttc gccacctctg    9480
acttgagcgt cgatttttgt gatgctcgtc agggggcgg agcctatgga aaaacgccag    9540
caacgcggcc ttttacggt tcctggcctt ttgctggcct tttgctcaca tgttctttcc    9600
tgcgttatcc cctgattctg tggataaccg tattaccgcc tttgagtgag ctgataccgc    9660
tcgccgcagc cgaacgaccg agcgcagcga gtcagtgagc gaggaagcgg aagagcgccc    9720
aatacgcaaa ccgcctctcc ccgcgcgttg gccgattcat taatgcagct gtggaatgtg    9780
tgtcagttag ggtgtggaaa gtccccaggc tccccagcag gcagaagtat gcaaagcatg    9840
catctcaatt agtcagcaac caggtgtgga aagtccccag gctccccagc aggcagaagt    9900
atgcaaagca tgcatctcaa ttagtcagca accatagtcc cgcccctaac tccgcccatc    9960
ccgcccctaa ctccgcccag ttccgcccat tctccgcccc atggctgact aatttttttt    10020
```

```
atttatgcag aggccgaggc cgcctcggcc tctgagctat tccagaagta gtgaggaggc    10080
ttttttggag gcctaggctt ttgcaaaaag cttggacaca agacaggctt gcgagatatg    10140
tttgagaata ccactttatc ccgcgtcagg gagaggcagt gcgtaaaaag acgcggactc    10200
atgtgaaata ctggttttta gtgcgccaga tctctataat ctcgcgcaac ctattttccc    10260
ctcgaacact ttttaagccg tagataaaca ggctgggaca cttcacatga gcgaaaaata    10320
catcgtcacc tgggacatgt tgcagatcca tgcacgtaaa ctcgcaagcc gactgatgcc    10380
ttctgaacaa tggaaaggca ttattgccgt aagccgtggc ggtctgtacc gggtgcgtta    10440
ctggcgcgtg aactgggtat tcgtcatgtc gataccgttt gtatttccag ctacgatcac    10500
gacaaccagc gcgagcttaa agtgctgaaa cgcgcagaag gcgatggcga aggcttcatc    10560
gttattgatg acctggtgga taccggtggt actgcgttg cgattcgtga aatgtatcca    10620
aaagcgcact ttgtcaccat cttcgcaaaa ccggctggtc gtccgctggt tgatgactat    10680
gttgttgata tcccgcaaga tacctggatt gaacagccgt gggatatggg cgtcgtattc    10740
gtcccgccaa tctccggtcg ctaatctttt caacgcctgg cactgccggg cgttgttctt    10800
tttaacttca ggcgggttac aatagtttcc agtaagtatt ctggaggctg catccatgac    10860
acaggcaaac ctgagcgaaa ccctgttcaa accccgcttt aaacatcctg aaacctcgac    10920
gctagtccgc cgctttaatc acggcgcaca accgcctgtg cagtcggccc ttgatggtaa    10980
aaccatccct cactggtatc gcatgattaa ccgtctgatg tggatctggc gcggcattga    11040
cccacgcgaa atcctcgacg tccaggcacg tattgtgatg agcgatgccg aacgtaccga    11100
cgatgattta tacgatacgg tgattggcta ccgtggcggc aactggattt atgagtgggc    11160
cccggatctt tgtgaaggaa ccttacttct gtggtgtgac ataattggac aaactaccta    11220
cagagattta aagctctaag gtaaatataa aattttttaag tgtataatgt gttaaactac    11280
tgattctaat tgtttgtgta tttagattc caacctatgg aactgatgaa tgggagcagt    11340
ggtggaatgc cttaatgag gaaaacctgt tttgctcaga agaaatgcca tctagtgatg    11400
atgaggctac tgctgactct caacattcta ctcctccaaa aaagaagaga aaggtagaag    11460
accccaagga ctttccttca gaattgctaa gttttttgag tcatgctgtg tttagtaata    11520
gaactcttgc ttgctttgct atttacacca caaaggaaaa agctgcactg ctatacaaga    11580
aaattatgga aaaatattct gtaacctta taagtaggca taacagttat aatcataaca    11640
tactgttttt tcttactcca cacaggcata gagtgtctgc tattaataac tatgctcaaa    11700
aattgtgtac cttagctttt ttaatttgta aaggggttaa taaggaatat ttgatgtata    11760
gtgccttgac tagagatcat aatcagccat accacatttg tagaggtttt acttgcttta    11820
aaaaacctcc cacacctccc cctgaacctg aaacataaaa tgaatgcaat tgttgttgtt    11880
aacttgtttta ttgcagctta taatggttac aaataaagca atagcatcac aaatttcaca    11940
aataaagcat ttttttcact gcattctagt tgtggtttgt ccaaactcat caatgtatct    12000
tatcatgtct ggatcaactg gataactcaa gctaaccaaa atcatcccaa acttcccacc    12060
ccatacccta ttaccactgc caattaccta gtggtttcat ttactctaaa cctgtgattc    12120
ctctgaatta ttttcatttt aaagaaattg tatttgttaa atatgtacta caaacttagt    12180
ag                                                                  12182
```

<210> SEQ ID NO 9
<211> LENGTH: 10447
<212> TYPE: DNA
<213> ORGANISM: Artificial Sequence
<220> FEATURE:
<223> OTHER INFORMATION: A synthetic pHR EcorI hAnti cd19 1D3 myc hinge
      cd28 cd3zeta

<400> SEQUENCE: 9

| | | | | | |
|---|---|---|---|---|---|
| cgataccgtc | gaccaaggca | gctgtagatc | ttagccactt | tttaaaagaa | aagggggac | 60 |
| tggaagggct | aattcactcc | caacgaagac | aagatctgct | ttttgcttgt | actgggtctc | 120 |
| tctggttaga | ccagatctga | gcctgggagc | tctctggcta | actagggaac | ccactgctta | 180 |
| agcctcaata | aagcttgcct | tgagtgcttc | aagtagtgtg | tgcccgtctg | ttgtgtgact | 240 |
| ctggtaacta | gagatccctc | agacccttt | agtcagtgtg | gaaaatctct | agcagcatct | 300 |
| agaattaatt | ccgtgtattc | tatagtgtca | cctaaatcgt | atgtgtatga | tacataaggt | 360 |
| tatgtattaa | ttgtagccgc | gttctaacga | caatatgtac | aagcctaatt | gtgtagcatc | 420 |
| tggcttactg | aagcagaccc | tatcatctct | ctcgtaaact | gccgtcagag | tcggtttggt | 480 |
| tggacgaacc | ttctgagttt | ctggtaacgc | cgtcccgcac | ccggaaatgg | tcagcgaacc | 540 |
| aatcagcagg | gtcatcgcta | gccagatcct | ctacgccgga | cgcatcgtgg | ccggcatcac | 600 |
| cggcgccaca | ggtgcggttg | ctggcgccta | tatcgccgac | atcaccgatg | gggaagatcg | 660 |
| ggctcgccac | ttcgggctca | tgagcgcttg | tttcggcgtg | gtatggtgg | caggccccgt | 720 |
| ggccggggga | ctgttgggcg | ccatctcctt | gcatgcacca | ttccttgcgg | cggcggtgct | 780 |
| caacggcctc | aacctactac | tgggctgctt | cctaatgcag | gagtcgcata | agggagagcg | 840 |
| tcgaatggtg | cactctcagt | acaatctagc | tctgatgccg | catagttaag | ccagccccga | 900 |
| cacccgccaa | cacccgctga | cgcgccctga | cgggcttgtc | tgctcccggc | atccgcttac | 960 |
| agacaagctg | tgaccgtctc | cgggagctgc | atgtgtcaga | ggttttcacc | gtcatcaccg | 1020 |
| aaacgcgcga | gacgaaaggg | cctcgtgata | cgcctatttt | tataggttaa | tgtcatgata | 1080 |
| ataatggttt | cttagacgtc | aggtggcact | tttcgggaa | atgtgcgcgg | aaccccctatt | 1140 |
| tgtttatttt | tctaaataca | ttcaaatatg | tatccgctca | tgagacaata | accctgataa | 1200 |
| atgcttcaat | aatattgaaa | aaggaagagt | atgagtattc | aacatttccg | tgtcgccctt | 1260 |
| attccctttt | ttgcggcatt | ttgccttcct | gtttttgctc | acccagaaac | gctggtgaaa | 1320 |
| gtaaaagatg | ctgaagatca | gttgggtgca | cgagtgggtt | acatcgaact | ggatctcaac | 1380 |
| agcggtaaga | tccttgagag | ttttcgcccc | gaagaacgtt | ttccaatgat | gagcactttt | 1440 |
| aaagttctgc | tatgtggcgc | ggtattatcc | cgtattgacg | ccgggcaaga | gcaactcggt | 1500 |
| cgccgcatac | actattctca | gaatgacttg | gttgagtact | caccagtcac | agaaaagcat | 1560 |
| cttacggatg | gcatgacagt | aagagaatta | tgcagtgctg | ccataaccat | gagtgataac | 1620 |
| actgcggcca | acttacttct | gacaacgatc | ggaggaccga | aggagctaac | cgcttttttg | 1680 |
| cacaacatgg | gggatcatgt | aactcgcctt | gatcgttggg | aaccggagct | gaatgaagcc | 1740 |
| ataccaaacg | acgagcgtga | caccacgatg | cctgtagcaa | tggcaacaac | gttgcgcaaa | 1800 |
| ctattaactg | gcgaactact | tactctagct | tcccggcaac | aattaataga | ctggatggag | 1860 |
| gcggataaag | ttgcaggacc | acttctgcgc | tcggcccttc | cggctggctg | gtttattgct | 1920 |
| gataaatctg | gagccggtga | gcgtgggtct | cgcggtatca | ttgcagcact | ggggccagat | 1980 |
| ggtaagccct | cccgtatcgt | agttatctac | acgacgggga | gtcaggcaac | tatggatgaa | 2040 |
| cgaaatagac | agatcgctga | gataggtgcc | tcactgatta | agcattggta | actgtcagac | 2100 |
| caagtttact | catatatact | ttagattgat | ttaaaacttc | atttttaatt | taaaaggatc | 2160 |
| taggtgaaga | tccttttga | taatctcatg | accaaaatcc | cttaacgtga | gttttcgttc | 2220 |

```
cactgagcgt cagaccccgt agaaaagatc aaaggatctt cttgagatcc ttttttctg    2280
cgcgtaatct gctgcttgca acaaaaaaa ccaccgctac cagcggtggt ttgtttgccg    2340
gatcaagagc taccaactct ttttccgaag gtaactggct tcagcagagc gcagatacca   2400
aatactgtcc ttctagtgta gccgtagtta ggccaccact tcaagaactc tgtagcaccg   2460
cctacatacc tcgctctgct aatcctgtta ccagtggctg ctgccagtgg cgataagtcg   2520
tgtcttaccg ggttggactc aagacgatag ttaccggata aggcgcagcg gtcgggctga   2580
acgggggggtt cgtgcacaca gcccagcttg gagcgaacga cctacaccga actgagatac   2640
ctacagcgtg agctatgaga aagcgccacg cttcccgaag ggagaaaggc ggacaggtat   2700
ccggtaagcg gcagggtcgg aacaggagag cgcacgaggg agcttccagg gggaaacgcc   2760
tggtatcttt atagtcctgt cgggtttcgc cacctctgac ttgagcgtcg attttttgtga   2820
tgctcgtcag gggggcggag cctatggaaa aacgccagca acgcggcctt tttacggttc   2880
ctggcctttt gctggccttt tgctcacatg ttctttcctg cgttatcccc tgattctgtg   2940
gataaccgta ttaccgcctt tgagtgagct gataccgctc gccgcagccg aacgaccgag   3000
cgcagcgagt cagtgagcga ggaagcggaa gagcgcccaa tacgcaaacc gcctctcccc   3060
gcgcgttggc cgattcatta atgcagctgt ggaatgtgtg tcagttaggg tgtggaaagt   3120
ccccaggctc cccagcaggc agaagtatgc aaagcatgca tctcaattag tcagcaacca   3180
ggtgtggaaa gtccccaggc tccccagcag gcagaagtat gcaaagcatg catctcaatt   3240
agtcagcaac catagtcccg cccctaactc cgcccatccc gcccctaact ccgcccagtt   3300
ccgcccattc tccgccccat ggctgactaa ttttttttat ttatgcagag gccgaggccg   3360
cctcggcctc tgagctattc cagaagtagt gaggaggctt ttttggaggc ctaggctttt   3420
gcaaaaagct tggacacaag acaggcttgc gagatatgtt tgagaatacc actttatccc   3480
gcgtcaggga gaggcagtgc gtaaaaagac gcggactcat gtgaaatact ggtttttagt   3540
gcgccagatc tctataatct cgcgcaacct attttcccct cgaacacttt ttaagccgta   3600
gataaacagg ctgggacact tcacatgagc gaaaaataca tcgtcacctg ggacatgttg   3660
cagatccatg cacgtaaact cgcaagccga ctgatgcctt ctgaacaatg gaaaggcatt   3720
attgccgtaa gccgtggcgg tctgtaccgg gtgcgttact ggcgcgtgaa ctgggtattc   3780
gtcatgtcga taccgtttgt atttccagct acgatcacga caaccagcgc gagcttaaag   3840
tgctgaaacg cgcagaaggc gatggcgaag gcttcatcgt tattgatgac ctggtggata   3900
ccggtggtac tgcggttgcg attcgtgaaa tgtatccaaa agcgcacttt gtcaccatct   3960
tcgcaaaacc ggctggtcgt ccgctggttg atgactatgt tgttgatatc ccgcaagata   4020
cctgattga acagcgtgg gatatgggcg tcgtattcgt cccgccaatc tccggtcgct   4080
aatcttttca acgcctggca ctgccgggcg ttgttctttt taacttcagg cgggttacaa   4140
tagttttccag taagtattct ggaggctgca tccatgacac aggcaaacct gagcgaaacc   4200
ctgttcaaac cccgctttaa acatcctgaa acctcgacgc tagtccgccg ctttaatcac   4260
ggcgcacaac cgcctgtgca gtcggccctt gatggtaaaa ccatccctca ctggtatcgc   4320
atgattaacc gtctgatgtg gatctggcgc ggcattgacc cacgcgaaat cctcgacgtc   4380
caggcacgta ttgtgatgag cgatgccgaa cgtaccgacg atgatttata cgatacggtg   4440
attggctacc gtgcgcggcaa ctggatttat gagtgggccc cggatctttg tgaaggaacc   4500
ttacttctgt ggtgtgacat aattggacaa actacctaca gagatttaaa gctctaaggt   4560
```

```
aaatataaaa ttttaagtg tataatgtgt taaactactg attctaattg tttgtgtatt    4620
ttagattcca acctatggaa ctgatgaatg ggagcagtgg tggaatgcct ttaatgagga    4680
aaacctgttt tgctcagaag aaatgccatc tagtgatgat gaggctactg ctgactctca    4740
acattctact cctccaaaaa agaagagaaa ggtagaagac cccaaggact ttccttcaga    4800
attgctaagt tttttgagtc atgctgtgtt tagtaataga actcttgctt gctttgctat    4860
ttacaccaca aaggaaaaag ctgcactgct atacaagaaa attatggaaa aatattctgt    4920
aacctttata agtaggcata acagttataa tcataacata ctgttttttc ttactccaca    4980
caggcataga gtgtctgcta ttaataacta tgctcaaaaa ttgtgtacct ttagcttttt    5040
aatttgtaaa ggggttaata aggaatattt gatgtatagt gccttgacta gagatcataa    5100
tcagccatac cacatttgta gaggttttac ttgctttaaa aaacctccca cacctcccccc    5160 tgaacctgaa acataaaatg aatgcaattg ttgttgttaa cttgtttatt gcagcttata    5220
atggttacaa ataaagcaat agcatcacaa atttcacaaa taaagcattt ttttcactgc    5280
attctagttg tggtttgtcc aaactcatca atgtatctta tcatgtctgg atcaactgga    5340
taactcaagc taaccaaaat catcccaaac ttcccacccc atccctatt accactgcca    5400 attacctagt ggtttcattt actctaaacc tgtgattcct ctgaattatt ttcattttaa    5460
agaaattgta tttgttaaat atgtactaca aacttagtag ttggaagggc taattcactc    5520
ccaaagaaga caagatatcc ttgatctgtg gatctaccac acacaaggct acttccctga    5580
ttagcagaac tacacaccag ggccaggggt cagatatcca ctgacctttg gatggtgcta    5640
caagctagta ccagttgagc cagataaggt agaagaggcc aataaaggag agaacaccag    5700
cttgttacac cctgtgagcc tgcatgggat ggatgacccg gagagagaag tgttagagtg    5760
gaggtttgac agccgcctag catttcatca cgtggcccga gagctgcatc cggagtactt    5820
caagaactgc tgatatcgag cttgctacaa gggactttcc gctggggact ttccagggag    5880
gcgtggcctg ggcgggactg gggagtggcg agccctcaga tcctgcatat aagcagctgc    5940 ttttttgcctg tactgggtct ctctggttag accagatctg agcctgggag ctctctggct    6000
aactagggaa cccactgctt aagcctcaat aaagcttgcc ttgagtgctt caagtagtgt    6060
gtgcccgtct gttgtgtgac tctggtaact agagatccct cagacccttt tagtcagtgt    6120
ggaaaatctc tagcagtggc gcccgaacag ggacttgaaa gcgaaaggga accagagga    6180 gctctctcga cgcaggactc ggcttgctga gcgcgcacg gcaagaggcg aggggcggcg    6240
actggtgagt acgccaaaaa ttttgactag cggaggctag aaggagagag atgggtgcga    6300
gagcgtcagt attaagcggg ggagaattag atcgcgatgg gaaaaaattc ggttaaggcc    6360 aggggggaaag aaaaaatata aattaaaaca tatagtatgg gcaagcaggg agctagaacg    6420
attcgcagtt aatcctggcc tgttagaaac atcagaaggc tgtagacaaa tactgggaca    6480
gctacaacca tcccttcaga caggatcaga agaacttaga tcattatata atacagtagc    6540
aaccctctat tgtgtgcatc aaaggataga gataaaagac accaaggaag ctttagacaa    6600
gatagaggaa gagcaaaaca aaagtaagac caccgcacag caagcggccg gtgatcttca    6660
gacctggacg atatatatga gggacaattg gagaagtgaa ttatataaat ataaagtagt    6720
aaaaattgaa ccattaggag tagcacccac caaggcaaag agaagagtgg tgcagagaga    6780
aaaaagagca gtgggaatag gagctttgtt ccttgggttc ttgggagcag caggaagcac    6840
tatgggcgca gcgtcaatga cgctgacggt acaggccaga caattattgt ctggtatagt    6900
gcagcagcag aacaatttgc tgagggctat tgaggcgcaa cagcatctgt tgcaactcac    6960
```

-continued

| | |
|---|---|
| agtctgggc atcaagcagc tccaggcaag aatcctggct gtggaaagat acctaaagga | 7020 |
| tcaacagctc ctggggattt gggttgctc tggaaaactc atttgcacca ctgctgtgcc | 7080 |
| ttggaatgct agttggagta ataaatctct ggaacagatt tggaatcaca cgacctggat | 7140 |
| ggagtgggac agagaaatta acaattacac aagcttaata cactccttaa ttgaagaatc | 7200 |
| gcaaaaccag caagaaaaga atgaacaaga attattggaa ttagataaat gggcaagttt | 7260 |
| gtggaattgg tttaacataa caattggct gtggtatata aaattattca taatgatagt | 7320 |
| aggaggcttg gtaggtttaa gaatagtttt tgctgtactt tctatagtga atagagttag | 7380 |
| gcagggatat tcaccattat cgtttcagac ccacctccca accccgaggg gacccgacag | 7440 |
| gccccgaagga atagaagaag aaggtggaga gagagacaga gacagatcca ttcgattagt | 7500 |
| gaacggatct cgacggtcgc caaatggcag tattcatcca caattttaaa agaaaagggg | 7560 |
| ggattggggg gtacagtgca ggggaaagaa tagtagacat aatagcaaca gacatacaaa | 7620 |
| ctaaagaatt acaaaaacaa attacaaaaa ttcaaaattt tcgggtttat tacagggaca | 7680 |
| gcagagatcc agtttggatc gataagcttg atatcgaatt gggtagggga ggcgcttttc | 7740 |
| ccaaggcagt ctggagcatg cgctttagca gccccgctgg gcacttggcg ctacacaagt | 7800 |
| ggcctctggc ctcgcacaca ttccacatcc accggtaggc gccaaccggc tccgttcttt | 7860 |
| ggtggcccct tcgcgccacc ttctactcct cccctagtca ggaagttccc ccccgccccg | 7920 |
| cagctcgcgt cgtgcaggac gtgacaaatg gaagtagcac gtctcactag tctcgtgcag | 7980 |
| atggacagca ccgctgagca atggaagcgg gtaggccttt ggggcagcgg ccaatagcag | 8040 |
| ctttgctcct tcgctttctg ggctcagagg ctgggaaggg gtgggtccgg gggcgggctc | 8100 |
| aggggcgggc tcaggggcgg ggcgggcgcc cgaaggtcct ccggaggccc ggcattctgc | 8160 |
| acgcttcaaa agcgcacgtc tgccgcgctg ttctcctctt cctcatctcc gggcctttcg | 8220 |
| atggctcttc cagtgactgc tcttctcctc ccgcttgcgc tgctgttgca tgcggctcgg | 8280 |
| ccggagcaaa agctgatttc agaagaggac ttggatatcc agatgacaca gaccacttca | 8340 |
| tctctttctg ctagcctggg ggatcgggtc acaataagct gtcgcgcatc ccaagacata | 8400 |
| agcaaatatc tgaattggta tcaacagaaa cccgatggaa ctgtgaaact tctcatctac | 8460 |
| catacgagca gactgcattc tggggttcct agccgctttt cagggtctgg atctggaacg | 8520 |
| gactattcac ttaccatatc taatttggaa caagaagaca tcgcgaccta tttctgtcag | 8580 |
| caaggcaata cgctccctta ctcttttgga gggggaacga agttggagat cacaggtgga | 8640 |
| ggcggcagtg gcggggagg atctggtgga ggtggttctg aggtcaagct gcaggagagt | 8700 |
| ggtcccggc tggtagcccc gagccagagt ctgtctgtta cttgcactgt gtcaggcgtg | 8760 |
| agtctcccag actatggtgt atcatggatt cgacagccgc cccggaaagg acttgagtgg | 8820 |
| ctcggagtga tctggggatc cgaaacgacg tactacaata gcgcgctcaa aagccggctg | 8880 |
| accatcatta aggataactc taaaagccag gtgttcttga aaatgaattc cttgcagaca | 8940 |
| gatgatacgg cgatctatta ctgtgccaag cactactact atggaggcag ctatgccatg | 9000 |
| gattattggg gtcaaggcac ttctgtgaca gtgagcagtg ccgcagctat tgaagtgatg | 9060 |
| tacccgcctc cgtatcttga taatgagaaa tctaacggaa ccataataca cgtgaaaggc | 9120 |
| aaacatttgt gtccgtctcc tctgttcccc gggcctagta aaccgttttg ggtactggtg | 9180 |
| gtggtaggcg gagtacttgc atgttactca ctcctcgtta ccgtcgcatt cattatcttc | 9240 |
| tgggtacgga gcaagagatc tcggctgctt catagcgatt atatgaatat gacacccaga | 9300 |

```
cgcccaggtc ctactaggaa acattaccag ccgtatgcgc cgccgaggga cttcgccgca    9360
tacagatctc gcgtgaagtt ctcaagatct gccgatgcac cggcttatca gcagggacaa    9420
aaccaactgt ataatgagct gaacctgggg cggagggagg agtatgatgt cctggacaag    9480
cgaagagggc gagaccccga aatgggaggc aagcctcaac ggcggaagaa cccacaagag    9540
ggcctgtata acgagcttca aaaggacaaa atggcggaag cgtatagcga gatcggaatg    9600
aagggcgaac gaaggagagg gaaaggtcac gatgggctct accaggggct cagcacggca    9660
acaaaagaca catatgacgc attgcatatg caggcgctgc caccgagatg actcacgcgt    9720
caagtggagc aaggcaggtg gacagtggat ccttgacttg cggccgcaac tcccacctgc    9780
aacatgcgtg actgactgag gccgcgactc tagagtcgac ctgcaggcat gcaagcttga    9840
tatcaagctt atcgataatc aacctctgga ttacaaaatt tgtgaaagat tgactggtat    9900
tcttaactat gttgctcctt ttacgctatg tggatacgct gctttaatgc ctttgtatca    9960
tgctattgct tcccgtatgg ctttcatttt ctcctccttg tataaatcct ggttgctgtc   10020
tctttatgag gagttgtggc ccgttgtcag gcaacgtggc gtggtgtgca ctgtgtttgc   10080
tgacgcaacc cccactggtt ggggcattgc caccacctgt cagctccttt ccgggacttt   10140
cgctttcccc ctccctattg ccacggcgga actcatcgcc gcctgccttg cccgctgctg   10200
gacaggggct cggctgttgg gcactgacaa ttccgtggtg ttgtcgggga atcatcgtc   10260
cttccttgg ctgctcgcct gtgttgccac ctggattctg cgcgggacgt ccttctgcta   10320
cgtcccttcg gccctcaatc cagcggacct tccttcccgc ggcctgctgc cggctctgcg   10380
gcctcttccg cgtcttcgcc ttcgccctca gacgagtcgg atctcccttt gggccgcctc   10440
cccgcat                                                              10447
```

<210> SEQ ID NO 10
<211> LENGTH: 12536
<212> TYPE: DNA
<213> ORGANISM: Artificial Sequence
<220> FEATURE:
<223> OTHER INFORMATION: A synthetic pWPI pmei mAnti cd19 1D3 myc hinge cd28 cd3zeta

<400> SEQUENCE: 10

```
ttggaagggc taattcactc ccaaagaaga caagatatcc ttgatctgtg gatctaccac      60
acacaaggct acttccctga ttagcagaac tacacaccag ggccagggt cagatatcca     120
ctgacctttg gatggtgcta caagctagta ccagttgagc cagataaggt agaagaggcc     180
aataaaggag agaacaccag cttgttacac cctgtgagcc tgcatgggat ggatgacccg     240
gagagagaag tgttagagtg gaggtttgac agccgcctag catttcatca cgtggcccga     300
gagctgcatc cggagtactt caagaactgc tgatatcgag cttgctacaa gggactttcc     360
gctggggact ttccagggag gcgtggcctg ggcgggactg gggagtggcg agccctcaga     420
tcctgcatat aagcagctgc tttttgcctg tactgggtct ctctggttag accagatctg     480
agcctgggag ctctctggct aactagggaa cccactgctt aagcctcaat aaagcttgcc     540
ttgagtgctt caagtagtgt gtgcccgtct gttgtgtgac tctggtaact agagatccct     600
cagacccttt tagtcagtgt ggaaaatctc tagcagtggc gcccgaacag ggacttgaaa     660
gcgaaaggga accagagga gctctctcga cgcaggactc ggcttgctga agcgcgcacg     720
gcaagaggcg aggggcggcg actggtgagt acgccaaaaa ttttgactag cggaggctag     780
aaggagagag atgggtgcga gagcgtcagt attaagcggg ggagaattag atcgcgatgg     840
```

```
gaaaaaattc ggttaaggcc aggggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg ctgatcttca gacctggagg aggagatatg agggacaatt ggagaagtga   1200
attatataaa tataaagtag taaaaattga accattagga gtagcaccca ccaaggcaaa   1260
gagaagagtg gtgcagagag aaaaaagagc agtgggaata ggagctttgt tccttgggtt   1320
cttgggagca gcaggaagca ctatgggcgc agcgtcaatg acgctgacgg tacaggccag   1380
acaattattg tctggtatag tgcagcagca gaacaatttg ctgagggcta ttgaggcgca   1440
acagcatctg ttgcaactca cagtctgggg catcaagcag ctccaggcaa gaatcctggc   1500
tgtggaaaga tacctaaagg atcaacagct cctggggatt tggggttgct ctggaaaact   1560
catttgcacc actgctgtgc cttggaatgc tagttggagt aataaatctc tggaacagat   1620
ttggaatcac acgacctgga tggagtggga cagagaaatt aacaattaca caagcttaat   1680
acactcctta attgaagaat cgcaaaacca gcaagaaaag aatgaacaag aattattgga   1740
attagataaa tgggcaagtt tgtggaattg gtttaacata acaaattggc tgtggtatat   1800
aaaattattc ataatgatag taggaggctt ggtaggttta agaatagttt ttgctgtact   1860
ttctatagtg aatagagtta ggcagggata ttcaccatta tcgtttcaga cccacctccc   1920
aaccccgagg ggacccgaca ggcccgaagg aatagaagaa gaaggtggag agagagacag   1980
agacagatcc attcgattag tgaacggatc tcgacggtat cgatgtcgac gataagcttt   2040
gcaaagatgg ataaagtttt aaacagagag gaatctttgc agctaatgga ccttctaggt   2100
cttgaaagga gtgggaattg gctccggtgc ccgtcagtgg gcagagcgca catcgcccac   2160
agtccccgag aagttggggg gaggggtcgg caattgaacc ggtgcctaga gaaggtggcg   2220
cggggtaaac tgggaaagtg atgtcgtgta ctggctccgc cttttttccg agggtggggg   2280
agaaccgtat ataagtgcag tagtcgccgt gaacgttctt tttcgcaacg ggtttgccgc   2340
cagaacacag gtaagtgccg tgtgtggttc ccgcgggcct ggcctcttta cgggttatgg   2400
cccttgcgtg ccttgaatta cttccactgg ctgcagtacg tgattcttga tcccgagctt   2460
cgggttggaa gtgggtggga gagttcgagg ccttgcgctt aaggagcccc ttcgcctcgt   2520
gcttgagttg aggcctggcc tgggcgctgg ggccgccgcg tgcgaatctg gtggcacctt   2580
cgcgcctgtc tcgctgcttt cgataagtct ctagccattt aaaattttg atgacctgct   2640 gcgacgcttt ttttctggca agatagtctt gtaaatgcgg gccaagatct gcacactggt   2700
atttcggttt ttggggccgc gggcggcgac ggggcccgtg cgtcccagcg cacatgttcg   2760
gcgaggcggg gcctgcgagc gcggccaccg agaatcggac gggggtagtc tcaagctggc   2820
cggcctgctc tggtgcctgg cctcgcgccg ccgtgtatcg ccccgccctg gcggcaagg   2880 ctggcccggt cggcaccagt tgcgtgagcg gaaagatggc cgcttccggg ccctgctgca   2940
gggagctcaa aatggaggac gcggcgctcg ggagagcggg cgggtgagtc acccacacaa   3000
aggaaaaggg cctttccgtc ctcagccgtc gcttcatgtg actccacgga gtaccgggcg   3060
ccgtccaggc acctcgatta gttctcgagc ttttggagta cgtcgtcttt aggttggggg   3120 gagggggtttt atgcgatgga gtttcccccac actgagtggg tggagactga agttaggcca   3180
gcttggcact tgatgtaatt ctccttggaa tttgcccttt ttgagtttgg atcttggttc   3240
```

```
attctcaagc ctcagacagt ggttcaaagt ttttttcttc catttcaggt gtcgtgagga    3300
atttcgacat ttaaatttaa ttaatctcga cggtatcggt taacttttaa aagaaaaggg    3360
gggattgggg ggtacagtgc aggggaaaga atagtagaca taatagcaac agacatacaa    3420
actaaagaat tacaaaaaca aattacaaaa attcaaaatt ttatcgatca cgagactagc    3480
ctcgaggttt atgggggttc ccacccagct gttgggttg ctgctcctct ggatcactga    3540
tgccatctgc gaacagaagc tcatttctga agaagatctg gacatacaga tgacccagag    3600
tcctgccagc ttgtccacat ccctcggaga gaccgtgaca attcaatgcc aggcctctga    3660
ggacatatat tctggattgg cttggtacca gcaaaagcca ggtaaaagtc ctcagttgtt    3720
gatatacggc gcttctgatt tgcaagacgg ggtgccctca cgatttagcg ggtctggaag    3780
tggcactcag tacagtctga agattacttc aatgcaaaca gaagacgagg gtgtgtattt    3840
ttgccaacag gggctgacct acccaaggac attcggggc ggtacaaagc ttgaacttaa    3900
gggcggcggt gggtctggag gtggtggatc tggcggaggg ggaagtgagg tacagctgca    3960
acagtccggc gccgaactcg ttcgccctgg aacctcagtc aaattgtcat gcaaggtgag    4020
tggcgacaca ataacctttt actatatgca cttcgttaaa cagaggccag gtcaaggtct    4080
ggaatggata ggcagaattg atccagaaga tgagtccacc aaatactcag aaaagttcaa    4140
aaacaaagcc actcttactg ccgacacctc aagcaacaca gcatatctta agctcagttc    4200
acttaccagc gaagacaccg ccacctattt ttgtatttat ggtggctatt actttgacta    4260
ctgggggcaa ggtgttatgg taacagtttc ttccattgaa ttcatgtatc cacccccta    4320
tttggataat gaacgatcta atgggactat aatacatatc aaggaaaagc atctgtgtca    4380
tacccaaagt tcccctaagc ttttctgggc cctcgtcgtt gtggcaggag tgcttttttg    4440
ctatggattg ttggttactg tggctctctg cgtcatttgg acaaatagta ggaggaatcg    4500
gggggacaa tctgattaca tgaacatgac accacggagg ccaggcctta ccagaaagcc    4560
ctaccaacct tatgcaccag cacgagactt cgccgcatac aggccaaggg ctaagttttc    4620
ccgcagcgcc gaaaccgcag ccaacctcca agatcctaat cagctctata cgaattgaa    4680
tcttggccgc agagaggagt acgacgtact tgagaaaaag agagctaggg accctgaaat    4740
gggtgggaag caacagcgaa gaaggaaccc acaggaaggg gtgtataatg cccttcaaaa    4800
ggataaaatg gcagaggcat acagtgaaat cggaaccaag gggagagac gcagagggaa    4860
aggccatgac ggcctttatc agggtttgtc aactgctact aaagacactt atgatgcctt    4920
gcatatgcaa actctcgcac ccagatgaaa actacgggct gcaggaattc cgccccccc    4980
cccctaacgt tactggccga agccgcttgg aataaggccg gtgtgcgttt gtctatatgt    5040
tattttccac catattgccg tcttttggca atgtgagggc ccggaaacct ggccctgtct    5100
tcttgacgag cattcctagg ggtctttccc ctctcgccaa aggaatgcaa ggtctgttga    5160
atgtcgtgaa ggaagcagtt cctctggaag cttcttgaag acaacaacg tctgtagcga    5220
ccctttgcag gcagcggaac cccccacctg gcgacaggtg cctctgcggc caaaagccac    5280
gtgtataaga tacacctgca aaggcggcac aaccccagtg ccacgttgtg agttggatag    5340
ttgtggaaag agtcaaatgg ctctcctcaa gcgtattcaa caagggctg aaggatgccc    5400
agaaggtacc ccattgtatg ggatctgatc tggggcctcg gtgcacatgc tttacatgtg    5460
tttagtcgag gttaaaaaac gtctaggccc ccgaaccac ggggacgtgg ttttcctttg    5520
aaaaacacga tgataatacc atggtgagca agggcgagga gctgttcacc ggggtggtgc    5580
```

```
ccatcctggt cgagctggac ggcgacgtaa acggccacaa gttcagcgtg tccggcgagg      5640
gcgagggcga tgccacctac ggcaagctga ccctgaagtt catctgcacc accggcaagc      5700
tgcccgtgcc ctggcccacc ctcgtgacca ccctgaccta cggcgtgcag tgcttcagcc      5760
gctaccccga ccacatgaag cagcacgact tcttcaagtc cgccatgccc gaaggctacg      5820
tccaggagcg caccatcttc ttcaaggacg acggcaacta caagacccgc gccgaggtga      5880
agttcgaggg cgacaccctg gtgaaccgca tcgagctgaa gggcatcgac ttcaaggagg      5940
acggcaacat cctggggcac aagctggagt acaactacaa cagccacaac gtctatatca      6000
tggccgacaa gcagaagaac ggcatcaagg tgaacttcaa gatccgccac aacatcgagg      6060
acggcagcgt gcagctcgcc gaccactacc agcagaacac ccccatcggc gacggccccg      6120
tgctgctgcc cgacaaccac tacctgagca cccagtccgc cctgagcaaa gaccccaacg      6180
agaagcgcga tcacatggtc ctgctggagt tcgtgaccgc cgccgggatc actctcggca      6240
tggacgagct gtacaagtcc ggactcagat ctcgactagc tagtagctag ctagctagtc      6300
gagctcaagc ttcgaattcg atatcaagct tatcgcgata ccgtcgacct cgagggaatt      6360
ccgataatca acctctggat tacaaaattt gtgaaagatt gactggtatt cttaactatg      6420
ttgctccttt tacgctatgt ggatacgctg ctttaatgcc tttgtatcat gctattgctt      6480
cccgtatggc tttcattttc tcctccttgt ataaatcctg gttgctgtct ctttatgagg      6540
agttgtggcc cgttgtcagg caacgtggcg tggtgtgcac tgtgtttgct gacgcaaccc      6600
ccactggttg gggcattgcc accacctgtc agctcctttc cgggactttc gctttccccc      6660
tccctattgc cacggcggaa ctcatcgccg cctgccttgc ccgctgctgg acaggggctc      6720
ggctgttggg cactgacaat tccgtggtgt tgtcggggaa gctgacgtcc tttccatggc      6780
tgctcgcctg tgttgccacc tggattctgc gcgggacgtc cttctgctac gtcccttcgg      6840
ccctcaatcc agcggacctt ccttcccgcg gcctgctgcc ggctctgcgg cctcttccgc      6900
gtcttcgcct tcgccctcag acgagtcgga tctcccttg ggccgcctcc ccgcatcggg      6960
aattcgagct cggtaccttt aagaccaatg acttacaagg cagctgtaga tcttagccac      7020
tttttaaaag aaaaggggg actggaaggg ctaattcact cccaacgaag acaagatggg      7080
atcaattcac catgggaata acttcgtata gcatacatta tacgaagtta tgctgctttt      7140
tgcttgtact gggtctctct ggttagacca gatctgagcc tgggagctct ctggctaact      7200
agggaaccca ctgcttaagc ctcaataaag cttgccttga gtgcttcaag tagtgtgtgc      7260
ccgtctgttg tgtgactctg gtaactagag atccctcaga cccttttagt cagtgtggaa      7320
aatctctagc agcatctaga attaattccg tgtattctat agtgtcacct aaatcgtatg      7380
tgtatgatac ataaggttat gtattaattg tagccgcgtt ctaacgacaa tatgtacaag      7440
cctaattgtg tagcatctgg cttactgaag cagacccctat catctctctc gtaaactgcc      7500
gtcagagtcg gtttggttgg acgaaccttc tgagtttctg gtaacgccgt cccgcacccg      7560
gaaatggtca gcgaaccaat cagcagggtc atcgctagcc agatcctcta cgccggacgc      7620
atcgtggccg gcatcaccgg cgccacaggt gcggttgctg gcgcctatat cgccgacatc      7680
accgatgggg aagatcgggc tcgccacttc gggctcatga gcgcttgttt cggcgtgggt      7740
atggtggcag gccccgtggc cggggggactg ttgggcgcca tctccttgca tgcaccattc      7800
cttgcggcgg cggtgctcaa cggcctcaac ctactactgg gctgcttcct aatgcaggag      7860
tcgcataagg gagagcgtcg aatggtgcac tctcagtaca atctgctctg atgccgcata      7920
gttaagccag ccccgacacc cgccaacacc cgctgacgcg ccctgacggg cttgtctgct      7980
```

```
cccggcatcc gcttacagac aagctgtgac cgtctccggg agctgcatgt gtcagaggtt    8040
ttcaccgtca tcaccgaaac gcgcgagacg aaagggcctc gtgatacgcc tattttata     8100 ggttaatgtc atgataataa tggtttctta gacgtcaggt ggcacttttc ggggaaatgt    8160
gcgcggaacc cctatttgtt tattttctta aatacattca aatatgtatc cgctcatgag    8220
acaataaccc tgataaatgc ttcaataata ttgaaaaagg aagagtatga gtattcaaca    8280
tttccgtgtc gcccttattc cctttttgc ggcattttgc cttcctgttt ttgctcaccc     8340
agaaacgctg gtgaaagtaa aagatgctga agatcagttg ggtgcacgag tgggttacat    8400
cgaactggat ctcaacagcg gtaagatcct tgagagtttt cgccccgaag aacgttttcc    8460
aatgatgagc acttttaaag ttctgctatg tggcgcggta ttatcccgta ttgacgccgg    8520
gcaagagcaa ctcggtcgcc gcatacacta ttctcagaat gacttggttg agtactcacc    8580
agtcacagaa aagcatctta cggatggcat gacagtaaga gaattatgca gtgctgccat    8640
aaccatgagt gataacactg cggccaactt acttctgaca acgatcggag gaccgaagga    8700
gctaaccgct ttttttgcaca acatggggga tcatgtaact cgccttgatc gttgggaacc   8760
ggagctgaat gaagccatac caaacgacga gcgtgacacc acgatgcctg tagcaatggc    8820
aacaacgttg cgcaaactat taactggcga actacttact ctagcttccc ggcaacaatt    8880
aatagactgg atggaggcgg ataaagttgc aggaccactt ctgcgctcgg cccttccggc    8940
tggctggttt attgctgata atctggagc cggtgagcgt gggtctcgcg gtatcattgc     9000
agcactgggg ccagatggta agccctcccg tatcgtagtt atctacacga cggggagtca    9060
ggcaactatg gatgaacgaa atagacagat cgctgagata ggtgcctcac tgattaagca    9120
ttggtaactg tcagaccaag tttactcata tactttag attgatttaa aacttcattt      9180
ttaatttaaa aggatctagg tgaagatcct ttttgataat ctcatgacca aaatccctta    9240
acgtgagttt tcgttccact gagcgtcaga ccccgtagaa aagatcaaag gatcttcttg    9300
agatcctttt tttctgcgcg taatctgctg cttgcaaaca aaaaaaccac cgctaccagc    9360
ggtggtttgt ttgccggatc aagagctacc aactctttt ccgaaggtaa ctggcttcag     9420
cagagcgcag ataccaaata ctgtccttct agtgtagccg tagttaggcc accacttcaa    9480
gaactctgta gcaccgccta catacctcgc tctgctaatc ctgttaccag tggctgctgc    9540
cagtggcgat aagtcgtgtc ttaccgggtt ggactcaaga cgatagttac cggataaggc    9600
gcagcggtcg gctgaacgg ggggttcgtg cacacagccc agcttggagc gaacgaccta     9660
caccgaactg agatacctac agcgtgagca ttgagaaagc gccacgcttc ccgaaggag     9720 aaaggcggac aggtatccgg taagcggcag ggtcggaaca ggagagcgca cgagggagct    9780 tccagggga aacgcctggt atctttatag tcctgtcggg tttcgccacc tctgacttga     9840
gcgtcgattt ttgtgatgct cgtcaggggg gcggagccta tggaaaaacg ccagcaacgc    9900
ggccttttta cggttcctgg ccttttgctg gccttttgct cacatgttct ttcctgcgtt    9960
atcccctgat tctgtggata accgtattac cgcctttgag tgagctgata ccgctcgccg    10020
cagccgaacg accgagcgca gcgagtcagt gagcgaggaa gcggaagagc gcccaatacg    10080
caaaccgcct ctccccgcgc gttggccgat tcattaatgc agctgtggaa tgtgtgtcag    10140
ttagggtgtg gaaagtcccc aggctcccca gcaggcagaa gtatgcaaag catgcatctc    10200
aattagtcag caaccaggtg tggaaagtcc ccaggctccc cagcaggcag aagtatgcaa    10260
agcatgcatc tcaattagtc agcaaccata gtcccgcccc taactccgcc catcccgccc    10320
```

```
ctaactccgc ccagttccgc ccattctccg ccccatggct gactaatttt ttttatttat    10380
gcagaggccg aggccgcctc ggcctctgag ctattccaga agtagtgagg aggcttttt     10440
ggaggcctag gcttttgcaa aaagcttgga cacaagacag gcttgcgaga tatgtttgag    10500
aataccactt tatcccgcgt cagggagagg cagtgcgtaa aaagacgcgg actcatgtga    10560
aatactggtt tttagtgcgc cagatctcta aatctcgcg caacctattt tcccctcgaa     10620
cacttttaa gccgtagata aacaggctgg gacacttcac atgagcgaaa aatacatcgt     10680
cacctgggac atgttgcaga tccatgcacg taaactcgca agccgactga tgccttctga    10740
acaatggaaa ggcattattg ccgtaagccg tggcggtctg taccgggtgc gttactggcg    10800
cgtgaactgg gtattcgtca tgtcgatacc gtttgtattt ccagctacga tcacgacaac    10860
cagcgcgagc ttaaagtgct gaaacgcgca gaaggcgatg gcgaaggctt catcgttatt    10920
gatgacctgg tggataccgg tggtactgcg gttgcgattc gtgaaatgta ccaaaagcg     10980
cactttgtca ccatcttcgc aaaaccggct ggtcgtccgc tggttgatga ctatgttgtt    11040
gatatcccgc aagatacctg gattgaacag ccgtgggata tgggcgtcgt attcgtcccg    11100
ccaatctccg gtcgctaatc ttttcaacgc ctggcactgc cgggcgttgt tcttttaac    11160
ttcaggcggg ttacaatagt ttccagtaag tattctggag gctgcatcca tgacacaggc    11220
aaacctgagc gaaaccctgt tcaaaccccg ctttaaacat cctgaaacct cgacgctagt    11280
ccgccgcttt aatcacggcg cacaaccgcc tgtgcagtcg gccttgatg gtaaaaccat     11340
ccctcactgg tatcgcatga ttaaccgtct gatgtggatc tggcgcggca ttgacccacg    11400
cgaaatcctc gacgtccagg cacgtattgt gatgagcgat gccgaacgta ccgacgatga    11460
tttatacgat acggtgattg gctaccgtgg cggcaactgg atttatgagt gggccccgga    11520
tctttgtgaa ggaaccttac ttctgtggtg tgacataatt ggacaaacta cctacagaga    11580
tttaaagctc taaggtaaat ataaaatttt taagtgtata atgtgttaaa ctactgattc    11640
taattgtttg tgtattttag attccaacct atggaactga tgaatgggag cagtggtgga    11700
atgcctttaa tgaggaaaac ctgttttgct cagaagaaat gccatctagt gatgatgagg    11760
ctactgctga ctctcaacat tctactcctc caaaaagaa gagaaaggta gaagacccca     11820
aggactttcc ttcagaattg ctaagttttt tgagtcatgc tgtgtttagt aatagaactc    11880
ttgcttgctt tgctatttac accacaaagg aaaagctgc actgctatac aagaaaatta     11940
tggaaaaata ttctgtaacc tttataagta ggcataacag ttataatcat aacatactgt    12000
ttttcttac tccacacagg catagagtgt ctgctattaa taactatgct caaaaattgt     12060
gtacctttag cttttaatt tgtaaagggg ttaataagga atatttgatg tatagtgcct    12120
tgactagaga tcataatcag ccataccaca tttgtagagg ttttacttgc tttaaaaaac    12180
ctcccacacc tccccctgaa cctgaaacat aaaatgaatg caattgttgt tgttaacttg    12240
tttattgcag cttataatgg ttacaaataa agcaatagca tcacaaattt cacaaataaa    12300
gcatttttt cactgcattc tagttgtggt ttgtccaaac tcatcaatgt atcttatcat    12360
gtctggatca actggataac tcaagctaac caaaatcatc ccaaacttcc cacccatac     12420
cctattacca ctgccaatta cctagtggtt tcatttactc taaacctgtg attcctctga    12480
attattttca tttttaaagaa attgtatttg ttaaatatgt actacaaact tagtag       12536
```

<210> SEQ ID NO 11
<211> LENGTH: 365
<212> TYPE: PRT
<213> ORGANISM: Artificial Sequence
<220> FEATURE:
<223> OTHER INFORMATION: A synthetic FKBP-1SG-FR with GPI anchor amino
      acid sequence

<400> SEQUENCE: 11

Met Thr Thr Gln Leu Leu Leu Leu Val Trp Val Ala Val Val Gly
1               5                   10                  15

Glu Ala Gln Thr Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65              70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Ser
        115                 120                 125

Gly Gly Gly Ser Arg Ile Ala Trp Ala Arg Thr Glu Leu Leu Asn Val
    130                 135                 140

Cys Met Asn Ala Lys His His Lys Glu Lys Pro Gly Pro Glu Asp Lys
145                 150                 155                 160

Leu His Glu Gln Cys Arg Pro Trp Arg Lys Asn Ala Cys Cys Ser Thr
                165                 170                 175

Asn Thr Ser Gln Glu Ala His Lys Asp Val Ser Tyr Leu Tyr Arg Phe
            180                 185                 190

Asn Trp Asn His Cys Gly Glu Met Ala Pro Ala Cys Lys Arg His Phe
        195                 200                 205

Ile Gln Asp Thr Cys Leu Tyr Glu Cys Ser Pro Asn Leu Gly Pro Trp
    210                 215                 220

Ile Gln Gln Val Asp Gln Ser Trp Arg Lys Glu Arg Val Leu Asn Val
225                 230                 235                 240

Pro Leu Cys Lys Glu Asp Cys Glu Gln Trp Trp Glu Asp Cys Arg Thr
                245                 250                 255

Ser Tyr Thr Cys Lys Ser Asn Trp His Lys Gly Trp Asn Trp Thr Ser
            260                 265                 270

Gly Phe Asn Lys Cys Ala Val Gly Ala Ala Cys Gln Pro Phe His Phe
        275                 280                 285

Tyr Phe Pro Thr Pro Thr Val Leu Cys Asn Glu Ile Trp Thr His Ser
    290                 295                 300

Tyr Lys Val Ser Asn Tyr Ser Arg Gly Ser Gly Arg Cys Ile Gln Met
305                 310                 315                 320

Trp Phe Asp Pro Ala Gln Gly Asn Pro Asn Glu Glu Val Ala Arg Phe
                325                 330                 335

Tyr Ala Ala Ala Met Ser Gly Ala Gly Pro Trp Ala Ala Trp Pro Phe
            340                 345                 350

Leu Leu Ser Leu Ala Leu Met Leu Leu Trp Leu Leu Ser
        355                 360                 365

<210> SEQ ID NO 12
<211> LENGTH: 375
<212> TYPE: PRT

<213> ORGANISM: Artificial Sequence
<220> FEATURE:
<223> OTHER INFORMATION: A synthetic FKBP-3SG-FR with GPI anchor amino acid sequence

<400> SEQUENCE: 12

```
Met Thr Thr Gln Leu Leu Leu Leu Val Trp Val Ala Val Val Gly
1               5                   10                  15

Glu Ala Gln Thr Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
            35                  40                  45

Met Leu Glu Asp Gly Lys Lys Phe Asp Ser Ser Arg Asp Arg Asn Lys
50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
            115                 120                 125

Gly Gly Gly Ser Gly Gly Gly Ser Gly Gly Gly Ser Arg Ile
130                 135                 140

Ala Trp Ala Arg Thr Glu Leu Leu Asn Val Cys Met Asn Ala Lys His
145                 150                 155                 160

His Lys Glu Lys Pro Gly Pro Glu Asp Lys Leu His Glu Gln Cys Arg
                165                 170                 175

Pro Trp Arg Lys Asn Ala Cys Cys Ser Thr Asn Thr Ser Gln Glu Ala
            180                 185                 190

His Lys Asp Val Ser Tyr Leu Tyr Arg Phe Asn Trp Asn His Cys Gly
            195                 200                 205

Glu Met Ala Pro Ala Cys Lys Arg His Phe Ile Gln Asp Thr Cys Leu
210                 215                 220

Tyr Glu Cys Ser Pro Asn Leu Gly Pro Trp Ile Gln Gln Val Asp Gln
225                 230                 235                 240

Ser Trp Arg Lys Glu Arg Val Leu Asn Val Pro Leu Cys Lys Glu Asp
                245                 250                 255

Cys Glu Gln Trp Trp Glu Asp Cys Arg Thr Ser Tyr Thr Cys Lys Ser
            260                 265                 270

Asn Trp His Lys Gly Trp Asn Trp Thr Ser Gly Phe Asn Lys Cys Ala
            275                 280                 285

Val Gly Ala Ala Cys Gln Pro Phe His Phe Tyr Phe Pro Thr Pro Thr
290                 295                 300

Val Leu Cys Asn Glu Ile Trp Thr His Ser Tyr Lys Val Ser Asn Tyr
305                 310                 315                 320

Ser Arg Gly Ser Gly Arg Cys Ile Gln Met Trp Phe Asp Pro Ala Gln
                325                 330                 335

Gly Asn Pro Asn Glu Glu Val Ala Arg Phe Tyr Ala Ala Ala Met Ser
            340                 345                 350

Gly Ala Gly Pro Trp Ala Ala Trp Pro Phe Leu Leu Ser Leu Ala Leu
            355                 360                 365

Met Leu Leu Trp Leu Leu Ser
370                 375
```

<210> SEQ ID NO 13
<211> LENGTH: 513
<212> TYPE: PRT
<213> ORGANISM: Artificial Sequence
<220> FEATURE:
<223> OTHER INFORMATION: A synthetic 4M5.3-FR with GPI anchor amino acid sequence

<400> SEQUENCE: 13

```
Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
                20                  25                  30

Pro Val Ser Leu Gly Asp Gln Ala Ser Ile Ser Cys Arg Ser Ser Gln
            35                  40                  45

Ser Leu Val His Ser Asn Gly Asn Thr Tyr Leu Arg Trp Tyr Leu Gln
    50                  55                  60

Lys Pro Gly Gln Ser Pro Lys Val Leu Ile Tyr Lys Val Ser Asn Arg
65                  70                  75                  80

Val Ser Gly Val Pro Asp Arg Phe Ser Gly Ser Gly Ser Gly Thr Asp
                85                  90                  95

Phe Thr Leu Lys Ile Asn Arg Val Glu Ala Glu Asp Leu Gly Val Tyr
            100                 105                 110

Phe Cys Ser Gln Ser Thr His Val Pro Trp Thr Phe Gly Gly Gly Thr
        115                 120                 125

Lys Leu Glu Ile Lys Ser Ser Ala Asp Asp Ala Lys Lys Asp Ala Ala
130                 135                 140

Lys Lys Asp Asp Ala Lys Lys Asp Asp Ala Lys Lys Asp Gly Gly Val
145                 150                 155                 160

Lys Leu Asp Glu Thr Gly Gly Gly Leu Val Gln Pro Gly Gly Ala Met
                165                 170                 175

Lys Leu Ser Cys Val Thr Ser Gly Phe Thr Phe Gly His Tyr Trp Met
            180                 185                 190

Asn Trp Val Arg Gln Ser Pro Glu Lys Gly Leu Glu Trp Val Ala Gln
        195                 200                 205

Phe Arg Asn Lys Pro Tyr Asn Tyr Glu Thr Tyr Tyr Ser Asp Ser Val
    210                 215                 220

Lys Gly Arg Phe Thr Ile Ser Arg Asp Asp Ser Lys Ser Ser Val Tyr
225                 230                 235                 240

Leu Gln Met Asn Asn Leu Arg Val Glu Asp Thr Gly Ile Tyr Tyr Cys
                245                 250                 255

Thr Gly Ala Ser Tyr Gly Met Glu Tyr Leu Gly Gln Gly Thr Ser Val
            260                 265                 270

Thr Val Ser Ser Gly Gly Gly Ser Arg Ile Ala Trp Ala Arg Thr Glu
        275                 280                 285

Leu Leu Asn Val Cys Met Asn Ala Lys His His Lys Glu Lys Pro Gly
    290                 295                 300

Pro Glu Asp Lys Leu His Glu Gln Cys Arg Pro Trp Arg Lys Asn Ala
305                 310                 315                 320

Cys Cys Ser Thr Asn Thr Ser Gln Glu Ala His Lys Asp Val Ser Tyr
                325                 330                 335

Leu Tyr Arg Phe Asn Trp Asn His Cys Gly Glu Met Ala Pro Ala Cys
            340                 345                 350

Lys Arg His Phe Ile Gln Asp Thr Cys Leu Tyr Glu Cys Ser Pro Asn
        355                 360                 365
```

Leu Gly Pro Trp Ile Gln Gln Val Asp Gln Ser Trp Arg Lys Glu Arg
    370                 375                 380

Val Leu Asn Val Pro Leu Cys Lys Glu Asp Cys Glu Gln Trp Trp Glu
385                 390                 395                 400

Asp Cys Arg Thr Ser Tyr Thr Cys Lys Ser Asn Trp His Lys Gly Trp
                405                 410                 415

Asn Trp Thr Ser Gly Phe Asn Lys Cys Ala Val Gly Ala Ala Cys Gln
                420                 425                 430

Pro Phe His Phe Tyr Phe Pro Thr Pro Thr Val Leu Cys Asn Glu Ile
            435                 440                 445

Trp Thr His Ser Tyr Lys Val Ser Asn Tyr Ser Arg Gly Ser Gly Arg
        450                 455                 460

Cys Ile Gln Met Trp Phe Asp Pro Ala Gln Gly Asn Pro Asn Glu Glu
465                 470                 475                 480

Val Ala Arg Phe Tyr Ala Ala Met Ser Gly Ala Gly Pro Trp Ala
                485                 490                 495

Ala Trp Pro Phe Leu Leu Ser Leu Ala Leu Met Leu Leu Trp Leu Leu
                500                 505                 510

Ser

<210> SEQ ID NO 14
<211> LENGTH: 895
<212> TYPE: PRT
<213> ORGANISM: Artificial Sequence
<220> FEATURE:
<223> OTHER INFORMATION: A synthetic FMC63-T2A-FKBP3SGFR

<400> SEQUENCE: 14

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
50              55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

```
Thr Thr Tyr Tyr Asn Ser Ala Leu Lys Ser Arg Leu Thr Ile Ile Lys
210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
            245                 250                 255

Ser Tyr Ala Met Asp Tyr Trp Gly Gln Gly Thr Ser Val Thr Val Ser
            260                 265                 270

Ser Ala Ala Ala Ile Glu Val Met Tyr Pro Pro Tyr Leu Asp Asn
        275                 280                 285

Glu Lys Ser Asn Gly Thr Ile Ile His Val Lys Gly Lys His Leu Cys
290                 295                 300

Pro Ser Pro Leu Phe Pro Gly Pro Ser Lys Pro Phe Trp Val Leu Val
305                 310                 315                 320

Val Val Gly Gly Val Leu Ala Cys Tyr Ser Leu Leu Val Thr Val Ala
            325                 330                 335

Phe Ile Ile Phe Trp Val Arg Ser Lys Arg Ser Arg Leu Leu His Ser
            340                 345                 350

Asp Tyr Met Asn Met Thr Pro Arg Arg Pro Gly Pro Thr Arg Lys His
            355                 360                 365

Tyr Gln Pro Tyr Ala Pro Pro Arg Asp Phe Ala Ala Tyr Arg Ser Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
            405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Gly
            485                 490                 495

Ser Gly Glu Gly Arg Gly Ser Leu Leu Thr Cys Gly Asp Val Glu Glu
            500                 505                 510

Asn Pro Gly Pro Met Ala Gln Arg Met Thr Thr Gln Leu Leu Leu Leu
            515                 520                 525

Leu Val Trp Val Ala Val Val Gly Glu Ala Gln Thr Gly Val Gln Val
530                 535                 540

Glu Thr Ile Ser Pro Gly Asp Gly Arg Thr Phe Pro Lys Arg Gly Gln
545                 550                 555                 560

Thr Cys Val Val His Tyr Thr Gly Met Leu Glu Asp Gly Lys Lys Phe
            565                 570                 575

Asp Ser Ser Arg Asp Arg Asn Lys Pro Phe Lys Phe Met Leu Gly Lys
            580                 585                 590

Gln Glu Val Ile Arg Gly Trp Glu Glu Gly Val Ala Gln Met Ser Val
            595                 600                 605

Gly Gln Arg Ala Lys Leu Thr Ile Ser Pro Asp Tyr Ala Tyr Gly Ala
610                 615                 620

Thr Gly His Pro Gly Ile Ile Pro Pro His Ala Thr Leu Val Phe Asp
```

```
                625                 630                 635                 640
Val Glu Leu Leu Lys Leu Glu Gly Gly Gly Ser Gly Gly Gly Gly
                        645                 650                 655

Ser Gly Gly Gly Ser Arg Ile Ala Trp Ala Arg Thr Glu Leu Leu
            660                 665                 670

Asn Val Cys Met Asn Ala Lys His Lys Glu Lys Pro Gly Pro Glu
        675                 680                 685

Asp Lys Leu His Glu Gln Cys Arg Pro Trp Arg Lys Asn Ala Cys Cys
    690                 695                 700

Ser Thr Asn Thr Ser Gln Glu Ala His Lys Asp Val Ser Tyr Leu Tyr
705                 710                 715                 720

Arg Phe Asn Trp Asn His Cys Gly Glu Met Ala Pro Ala Cys Lys Arg
                725                 730                 735

His Phe Ile Gln Asp Thr Cys Leu Tyr Glu Cys Ser Pro Asn Leu Gly
                740                 745                 750

Pro Trp Ile Gln Gln Val Asp Gln Ser Trp Arg Lys Glu Arg Val Leu
            755                 760                 765

Asn Val Pro Leu Cys Lys Glu Asp Cys Glu Gln Trp Trp Glu Asp Cys
        770                 775                 780

Arg Thr Ser Tyr Thr Cys Lys Ser Asn Trp His Lys Gly Trp Asn Trp
785                 790                 795                 800

Thr Ser Gly Phe Asn Lys Cys Ala Val Gly Ala Ala Cys Gln Pro Phe
                805                 810                 815

His Phe Tyr Phe Pro Thr Pro Thr Val Leu Cys Asn Glu Ile Trp Thr
                820                 825                 830

His Ser Tyr Lys Val Ser Asn Tyr Ser Arg Gly Ser Gly Arg Cys Ile
                835                 840                 845

Gln Met Trp Phe Asp Pro Ala Gln Gly Asn Pro Asn Glu Glu Val Ala
        850                 855                 860

Arg Phe Tyr Ala Ala Ala Met Ser Gly Ala Gly Pro Trp Ala Ala Trp
865                 870                 875                 880

Pro Phe Leu Leu Ser Leu Ala Leu Met Leu Leu Trp Leu Leu Ser
                885                 890                 895

<210> SEQ ID NO 15
<211> LENGTH: 1029
<212> TYPE: PRT
<213> ORGANISM: Artificial Sequence
<220> FEATURE:
<223> OTHER INFORMATION: A synthetic FMC63-T2A-4M5.3SGFR

<400> SEQUENCE: 15

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
```

```
                100             105             110
Asp Ile Ala Thr Tyr Phe Cys Gln Gln Gly Asn Thr Leu Pro Tyr Thr
            115             120             125
Phe Gly Gly Gly Thr Lys Leu Glu Ile Thr Gly Gly Gly Ser Gly
            130             135             140
Gly Gly Gly Ser Gly Gly Gly Ser Glu Val Lys Leu Gln Glu Ser
145             150             155             160
Gly Pro Gly Leu Val Ala Pro Ser Gln Ser Leu Ser Val Thr Cys Thr
            165             170             175
Val Ser Gly Val Ser Leu Pro Asp Tyr Gly Val Ser Trp Ile Arg Gln
            180             185             190
Pro Pro Arg Lys Gly Leu Glu Trp Leu Gly Val Ile Trp Gly Ser Glu
            195             200             205
Thr Thr Tyr Tyr Asn Ser Ala Leu Lys Ser Arg Leu Thr Ile Ile Lys
            210             215             220
Asp Asn Ser Lys Ser Gln Val Phe Leu Lys Met Asn Ser Leu Gln Thr
225             230             235             240
Asp Asp Thr Ala Ile Tyr Tyr Cys Ala Lys His Tyr Tyr Gly Gly
            245             250             255
Ser Tyr Ala Met Asp Tyr Trp Gly Gln Gly Thr Ser Val Thr Val Ser
            260             265             270
Ser Ala Ala Ala Ile Glu Val Met Tyr Pro Pro Pro Tyr Leu Asp Asn
            275             280             285
Glu Lys Ser Asn Gly Thr Ile Ile His Val Lys Gly Lys His Leu Cys
            290             295             300
Pro Ser Pro Leu Phe Pro Gly Pro Ser Lys Pro Phe Trp Val Leu Val
305             310             315             320
Val Val Gly Gly Val Leu Ala Cys Tyr Ser Leu Leu Val Thr Val Ala
            325             330             335
Phe Ile Ile Phe Trp Val Arg Ser Lys Arg Ser Arg Leu Leu His Ser
            340             345             350
Asp Tyr Met Asn Met Thr Pro Arg Arg Pro Gly Pro Thr Arg Lys His
            355             360             365
Tyr Gln Pro Tyr Ala Pro Pro Arg Asp Phe Ala Ala Tyr Arg Ser Arg
            370             375             380
Val Lys Phe Ser Arg Ser Ala Asp Ala Pro Ala Tyr Gln Gln Gly Gln
385             390             395             400
Asn Gln Leu Tyr Asn Glu Leu Asn Leu Gly Arg Arg Glu Glu Tyr Asp
            405             410             415
Val Leu Asp Lys Arg Arg Gly Arg Asp Pro Glu Met Gly Gly Lys Pro
            420             425             430
Arg Arg Lys Asn Pro Gln Glu Gly Leu Tyr Asn Glu Leu Gln Lys Asp
            435             440             445
Lys Met Ala Glu Ala Tyr Ser Glu Ile Gly Met Lys Gly Glu Arg Arg
            450             455             460
Arg Gly Lys Gly His Asp Gly Leu Tyr Gln Gly Leu Ser Thr Ala Thr
465             470             475             480
Lys Asp Thr Tyr Asp Ala Leu His Met Gln Ala Leu Pro Pro Arg Gly
            485             490             495
Ser Gly Glu Gly Arg Gly Ser Leu Leu Thr Cys Gly Asp Val Glu Glu
            500             505             510
Asn Pro Gly Pro Met Ala Leu Pro Val Thr Ala Leu Leu Leu Pro Leu
            515             520             525
```

Ala Leu Leu Leu His Ala Ala Arg Pro Asp Val Val Met Thr Gln Thr
            530                 535                 540

Pro Leu Ser Leu Pro Val Ser Leu Gly Asp Gln Ala Ser Ile Ser Cys
545                 550                 555                 560

Arg Ser Ser Gln Ser Leu Val His Ser Asn Gly Asn Thr Tyr Leu Arg
                565                 570                 575

Trp Tyr Leu Gln Lys Pro Gly Gln Ser Pro Lys Val Leu Ile Tyr Lys
            580                 585                 590

Val Ser Asn Arg Val Ser Gly Val Pro Asp Arg Phe Ser Gly Ser Gly
        595                 600                 605

Ser Gly Thr Asp Phe Thr Leu Lys Ile Asn Arg Val Glu Ala Glu Asp
    610                 615                 620

Leu Gly Val Tyr Phe Cys Ser Gln Ser Thr His Val Pro Trp Thr Phe
625                 630                 635                 640

Gly Gly Gly Thr Lys Leu Glu Ile Lys Ser Ser Ala Asp Asp Ala Lys
                645                 650                 655

Lys Asp Ala Ala Lys Lys Asp Ala Lys Lys Asp Asp Ala Lys Lys
            660                 665                 670

Asp Gly Gly Val Lys Leu Asp Glu Thr Gly Gly Leu Val Gln Pro
        675                 680                 685

Gly Gly Ala Met Lys Leu Ser Cys Val Thr Ser Gly Phe Thr Phe Gly
690                 695                 700

His Tyr Trp Met Asn Trp Val Arg Gln Ser Pro Glu Lys Gly Leu Glu
705                 710                 715                 720

Trp Val Ala Gln Phe Arg Asn Lys Pro Tyr Asn Tyr Glu Thr Tyr Tyr
                725                 730                 735

Ser Asp Ser Val Lys Gly Arg Phe Thr Ile Ser Arg Asp Asp Ser Lys
            740                 745                 750

Ser Ser Val Tyr Leu Gln Met Asn Asn Leu Arg Val Glu Asp Thr Gly
        755                 760                 765

Ile Tyr Tyr Cys Thr Gly Ala Ser Tyr Gly Met Glu Tyr Leu Gly Gln
    770                 775                 780

Gly Thr Ser Val Thr Val Ser Ser Gly Gly Gly Ser Arg Ile Ala Trp
785                 790                 795                 800

Ala Arg Thr Glu Leu Leu Asn Val Cys Met Asn Ala Lys His His Lys
                805                 810                 815

Glu Lys Pro Gly Pro Glu Asp Lys Leu His Glu Gln Cys Arg Pro Trp
            820                 825                 830

Arg Lys Asn Ala Cys Cys Ser Thr Asn Thr Ser Gln Glu Ala His Lys
        835                 840                 845

Asp Val Ser Tyr Leu Tyr Arg Phe Asn Trp Asn His Cys Gly Glu Met
850                 855                 860

Ala Pro Ala Cys Lys Arg His Phe Ile Gln Asp Thr Cys Leu Tyr Glu
865                 870                 875                 880

Cys Ser Pro Asn Leu Gly Pro Trp Ile Gln Val Asp Gln Ser Trp
                885                 890                 895

Arg Lys Glu Arg Val Leu Asn Val Pro Leu Cys Lys Glu Asp Cys Glu
            900                 905                 910

Gln Trp Trp Glu Asp Cys Arg Thr Ser Tyr Thr Cys Lys Ser Asn Trp
        915                 920                 925

His Lys Gly Trp Asn Trp Thr Ser Gly Phe Asn Lys Cys Ala Val Gly
930                 935                 940

```
Ala Ala Cys Gln Pro Phe His Phe Tyr Phe Pro Thr Pro Thr Val Leu
945                 950                 955                 960

Cys Asn Glu Ile Trp Thr His Ser Tyr Lys Val Ser Asn Tyr Ser Arg
                965                 970                 975

Gly Ser Gly Arg Cys Ile Gln Met Trp Phe Asp Pro Ala Gln Gly Asn
            980                 985                 990

Pro Asn Glu Glu Val Ala Arg Phe Tyr Ala Ala Ala Met Ser Gly Ala
        995                 1000                1005

Gly Pro Trp Ala Ala Trp Pro Phe Leu Leu Ser Leu Ala Leu Met
    1010            1015                1020

Leu Leu Trp Leu Leu Ser
    1025
```

<210> SEQ ID NO 16
<211> LENGTH: 255
<212> TYPE: PRT
<213> ORGANISM: Artificial Sequence
<220> FEATURE:
<223> OTHER INFORMATION: A synthetic FRb with signal peptide

<400> SEQUENCE: 16

```
Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
                20                  25                  30

Asp Ala Lys His His Lys Thr Lys Pro Gly Pro Glu Asp Lys Leu His
            35                  40                  45

Asp Gln Cys Ser Pro Trp Lys Lys Asn Ala Cys Cys Thr Ala Ser Thr
50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Ser Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255
```

<210> SEQ ID NO 17
<211> LENGTH: 335

```
<212> TYPE: PRT
<213> ORGANISM: Artificial Sequence
<220> FEATURE:
<223> OTHER INFORMATION: A synthetic uPAR with signal peptide

<400> SEQUENCE: 17
```

| | | | | | | | | | | | | | | |
|---|---|---|---|---|---|---|---|---|---|---|---|---|---|---|
| Met | Gly | His | Pro | Pro | Leu | Leu | Pro | Leu | Leu | Leu | Leu | His | Thr | Cys |
| 1 | | | | 5 | | | | | 10 | | | | | 15 |
| Val | Pro | Ala | Ser | Trp | Gly | Leu | Arg | Cys | Met | Gln | Cys | Lys | Thr | Asn | Gly |
| | | | 20 | | | | | 25 | | | | | 30 | | |
| Asp | Cys | Arg | Val | Glu | Glu | Cys | Ala | Leu | Gly | Gln | Asp | Leu | Cys | Arg | Thr |
| | | 35 | | | | | 40 | | | | | 45 | | | |
| Thr | Ile | Val | Arg | Leu | Trp | Glu | Glu | Gly | Glu | Glu | Leu | Glu | Leu | Val | Glu |
| 50 | | | | | 55 | | | | | 60 | | | | | |
| Lys | Ser | Cys | Thr | His | Ser | Glu | Lys | Thr | Asn | Arg | Thr | Leu | Ser | Tyr | Arg |
| 65 | | | | | 70 | | | | | 75 | | | | | 80 |
| Thr | Gly | Leu | Lys | Ile | Thr | Ser | Leu | Thr | Glu | Val | Val | Cys | Gly | Leu | Asp |
| | | | | 85 | | | | | 90 | | | | | 95 | |
| Leu | Cys | Asn | Gln | Gly | Asn | Ser | Gly | Arg | Ala | Val | Thr | Tyr | Ser | Arg | Ser |
| | | | 100 | | | | | 105 | | | | | 110 | | |
| Arg | Tyr | Leu | Glu | Cys | Ile | Ser | Cys | Gly | Ser | Ser | Asp | Met | Ser | Cys | Glu |
| | | | 115 | | | | | 120 | | | | | 125 | | |
| Arg | Gly | Arg | His | Gln | Ser | Leu | Gln | Cys | Arg | Ser | Pro | Glu | Glu | Gln | Cys |
| | | 130 | | | | | 135 | | | | | 140 | | | |
| Leu | Asp | Val | Val | Thr | His | Trp | Ile | Gln | Glu | Gly | Glu | Glu | Gly | Arg | Pro |
| 145 | | | | | 150 | | | | | 155 | | | | | 160 |
| Lys | Asp | Asp | Arg | His | Leu | Arg | Gly | Cys | Gly | Tyr | Leu | Pro | Gly | Cys | Pro |
| | | | | 165 | | | | | 170 | | | | | 175 | |
| Gly | Ser | Asn | Gly | Phe | His | Asn | Asn | Asp | Thr | Phe | His | Phe | Leu | Lys | Cys |
| | | | 180 | | | | | 185 | | | | | 190 | | |
| Cys | Asn | Thr | Thr | Lys | Cys | Asn | Glu | Gly | Pro | Ile | Leu | Glu | Leu | Glu | Asn |
| | | | | 195 | | | | | 200 | | | | | 205 | |
| Leu | Pro | Gln | Asn | Gly | Arg | Gln | Cys | Tyr | Ser | Cys | Lys | Gly | Asn | Ser | Thr |
| | | | 210 | | | | | 215 | | | | | 220 | | |
| His | Gly | Cys | Ser | Ser | Glu | Glu | Thr | Phe | Leu | Ile | Asp | Cys | Arg | Gly | Pro |
| 225 | | | | | 230 | | | | | 235 | | | | | 240 |
| Met | Asn | Gln | Cys | Leu | Val | Ala | Thr | Gly | Thr | His | Glu | Pro | Lys | Asn | Gln |
| | | | | 245 | | | | | 250 | | | | | 255 | |
| Ser | Tyr | Met | Val | Arg | Gly | Cys | Ala | Thr | Ala | Ser | Met | Cys | Gln | His | Ala |
| | | | 260 | | | | | 265 | | | | | 270 | | |
| His | Leu | Gly | Asp | Ala | Phe | Ser | Met | Asn | His | Ile | Asp | Val | Ser | Cys | Cys |
| | | | | 275 | | | | | 280 | | | | | 285 | |
| Thr | Lys | Ser | Gly | Cys | Asn | His | Pro | Asp | Leu | Asp | Val | Gln | Tyr | Arg | Ser |
| | | 290 | | | | | 295 | | | | | 300 | | | |
| Gly | Ala | Ala | Pro | Gln | Pro | Gly | Pro | Ala | His | Leu | Ser | Leu | Thr | Ile | Thr |
| 305 | | | | | 310 | | | | | 315 | | | | | 320 |
| Leu | Leu | Met | Thr | Ala | Arg | Leu | Trp | Gly | Gly | Thr | Leu | Leu | Trp | Thr | |
| | | | | 325 | | | | | 330 | | | | | 335 | |

```
<210> SEQ ID NO 18
<211> LENGTH: 187
<212> TYPE: PRT
<213> ORGANISM: Artificial Sequence
<220> FEATURE:
<223> OTHER INFORMATION: A synthetic DHFR

<400> SEQUENCE: 18
```

```
Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

<210> SEQ ID NO 19
<211> LENGTH: 255
<212> TYPE: PRT
<213> ORGANISM: Artificial Sequence
<220> FEATURE:
<223> OTHER INFORMATION: A synthetic scFv against FITC: 4M5.3(Kd =
      200pM)

<400> SEQUENCE: 19

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Ser Ser Ala Asp Asp Ala Lys Lys Asp Ala Ala Lys Lys Asp Asp Ala
        115                 120                 125

Lys Lys Asp Asp Ala Lys Lys Asp Gly Val Lys Leu Asp Glu Thr
    130                 135                 140

Gly Gly Gly Leu Val Gln Pro Gly Gly Ala Met Lys Leu Ser Cys Val
145                 150                 155                 160

Thr Ser Gly Phe Thr Phe Gly His Tyr Trp Met Asn Trp Val Arg Gln
```

165                 170                 175

Ser Pro Glu Lys Gly Leu Glu Trp Val Ala Gln Phe Arg Asn Lys Pro
            180                 185                 190

Tyr Asn Tyr Glu Thr Tyr Tyr Ser Asp Ser Val Lys Gly Arg Phe Thr
            195                 200                 205

Ile Ser Arg Asp Asp Ser Lys Ser Ser Val Tyr Leu Gln Met Asn Asn
            210                 215                 220

Leu Arg Val Glu Asp Thr Gly Ile Tyr Tyr Cys Thr Gly Ala Ser Tyr
225                 230                 235                 240

Gly Met Glu Tyr Leu Gly Gln Gly Thr Ser Val Thr Val Ser Ser
                245                 250                 255

<210> SEQ ID NO 20
<211> LENGTH: 244
<212> TYPE: PRT
<213> ORGANISM: Artificial Sequence
<220> FEATURE:
<223> OTHER INFORMATION: A synthetic scFv against FITC 4D5Flu (Kd=10nM)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Thr Tyr Ile His Trp
145                 150                 155                 160

Val Arg Gln Ala Pro Gly Lys Gly Leu Glu Trp Val Ala Arg Ile Tyr
                165                 170                 175

Pro Thr Asn Gly Tyr Thr Arg Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Trp Gly
    210                 215                 220

Gly Asp Gly Phe Tyr Ala Met Asp Tyr Trp Gly Gln Gly Thr Leu Val
225                 230                 235                 240

Thr Val Ser Ser

<210> SEQ ID NO 21
<211> LENGTH: 244
<212> TYPE: PRT
<213> ORGANISM: Artificial Sequence

```
<220> FEATURE:
<223> OTHER INFORMATION: A synthetic scFv against DNP SPE7

<400> SEQUENCE: 21

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Gly Gly Thr Lys Leu Thr Val Leu Gly Gly Gly
                100                 105                 110

Gly Ser Gly Gly Gly Gly Ser Gly Gly Gly Gly Ser Glu Val Gln Leu
        115                 120                 125

Gln Gln Pro Gly Ala Glu Leu Val Lys Pro Gly Ala Ser Val Lys Leu
    130                 135                 140

Ser Cys Lys Ala Ser Gly Tyr Thr Phe Thr Ser Tyr Trp Met His Trp
145                 150                 155                 160

Val Lys Gln Arg Pro Gly Arg Gly Leu Glu Trp Ile Gly Arg Ile Asp
                165                 170                 175

Pro Asn Gly Gly Gly Thr Lys Tyr Asn Glu Lys Phe Lys Ser Lys Ala
                180                 185                 190

Thr Leu Thr Val Asp Lys Pro Ser Ser Thr Ala Tyr Met Gln Leu Ser
            195                 200                 205

Ser Leu Thr Ser Glu Asp Ser Ala Val Tyr Tyr Cys Ala Arg Met Trp
    210                 215                 220

Tyr Tyr Gly Thr Tyr Tyr Phe Asp Tyr Trp Gly Gln Gly Thr Thr Leu
225                 230                 235                 240

Thr Val Ser Ser

<210> SEQ ID NO 22
<211> LENGTH: 4
<212> TYPE: PRT
<213> ORGANISM: Artificial Sequence
<220> FEATURE:
<223> OTHER INFORMATION: A synthetic sequence

<400> SEQUENCE: 22

Asp Asp Arg Asp
1
```

TARGETED LIGAND-PAYLOAD BASED DRUG DELIVERY FOR CELL THERAPY

CROSS REFERENCE

This application is a US National Phase filing of PCT/US18/18557, filed on Feb. 17, 2018, which claims the benefit of US provisional application 62/460,118 under 35 U.S.C. § 119 (e), filed on Feb. 17, 2017. The content of which is expressly incorporated herein entirely.

INCORPORATION BY REFERENCE OF SEQUENCE LISTING

A Sequence Listing is provided herewith as a text file named "2384317.txt" created on Nov. 10, 2023, and having a size of 144.874 bytes. The contents of the text file are incorporated by reference herein in their entirety.

FIELD OF INVENTION

This disclosure provides a drug delivery platform for cell therapy. Particularly, an engineered protein is coupled with a high affinity ligand carrying at least one payload of drug to be internalized by the transplanted cell through the engineered protein to regulate transplanted cell therapy effects.

BACKGROUND

In the last few decades, great advances have been made in this field regarding the cell types, delivery methods and suitable diseases models. In terms of cell types, current cell therapies can be roughly categorized as chimeric antigen receptors (CARs), cell for tumor model and stem cell based regenerative medicine.

CAR T also known as chimeric T cell receptors, chimeric immunoreceptors or artificial T cell receptors, enable immune effector cells (usually T cells or NK cells) to recognize target cells with corresponding antigen and exercise their cytotoxic activity. The emergence and development of CAR-T technology provides promises to certain types of cancers, which turns CAR-T into a superstar in the field of both biomedical research and clinical studies.

Regenerative medicine is a game-changing area of medicine with the potential to fully heal damaged tissues and organs, offering solutions and hope for people who have conditions that today are beyond repair. Advances in developmental and cell biology, immunology, and other fields have unlocked new opportunities to refine existing regenerative therapies and develop novel ones.

Stem cells have the ability to develop—through a process called differentiation—into many different types of cells, such as skin cells, brain cells, lung cells and so on. Stem cells are a key component of regenerative medicine, as they open the door to new clinical applications.

A variety of stem cells, including adult and embryonic stem cells may be used in regenerative medicine. In addition, various types of progenitor cells, such as those found in umbilical cord blood, and bioengineered cells called induced pluripotent stem cells are used in regenerative medicine. Each type has unique qualities, with some being more versatile than others.

Many of the regenerative therapies under development begin with the particular patient's own cells. For example, a patient's own skin cells may be collected, reprogrammed in a laboratory to give them certain characteristics, and delivered back to the patient to treat his or her disease.

Although the anti CD19 CAR T has received great success in clinical applications for leukemia treatment, lethal side effects such as the cytokine storm generated from the fast lysis of tumor cells, as well as the killing of normal CD19+ B cells by the fast proliferating anti-CD19 CAR T cell requires finer control of the CAR T cell. In stem cell based regenerative therapy, efforts have been put to better understand the differentiation process and trophic roles of the transplanted cells in the target tissue. Meanwhile, these processes can be potentially altered by some small molecule drugs that specifically delivered to the stem cell to further contribute to the regeneration of the target tissue.

Another long lasting concern about the CAR T cells as well as other stem cell based regenerative therapy is the tumorigenic potential of these transplanted cells. In summary, it will be ideal to have a private doorway to control the activity of the transplanted cell, either CAR T cell or stem cell, after they are being transplanted.

SUMMARY OF THE INVENTION

This disclosure provides a drug delivery platform for fine tuning cell therapy. The drug delivery system comprises:
a. an engineered protein on a target cell for transplant, wherein the fusion protein comprises a first component and a second component, the first component and the second component are connected by a peptide linker, the first component is a non-membrane protein, the second component is a membrane anchored peptide or protein;
b. at least one small ligand conjugated to a linker, wherein the at least one small ligand has intrinsic high affinity to at least one component of the engineered protein; and
c. at least one payload of drug conjugated to the linker, wherein the payload of drug is associated with the target cell when the small ligand binds to at least one component of the engineered protein.

In some embodiment, the aforementioned drug delivery platform has a payload of drug of imaging agent. Such imaging agent may be sleeted from the group consisting of fluorescent dye rhodamine, fluorescein, and S0456. Alternatively, such imaging agent is selected from the group consisting of radioisotope chelating imaging moieties, EC 20 chelating head, NOTA and DOTA.

In some embodiment, the aforementioned drug delivery platform has a payload of drug of cytotoxic drug. Such cytoxic drug may be selected from the group consisting of tubulysin, DM1, DM4, and an auristatin.

In some embodiment, the aforementioned drug delivery platform has a payload of drug of a modulator of gene expression.

In some embodiment, the aforementioned drug delivery platform has a payload of drug of modulator of the cell's activity.

In some embodiments, the aforementioned modulator may be selected from the group of Dasatinib, MEK1/2 inhibitor, and PI3K inhibitor; group of HDAC inhibitor, kinase inhibitor and metabolic inhibitor; group of GSK3 beta inhibitor, MAO-B inhibitor and Cdk5 inhibitor.

In some embodiments, the aforementioned modulator is a phosphatase inhibitor, an RORγt agonist or an siRNA mi181a1.

In some embodiments the aforementioned payload of drug is a phosphatase inhibitor, including but not limited to inhibitors against SHP1/2, TC-PTP.

In some embodiment, the aforementioned payload of drug in the drug delivery platform is further internalized by the target cell when the small ligand binds to at least one component of the engineered protein.

In some embodiments, the aforementioned drug delivery platform has a releasable linker to connect the small ligand and the payload drug. The linker can be selected from the group consisting of In some embodiment, the aforementioned engineered protein components are selected from the group consisting of Folate Receptor alpha (FRa), Folate Receptor beta (FRb), Urokinase receptor (uPAR), FK506 binding protein (FKBP), dihydrofolate reductase (DHFR), Single Chain Fragment Variable against Fluorescein isothiocyanate (scFv against FITC), and Single Chain Fragment Variable against dinitrophenol (scFv against DNP).

In some embodiment, the aforementioned small ligand is selected from the group consisting of

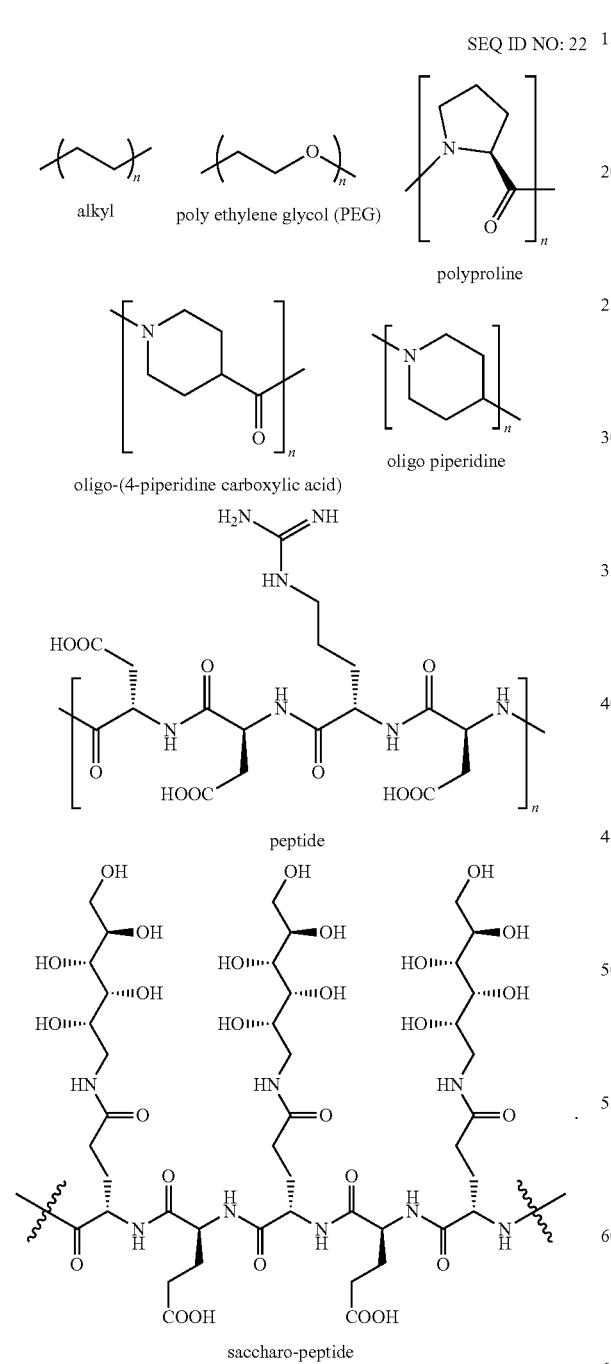

SEQ ID NO: 22

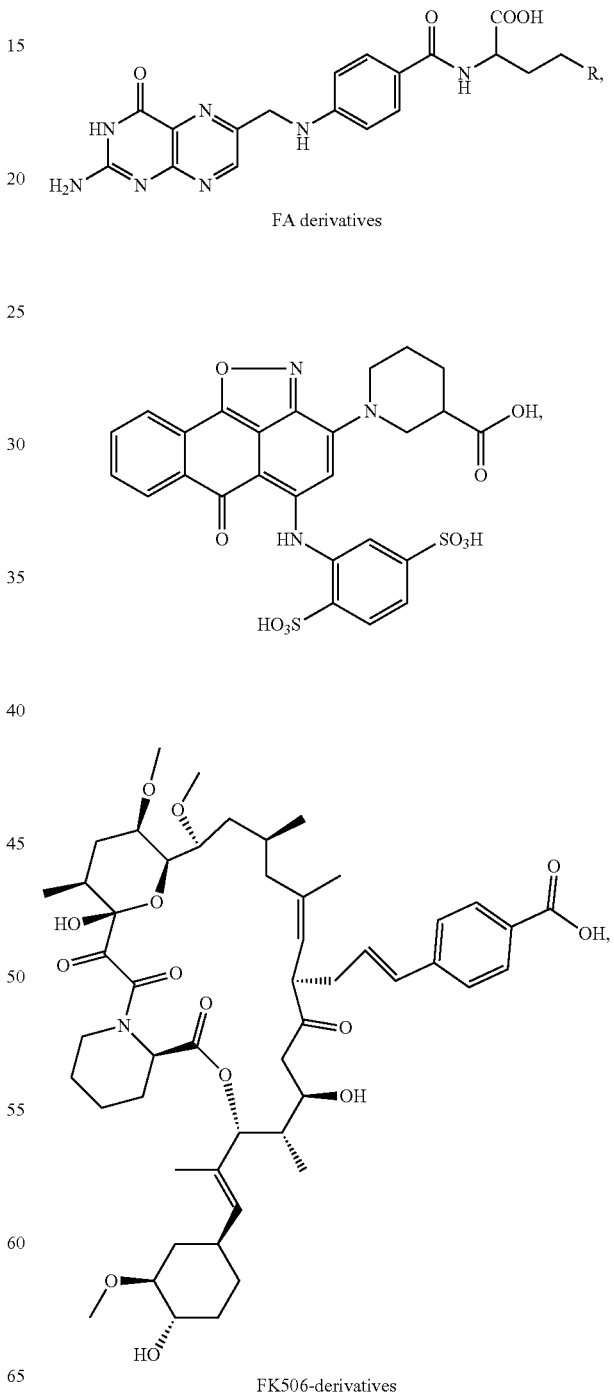

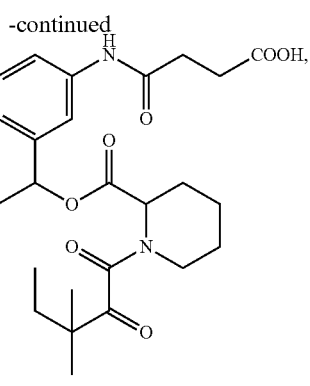

SLF derivatives

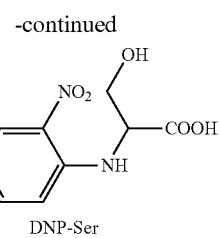

DNP-Ser

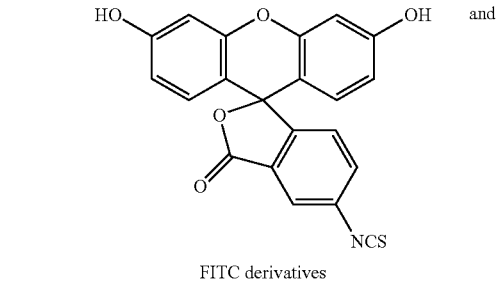

MFX derivatives

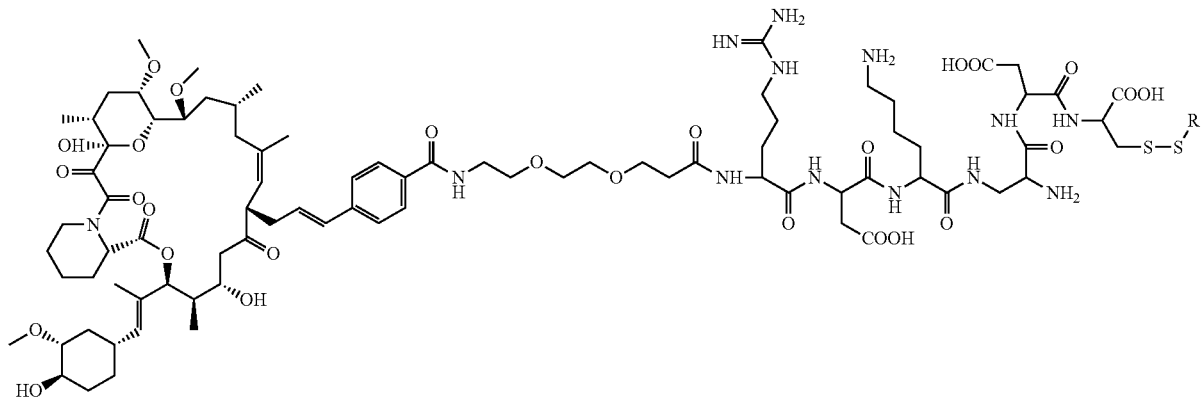

FITC derivatives

In some embodiment, the aforementioned drug delivery platform has the first component as FKBP, the second component is a peptide that confers a glycosylphosphatidyl inositol (GPI) anchor on the first component, and the small ligand is FK506 or its derivative. In some embodiment, the FK506 derivative abolishes Calcineurin binding site.

In some embodiment, the aforementioned second component is a full length or truncated Folate Receptor (FR).

In some embodiment, the aforementioned drug delivery platform has at least one segment of flexible peptide linker SGGGS to connect the first component and the second component of the engineered protein.

In some embodiment the aforementioned drug delivery platform comprises an engineered protein selected from the group consisting of SEQ ID NOS: 1-2 (amino acid sequence for mouse FKBP-FRa and amino acid sequence for human FKBP-FRa respectively).

In some embodiment the aforementioned drug delivery platform comprises an engineered protein selected from the group consisting of SEQ ID NOS: 12-15.

In some embodiment the aforementioned target cell for transplant is an immune cell. For example, the immune cell can be a NK cell or a Chimeric Antigen Receptor T (CAR T) cell. Such CAR T cell may be expressing amino acid sequence selected from SEQ ID NOS: 3-4.

In some embodiment the aforementioned drug delivery platform has the small ligand conjugate with formula I.

I

In some embodiment the aforementioned drug delivery platform has a target cell for transplant as CAR T cell expressing SEQ ID NO:3 (amino acid sequence for mouse antiCD19 CAR T construct) or SEQ ID NO:4 (amino acid sequence for human antiCD19 CAR T construct).

In some embodiment the aforementioned small ligand is further conjugated to a fluorescent dye or radioactive probe for tracking the drug internalization.

In some embodiment the aforementioned drug delivery platform comprises a small ligand that is further conjugated to a regulator of endogenous gene expression of a regulator of a transduced transgene expression.

In some embodiment the aforementioned drug delivery platform, the target cell for transplant is a stem cell, a progenitor cell, or a transplanted cell designed to synthesize a biochemical that is deficient in a patient. This disclosure further provides a CAR T cell comprising a construct expressing amino acid sequences selected from SEQ ID NOS: 12-15.

This disclosure further provides a DNA construct encoding an amino acid sequence selected from the group consisting of SEQ ID NOS: 12-15.

This disclosure further provides a DNA construct encoding a FKBP-FRa fusion receptor comprising any of SEQ ID NOS: 1-2 operably linked to an EFla promoter in a expression vector. In some embodiment, such expression vector is pWPI having SEQ ID NO:5.

This disclosure further provides a DNA construct comprising any of SEQ ID NOS: 6-8.

This disclosure further provides a transplanted cell comprising insert genes hFKBP-FR (SEQ ID NO:7) and human antiCD19 CAR (SEQ ID NO:9).

This disclosure further provides a transplant cell comprising insert genes mFKBP-FR (SEQ ID NO:8) and mouse antiCD19 CAR (SEQ ID NO:10).

This disclosure further provides a method to modulate cell therapy effect. The method comprises:

a. Identifying a target cell for transplant, wherein the transplanted target cell has a cell therapy function;

b. Providing an engineered fusion protein on the surface of the target cell for transplant, the fusion protein comprises a first component and a second component, the first component and the second component are connected by a flexible peptide linker, the first component is a non-membrane protein, the second component is a Glyclosylphosphatidyl inositol (GPI) anchored peptide or protein;

c. Providing a payload of drug conjugate to the target cell, wherein the payload of drug is conjugated to a small ligand through a linker, and optionally conjugated to a fluorescent dye, wherein the small ligand binds to at least one component of the engineered fusion protein with high affinity and is internalized by the target cell together with the payload of drug;

d. releasing the drug within the target cell to modulate the target cell therapy function.

In some embodiment, the aforementioned cell therapy function is to provide optically guided surgery to a subject.

In some embodiment, the aforementioned cell therapy function is to control the target cell proliferation.

In some embodiment, the aforementioned cell therapy function is to execute cytotoxicity to the target cell engaged cancer cell.

In some embodiment, the aforementioned transplanted target cell is an immune cell. For example, the target cell is a CAR T cell.

In some embodiment, the aforementioned transplanted target cell is a stem cell, a progenitor cell or a transplanted cell designed to synthesize a biochemical that is deficient in a patient.

In some embodiment, the aforementioned payload of drug is an imaging agent selected from fluorescent dye of Rhodamine and FITC, or a radioisotope imaging agent selected from EC20 chelating head, NOTA and DOTA.

In some embodiment, the aforementioned payload of drug is a cytotoxic drug selected from the group consisting of Tubulysin, DM1, DM4 and auristatin.

In some embodiment, the aforementioned payload of drug is a modulator of gene expression selected from kinase inhibitors consisting of Dasatinib, MEK1/2 inhibitor and PI3 Kinase inhibitor, or an siRNA of mi181a1.

In some embodiment, the aforementioned transplanted target cell comprises a fusion protein selected from the group consisting of SEQ ID NOS: 12-15.

In some embodiment, the aforementioned engineered protein components are selected from the group consisting of FRa, FRb, uPAR, FKBP, DHFR, scFv against FITC, and scFv against DNP.

In some embodiment, the aforementioned small ligand is selected from the group consisting of

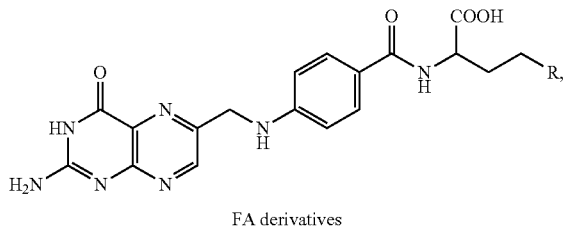

FA derivatives

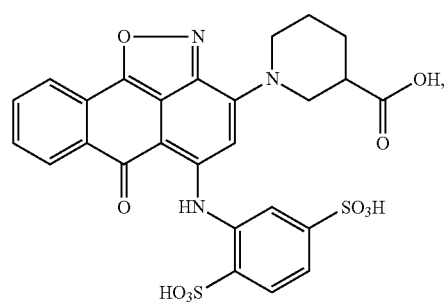 [SMILES: O=C1c2ccccc2-c2onc3c(N4CCCC(C(=O)O)C4)cc(Nc4cc(S(=O)(=O)O)ccc4S(=O)(=O)O)c1c23]

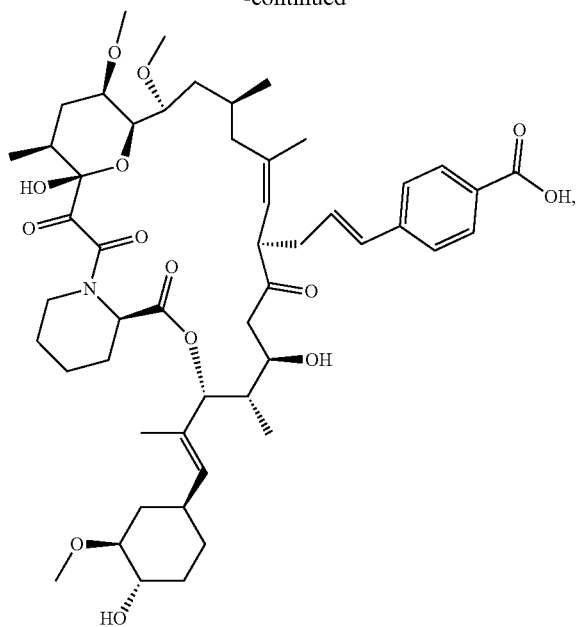
FK506-derivatives
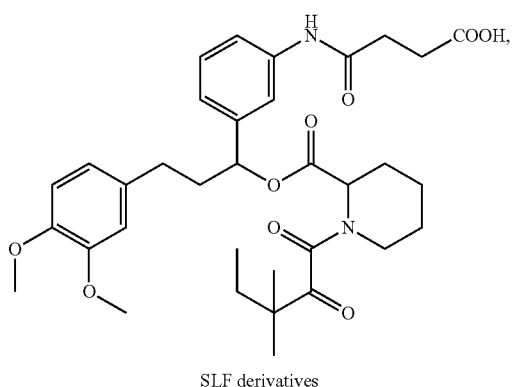 [SMILES: CCC(C)(C)C(=O)C(=O)N1CCCCC1C(=O)OC(CCc1ccc(OC)c(OC)c1)c1cccc(NC(=O)CCC(=O)O)c1]
SLF derivatives
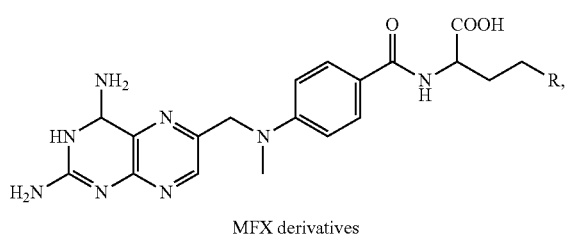
MFX derivatives
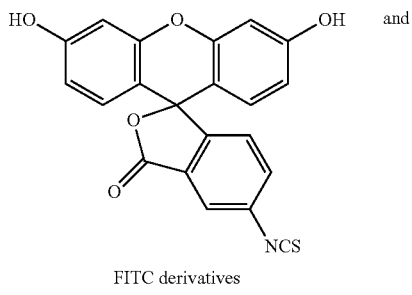
FITC derivatives
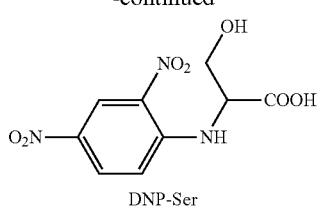
DNP-Ser
In some embodiments, the aforementioned linker to connect the small ligand and the payload drug is selected from the group consisting of
SEQ ID NO: 22
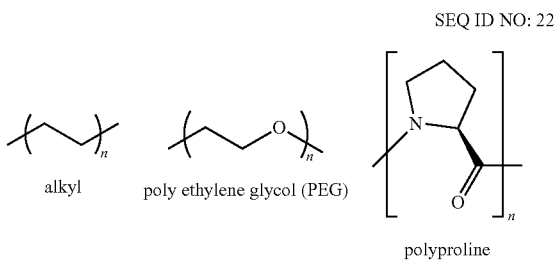
alkyl   poly ethylene glycol (PEG)   polyproline
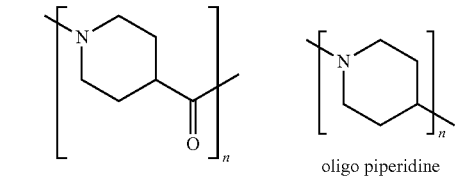 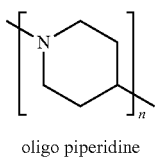
oligo-(4-piperidine carboxylic acid)   oligo piperidine
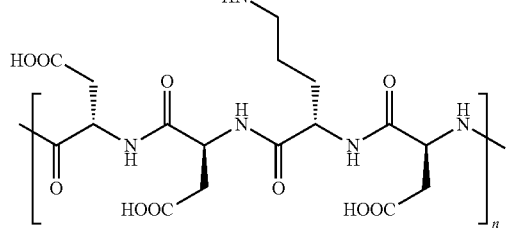
peptide
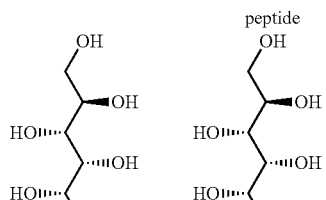
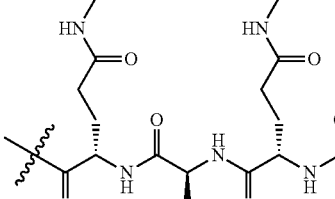
saccharo-peptide In some embodiment, the aforementioned transplanted target cell comprises an engineered FKBP-LINKER-FRa fusion protein selected from group consisting of SEQ ID NO:1 and SEQ ID NO:2.

In some embodiment, the aforementioned transplanted target cell is CAR T cell comprising an engineered antiCD19 CAR T construct selected from group consisting of SEQ ID NO:3 and SEQ ID NO:4.

In some embodiment, the aforementioned drug conjugate is FK506-releasable linker comprising formula I, wherein the binding domain of FK506 has an affinity to FKBP of about 4 pM to about 100 pM.

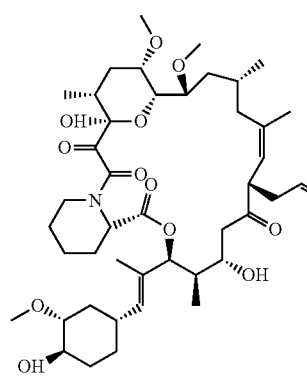
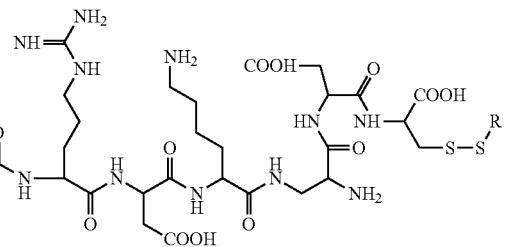

In some embodiment the aforementioned transplanted target cell is a CAR T cell and the drug conjugate is selected from the group consisting of GSK3b inhibitor, MAPK inhibitor to control excessive cytokine storm of transplanted CAR T cell.

In some embodiment the aforementioned transplanted target cell is a CAR T cell and the drug conjugate is a modulator designed to control unwanted T cell proliferation.

In some embodiment the aforementioned transplanted target cell is a stem cell or progenitor cell and the drug conjugate is GSK3b inhibitor to boost bone fracture repair.

In some embodiment the aforementioned transplanted target cell is a stem cell, a progenitor cell or a transplanted cell designed to synthesize a biochemical that is deficient in a patient; and the drug conjugate is selected from the group consisting of MAO-B inhibitor and cdk5 inhibitor to treat Parkinson disease or other neurodegenerative disease.

In some embodiment the aforementioned transplanted target cell is a NK cell and the drug conjugate is a RORγt agonist to control Th17 cell mediated immune responses.

These and other features, aspects and advantages of the present invention will become better understood with reference to the following figures, associated descriptions and claims.

Figure 1A:
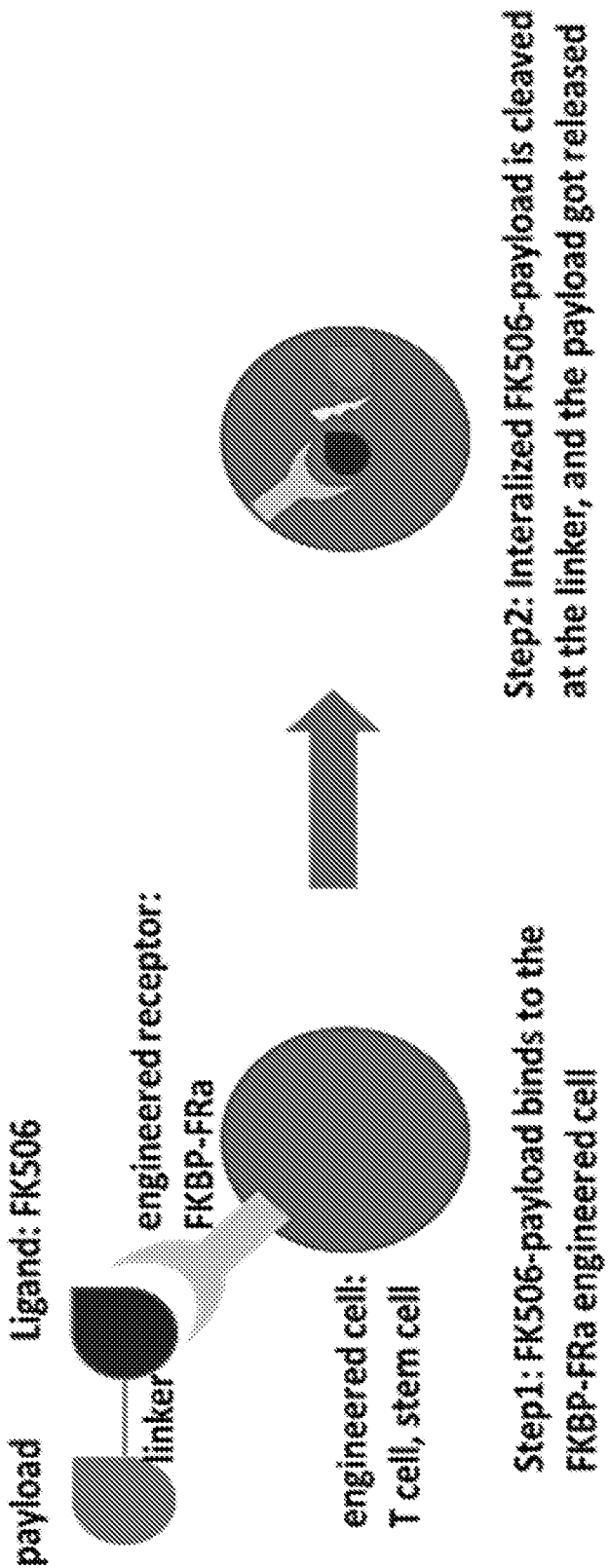
FIG. 1: A. overview of the FKBP-FRa and FK506-payload based drug delivery platform for cell therapy; B. Graphic illustration of the secret pathway platform for CAR T cells delivery of payload.

TABLE 1. Potential applications of the FKBP-FRa cell therapy platform and the corresponding payload.

Sequence Listings
    SEQ ID NO:1 Amino acid sequence for mouse FKBP-FRa
    SEQ ID NO:2 Amino acid sequence for human FKBP-FRa
    SEQ ID NO:3 Amino acid sequence for mouse antiCD19 CAR T construct
    SEQ ID NO:4 Amino acid sequence for human antiCD19 CAR T construct
    SEQ ID NO:5 vector pWPI for human T cell transduction
    SEQ ID NO:6 pMP71 gb NoIlEcoRI mouse antiCD19 for mouse T cell transduction
    SEQ ID NO:7 pWPI-FRa 1-24 FKBP FRa
    SEQ ID NO:8 pWPI niFKBP-mFRa SGGGS
    SEQ ID NO:9 pHR EcorI hAnti cd19 1D3 myc hinge cd28 cd3zeta
    SEQ ID NO:10 pWPI pmei mAnti cd19 1D3 myc hinge cd28 cd3zeta
    SEQ ID NO:11 FKBP-1SG-FR with GPI anchor amino acid sequence
    SEQ ID NO:12 FKBP-3SG-FR with GPI anchor amino acid sequence
    SEQ ID NO:13 4M5.3-FR with GPI anchor amino acid sequence
    SEQ ID NO:14 FMC63-T2A-FKBP3SGFR
    SEQ ID NO:15 FMC63-T2A-4M5.3SGFR
    SEQ ID NO:16 FRb with signal peptide
    SEQ ID NO:17 uPAR with signal peptide
    SEQ ID NO:18 DHFR
    SEQ ID NO:19 scFv against FITC: 4M5.3 (Kd=200 pM)
    SEQ ID NO:20 scFv against FITC 4D5Flu (Kd=10 nM)
    SEQ ID NO:21 scFv against DNP SPE7

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

This disclosure provides a novel platform for controlling the transplanted cell activity by genetically incorporating a fusion receptor on the transplanted cell surface. These transplanted cells will then be specifically targeted by a small molecule ligand conjugated-drug payload, using the intrinsic high affinity between the small molecule ligand and the fusion receptor on the transplanted cell surface. One part of the fusion receptor is responsible for internalizing the conjugate and the payload will be released through a releasable linker once it is inside of the transplanted cells. Depending on the transplanted cell type and the desired regulation to be imposed on the transplanted cells, the drug payload can be various functions. By changing the payload in the conjugate, for example, as cytotoxic drug or kinase inhibitors, the drug payload may be used to control the multiple aspects of the transplanted cells, such as proliferation, differentiation or cytokine release profile.

The peptidyl-proline isomerase (PPIases) family consists of FK506-binding protein (FKBP), cyclophilins and parvulins. In human, there are 18 FKBPs, 24 cyclophilins and 3 parvulins. Among these, FKBP51 and FKBP52 share high to moderate binding affinity of FK506, $KD^{FK506} \approx 104$ nM and $KD^{FK506} \approx 23$ nM, respectively, comparing to FKBP12 ($KD^{FK506} \approx 0.2$ nM). Additionally, none of these two FKBPs are expressed on the cell membrane, resulting in little cross binding activity in our system. Efforts have also been made to design synthetic ligands that have higher affinity to $FKBP12^{F36V}$ than $FKBP^{WT}$, as well as to $FKBP51^{F67V}$, which preserve the overall structure of the wild type proteins. All the homolog and mutated proteins together with their ligands mentioned above, can be adapted to this disclosure.

Particularly, in one embodiment, an exemplified pair of small molecule ligand and fusion receptor is chosen as FK506-FKBP. The entire process can be generalized in FIG. 1A, where the FK-506-payload binds to the FKBP-FRa engineered cell first; upon this binding, the transmembrane fusion protein will internalize the payload-linker-FK506. Next, the internalized FK506-payload is cleaved at the linker, and the pay load got released in the cell. Depending on the cell type and the payload type, the released payload drug can exert its desired function.

Figure 1B:
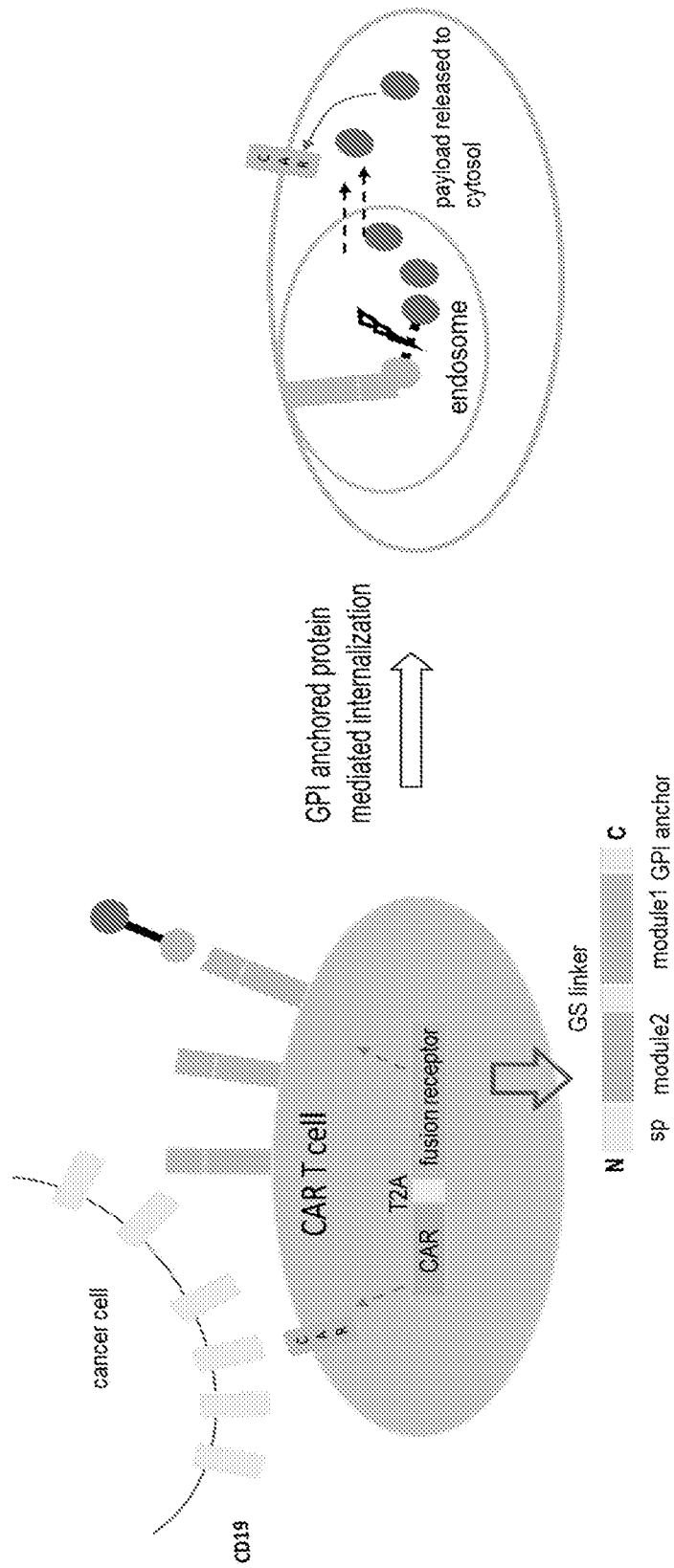

In FIG. 1B, a specific Chimeric Antigen Receptor T cell mediated cell therapy is illustrated. In this model, a CAR T cell expressing a fusion protein with the structure from N terminus to C terminus comprising a suitable signal peptide, a protein module 2 linked to a protein module 1 of GPI anchor is presented to a cancer cell. In some embodiment, the cancer cell has CD19 surface protein, which will be recognized by the CAR T cell and engaged with the payload associated with the CAR T cell, when a targeting ligand binds to at least one module of the fusion receptor. Typically, with high affinity of the targeting ligand toward any one of these modules, the payload associated with the ligand may be internalized into the target cell and be released to engage the cancer cell through the chimeric antigen receptor.

Figure 2A:
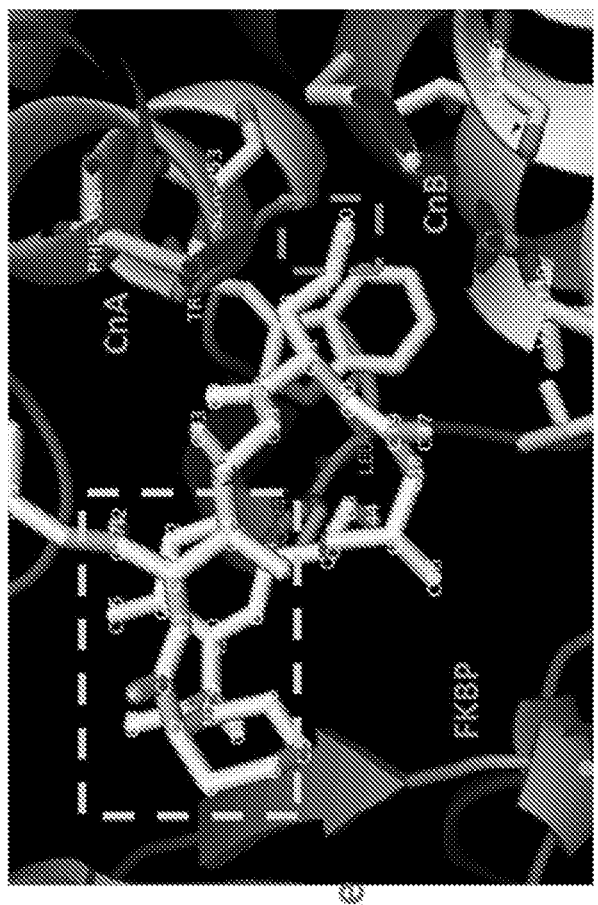
FIG. 2A.left: chemical structure of FK506 with FKBP binding sites (yellow) and derivatized site (red) highlighted. Right: co-crystal structure of ternary complex of a calcineurin A fragment (green), calcineurin B (cyan), FKBP12 (purple) and the FK506 (yellow), PDB: 1TCO FIG. 2B. Various combination options of two modules in an engineered fusion protein and their respective ligand choices, with potential derivatization sites highlighted.
Figure 2A:
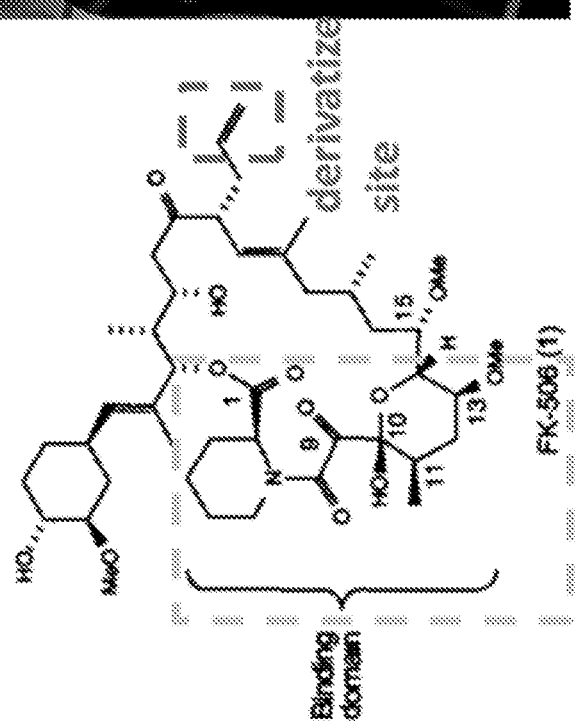
Figure 2B:
Figure 2B:
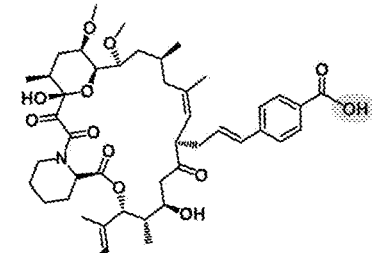
Figure 2B:
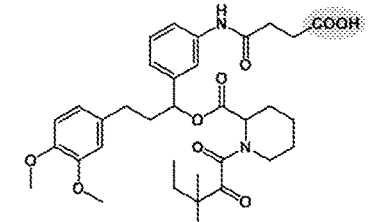
Figure 2B:
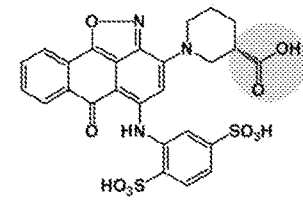
Figure 2B:
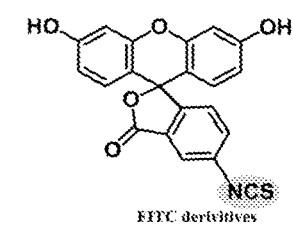
Figure 2B:
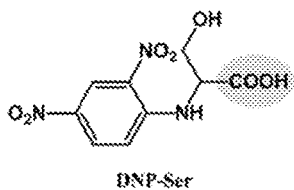

There can be many different combinations of GPI anchored proteins, represented as Module 1 and its ligands, and Module 2 target cell surface protein and its respective ligands, represented in FIG. 2B. It is contemplated that either module 1 protein or module 2 protein, or both can engage a high affinity targeting ligand to facilitate the ligand conjugated payload delivery. For example, it is feasible to have a fusion protein comprising FRa-Linker-FKBP structure, wherein FRa engaging with an FA derivative, at the same time, FKBP engaging a FK506 derivative, either FA derivative or FK 506 derivative or both can be linked to a payload, such as a cytotoxic drug, or an imaging agent, or a modulator. With such flexibility of carrying same or different payload, one can achieve some unexpected, synergy or regulatory effect of different or same payload, or to observe the target cell if the payload is an imaging agent. The advantages of flexibility and diversity of payload delivery of this system will be appreciated with more examples.

Similarly, another embodiment of ligand paired with a GPI anchored protein can be

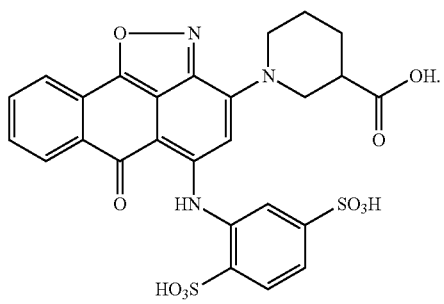

paired with uPAR.

It is also contemplated that FITC or its derivatives may bind to a single chain fragment of variant (scFv) of an antibody against FITC, for example, a ligand structure of

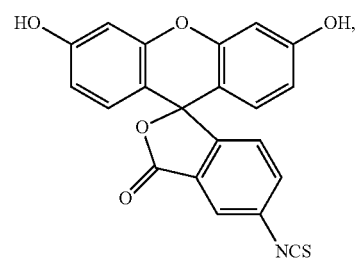

FITC derivatives or a structure of

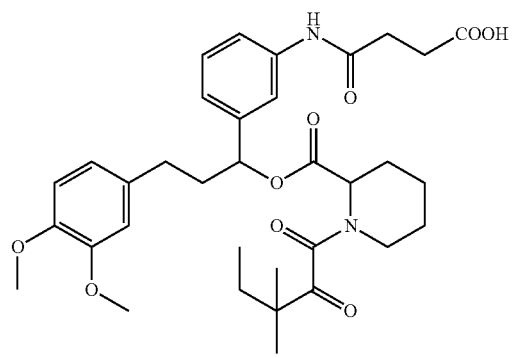

SLF derivatives paired with FKBP, or

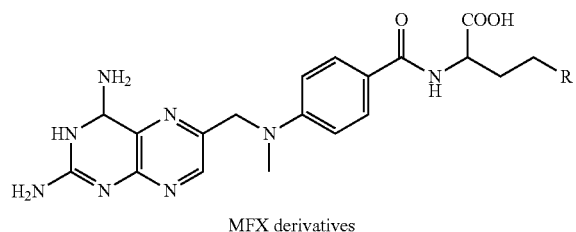

MFX derivatives paired with DHFR, or

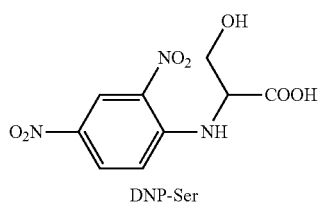 [SMILES: O=C(O)C(CO)Nc1ccc([N+](=O)[O-])cc1[N+](=O)[O-]]

DNP-Ser paired with scFV against DNP.

It is worth mentioning a few advantages of choosing FK506-FKBP as an exemplary ligand-protein pair in this delivery system. 1. FKBP is not a membrane protein that naturally present on the mammalian cell membrane, so that the FK506-payload conjugate will specifically bind to the target cell; 2. FKBP protein is a relatively small protein with molecular weight of 12 kDa, which makes it easier to be fused with other receptors with minimum perturbation to the receptors' structure and internalization properties. 3. FK506 is not naturally present inside human being, so that the fusion receptor will not be blocked; 4. The binding affinity between FK506-FKBP is around 4 pM so that the payload drug can be delivered with high affinity; 5. The co-crystal structure of FK506-FKBP is available and the well-established derivative site of FK506 preserves the binding of FK506-FKBP while abolishes the unwanted binding between FK506 and calcineurin (See FIG. 2A).

It is contemplated that the sequence of FKBP can be modified, and the corresponding FK506 ligand can be modified accordingly to the extent that the modified versions of FKBP and modified version of FK506 still have the desired affinity as exemplified herein or better than the current disclosure.

For the other portion of the fusion protein, folate receptor (FR) is chosen for its well understood internalization process as a monomer. Prior research shows that 'magic carbonate' linked folic acid conjugate can be internalized through FR and cleaved by the reductive environment inside the cell. Using this mechanism, the FK506-FKBP conjugated drug payload is internalized by FR and will then be released to the cytoplasm.

Figure 3:
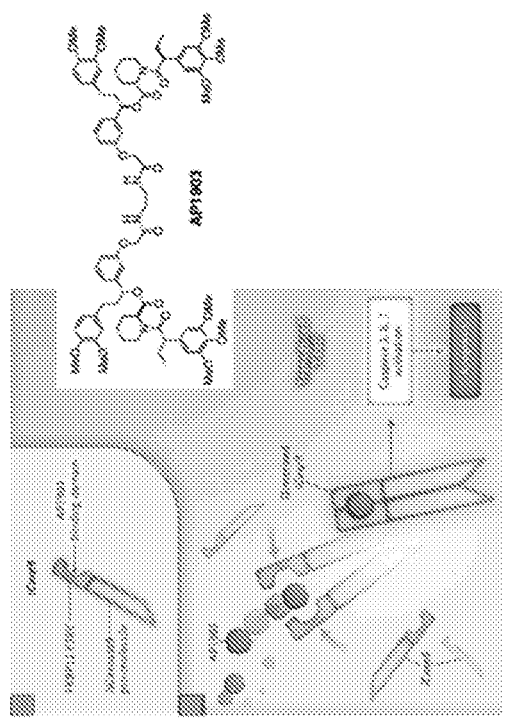
FIG. 3: left: negative and positive regulation of the CAR T cell activity, adapted from *The quest or spatio-temporal control of CAR T cells*, Sun J, etc. 2015. Right: mechanism of AP1903 (FK506 dimer) induced FKBP-caspase9 mediated apoptosis and the structure of AP1903, adapted *from Inducible Apoptosis as a Safety Switch for Adoptive Cell Therapy*, Malcolm K. B, etc. 2011
Figure 3:
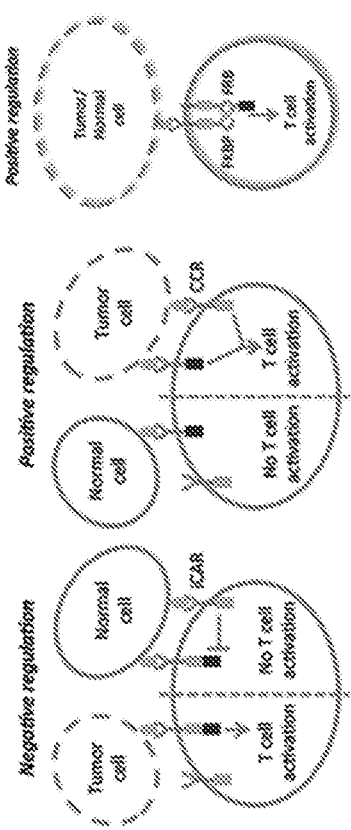

Due to the great potential of CAR T therapy as well as the severe side effects, several controlled CAR T cell designs have been reported. Most of them focused on the ON/OFF switch by incorporating either a Boolean gate or a cascade pathway for the T cell activation (see FIG. 3, left, which depicts negative and positive regulation of the CAR T cell activity, adapted from *The quest for spatio-temporal control of CAR T cells*, Sun J, etc. 2015). Malcolm K. B. group designed the FKBP-caspase9 fusion protein and use FK506 dimer to induce the apoptosis of the target cell (see FIG. 3, right, which depicts mechanism of AP1903 (FK506 dimer) induced FKBP-caspase9 mediated apoptosis and the structure of AP1903, adapted from *Inducible Apoptosis as a Safety Switch for Adoptive Cell Therapy*, Malcolm K. B, etc. 2011).

The current disclosure has several advantages over these reported methods: 1. Instead of a binary ON/OFF switch, our platform can delivery multiple kinds of regulating payloads, modifying many aspects of the target cells, thus it has great flexibility compared to binary ON/OFF switch; 2. the controlling moiety, FK506-payload, is a small molecule, which makes it possible for linear control and dosage optimization compared to pre-engineered cells. 3. The platform can be utilized in not only CAR T cell, but many other stem cell based regenerative therapies.

The greatest novelty and most important part of this platform is the multifunctional payloads, which can be selected to either address the potential side effects or improve the efficiency of the cell therapy. For instance, cytotoxic drugs can be delivered to the transplanted cells if: 1. the cells over-proliferate and affect the normal organ or system, like anti CD19 CAR T cell. 2. The cells become tumorigenic, which lies in the lentivirus based gene modification and the intrinsic characteristic of stem cells.

On the other hand, some cell therapies receive less success because of the suppressive microenvironment of the target tissue. For instance, in CAR T cell therapy against solid tumor, aside from the low penetration rate, the proliferation and activation of CAR T is highly suppressed by the MDSC and the tumor cells. This can be potentially alleviated by the RORrt agonist or MAP kinase inhibitor induced T cell activation as well as TLR8 agonist induced expression of granzyme B in CAR T cells. Although intracellular targets, like RORrt, may be more suitable for our payload, membrane receptors such as TLR8 may also be accessible due to the proximity on the cell membrane.

In stem cell regenerative therapy, the payload is more diverse according to the disease models. Instead of delivering a pre-fixed gene, which has been developed by using stem cell as a gene delivery platform, the current disclosure provides a fine tune to transplanted cells and their microenvironment, and obtains the desired phenotype through diverse small molecule payloads. Since the small molecule is conjugated to FK506, which specifically target the FKBP-FRa overexpressed transplant cell, the non-specific targeting of normal tissues of the small molecule is also avoided.

One of the many examples is to induce the overexpression of BMP2 in mesenchymal stem cell (MSC) for bone fracture repair in skeletal regenerative therapy. Meanwhile, the expression level of BMP2 and/or VEGF can be increased by introducing GSK3 beta inhibitor to the transplanted cells through this drug payload delivery system. GSK3 beta inhibitor is a desired drug for bone fracture repair. Therefore, GSK3 beta inhibitors is ideal as a potential payload for further modulating the function of the transplanted MSC as well as the microenvironment within the bone fracture sites.

Another example of this drug payload delivery system goes to the neurodegenerative disease, including Alzheimer, Parkinson disease and etc., where MSC based therapy holds a promising future. MSC has been modified to overexpress GDNF, VEGF and many other cytokines to promote the neuronal regeneration. Meanwhile, small molecules like MAO-B inhibitors has been confirmed to increase the expression of GDNF, NGF and BDNF in astrocytes. Several kinase inhibitors have also been proposed for the treatment of Alzheimer disease, such like PI3K inhibitor (BEZ235), Cdk5 inhibitor (roscovitine) and GSK3b inhibitor (NP-12). Using FK506-FKBP pair targeted specific delivery of these small molecules to MSC in neurodegenerative models will improve the regeneration efficacy while avoiding the side effects of these potent inhibitors and agonists in other non-targeted tissues.

Material and Methods

Compounds and Synthesis Procedure:

Targeting ligand is linked with payload through linkers. The linker optimization options are listed below, payloads are characterized into 3 classes: I imaging, II cytotoxic drug, III regulatory small molecule drug.

Linker Optimization:

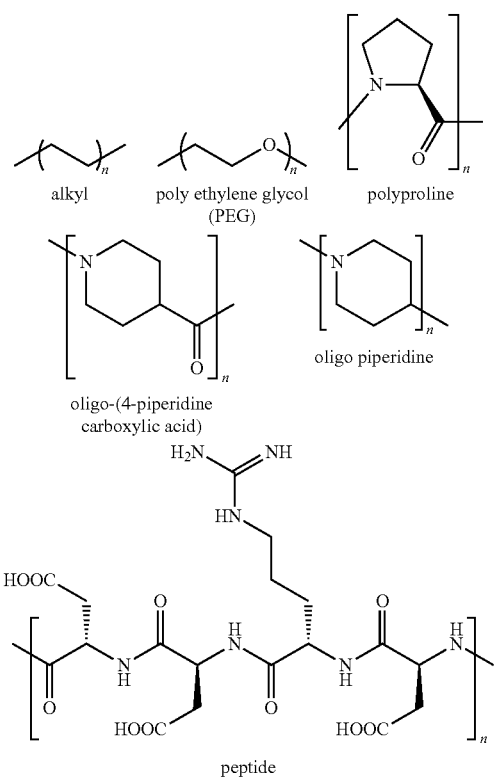

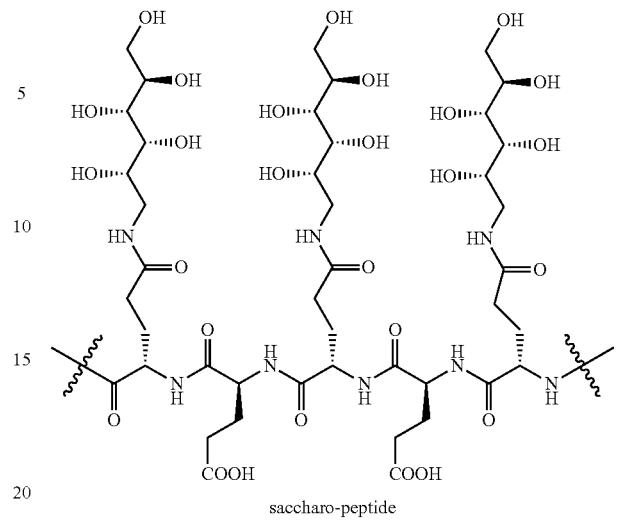

saccharo-peptide

Compounds Classification:

| Class | function | example |
|---|---|---|
| I | Imaging | Fluorescent dye: Rhodamine, FITC |
|  |  | Radioisotope imaging: EC20 chelating head, NOTA, DOTA |
| II | Cytotoxic drug | Anti-microtubule drug: Tubulysin, DM1, DM4 |
| III | Modulator | Kinase inhibitor: Dasatinib, MEK1/2i, PI3Ki |
|  |  | siRNA: mi181a1 |

Detailed Compound Structure and Synthesis Route
FK506-Rhodamine:

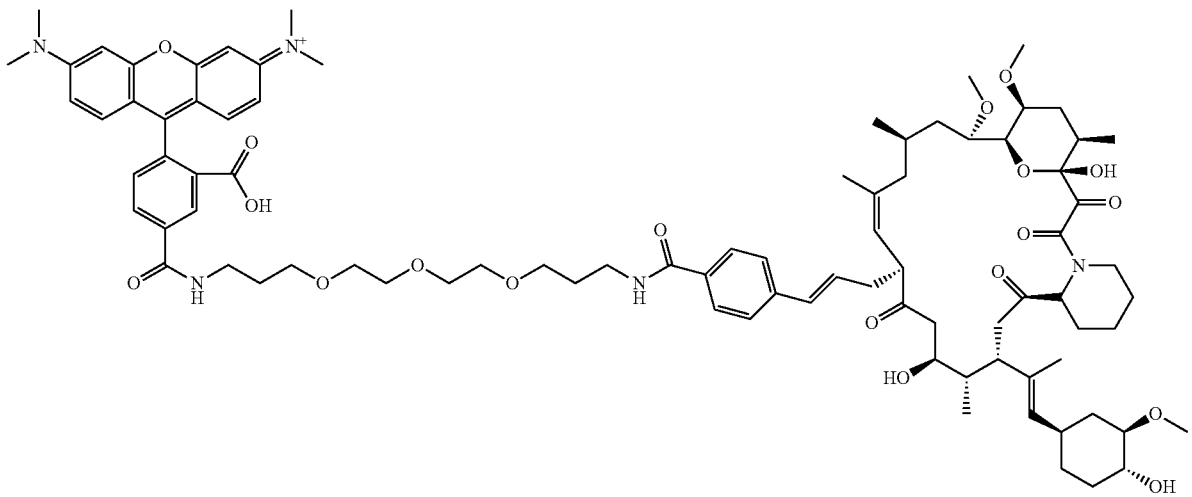

FK506-Rhodamine

Procedure: Rhodamine-NHS ester (1.0 equiv.) in dimethylformamide was reacted with Boc-NH-PEG$_3$-NH$_2$ (1.2 equiv.) and diisopropylethylamine (3.0 equiv.) for 2 h at room temperature. The product was purified by preparative reverse-phase HPLC with a UV detector. The purified Rhodamine-PEG$_3$-NH-Boc conjugate (1.0 equiv.) was subjected to Boc deprotection by stirring in a 1:10 TFA-dichloromethane system for 2 h. The crude free amine product was then dissolved in dimethylformamide and activated with EDC (2.0 equiv.), HOBT (2.0 equiv.) in the presence of diisopropylethylamine (3.0 equiv.). After 15 minutes, FK506-CO$_2$H (1.2 equiv., synthesized using the procedure in the reference: Bioorg. Med. Chem., 17 (2009) 5763-5768) was added and the reaction mixture was stirred overnight. The final FK506-Rhodamine conjugate was isolated after purification on preparative reverse-phase HPLC with a UV detector (monitored at wavelength of 280 nm). The crude product was loaded onto an Xterra RP18 preparative HPLC column (Waters) and eluted with gradient conditions starting with 95% 5 mM sodium phosphate (mobile phase A, pH7.4) and 5% acetonitrile (mobile phase B) and reaching 0% A and 50% B in 35 min at a flow rate of 12 mL/min. Retention time of the product peak=2.5 min during the gradient (0-50% JB) in a 7 min analytical HPLC-MS analysis. ESI m/z=1539.6.

Abbreviations: PEG-polyethylene glycol; EDC=1-Ethyl-3-(3-dimethylaminopropyl) carbodiimide; HOBT=Hydroxybenzotriazole; HPLC-High Performance Liquid Chromatography.

FK506-NIR Dye:

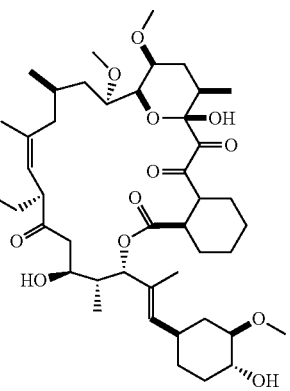

Molecular Weight: 2081.57

Synthesis Procedure:

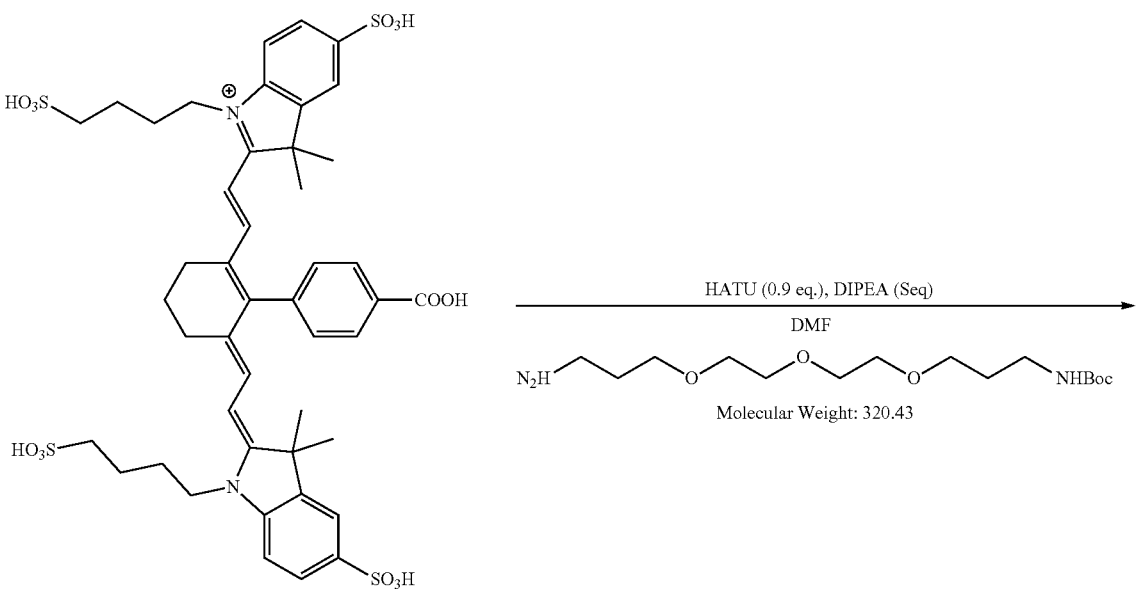

-continued
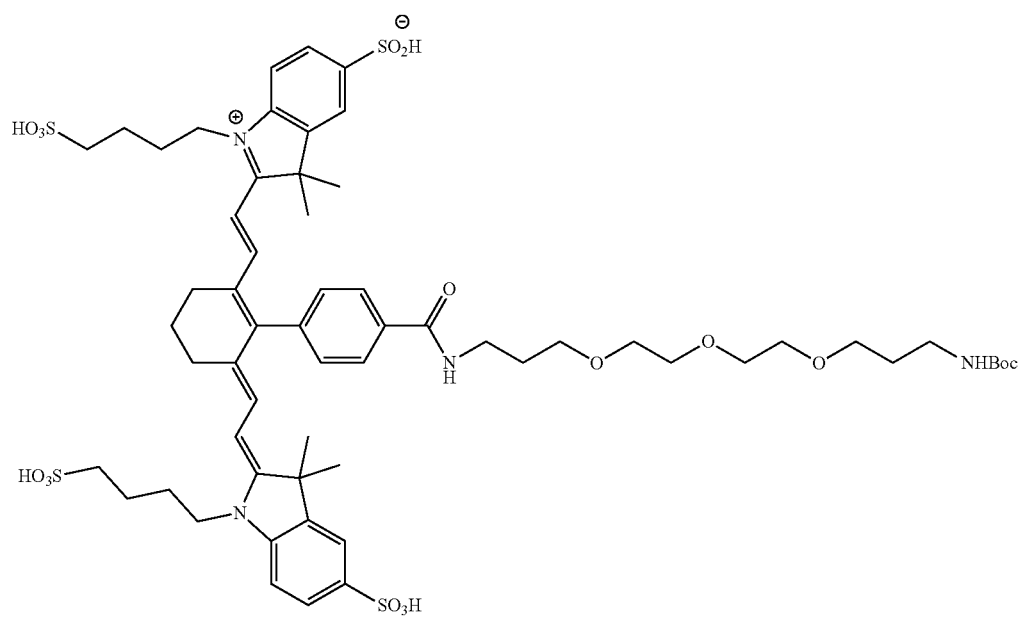
Molecular Weight: 1276.57
1. TFA/DCM (1:10)
2. EDC, HOBT, DIPA/DMF
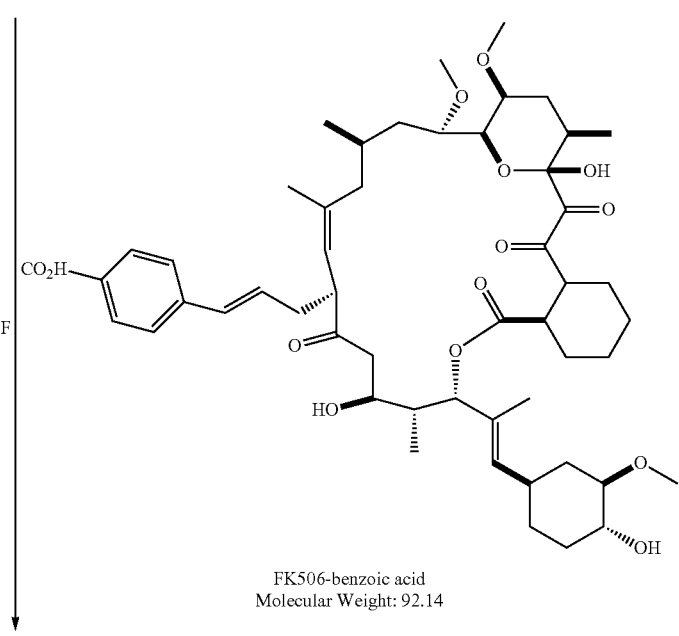
FK506-benzoic acid
Molecular Weight: 92.14

-continued
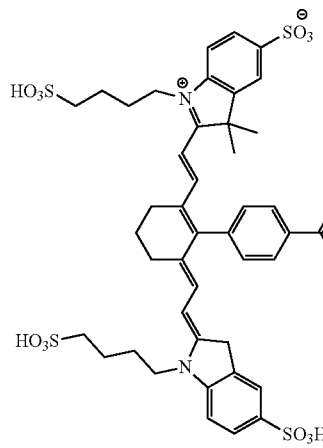 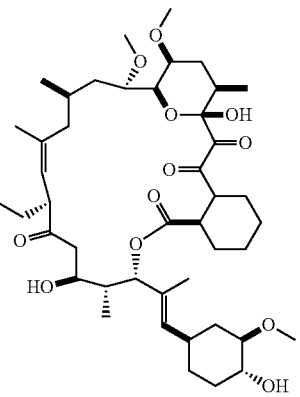
Molecular Weight: 2081.57
SLF-FITC:
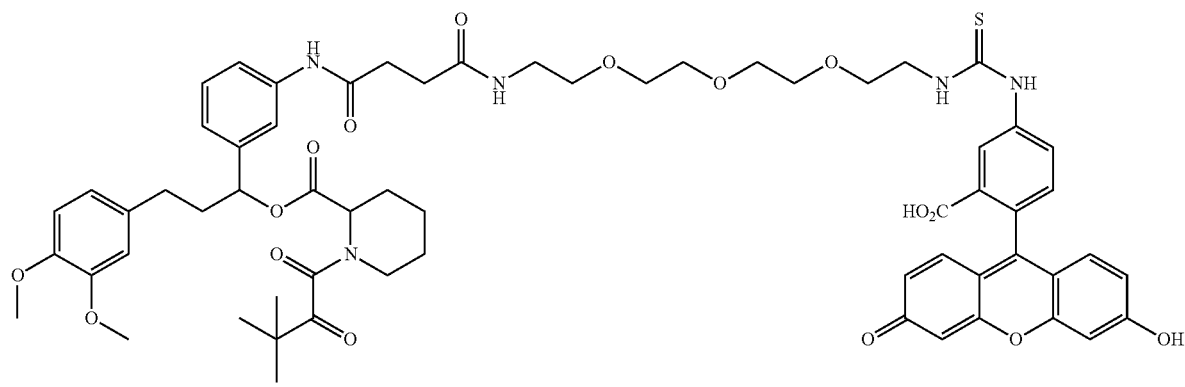
Chemical Formula: $C_{63}H_{73}N_5O_{16}S$
Exact Mass: 1187.48
Molecular Weight: 1188.36
Synthesis Procedure:
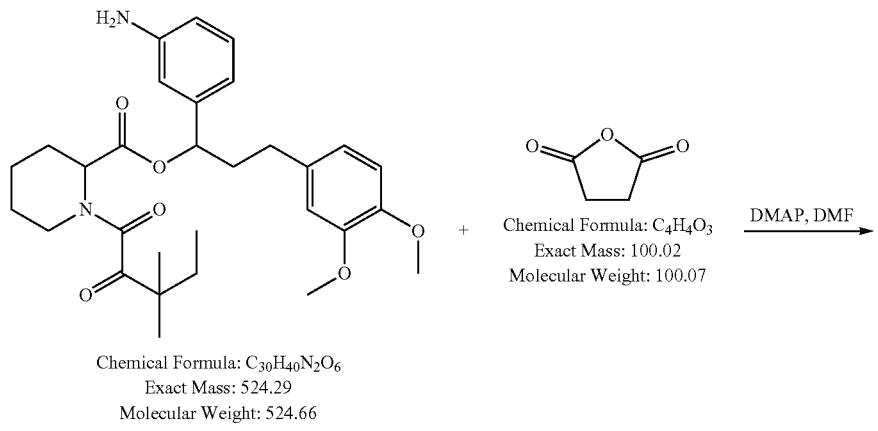
Chemical Formula: $C_{30}H_{40}N_2O_6$
Exact Mass: 524.29
Molecular Weight: 524.66
Chemical Formula: $C_4H_4O_3$
Exact Mass: 100.02
Molecular Weight: 100.07
DMAP, DMF →

-continued
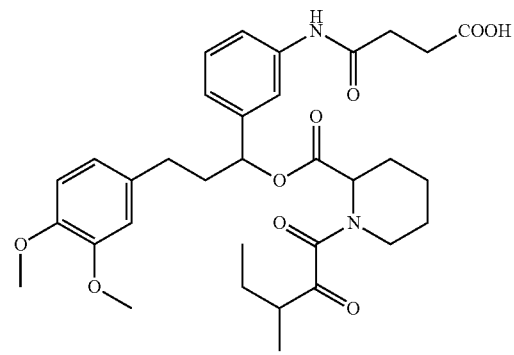
Chemical Formula: C$_{34}$H$_{44}$N$_2$O$_9$
Exact Mass: 624.30
Molecular Weight: 624.73
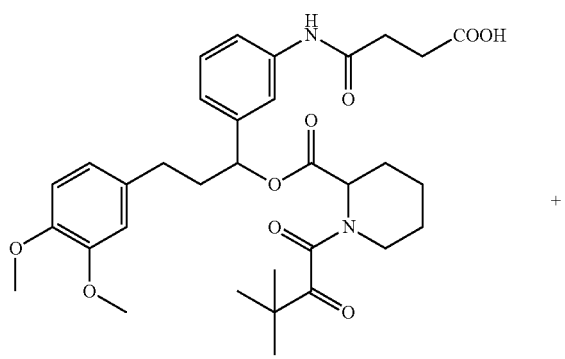
Chemical Formula: C$_{34}$H$_{44}$N$_2$O$_9$
Exact Mass: 624.30
Molecular Weight: 624.73
+
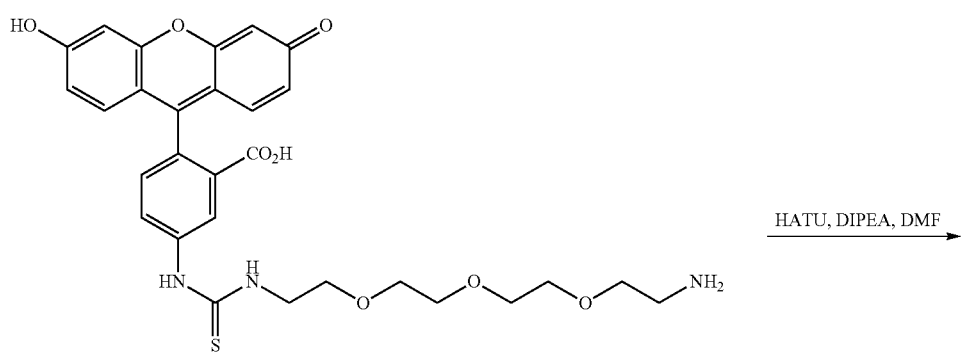
Chemical Formula: C$_{29}$H$_{31}$N$_3$O$_8$S
Exact Mass: 581.18
Molecular Weight: 581.64
HATU, DIPEA, DMF →

29
-continued
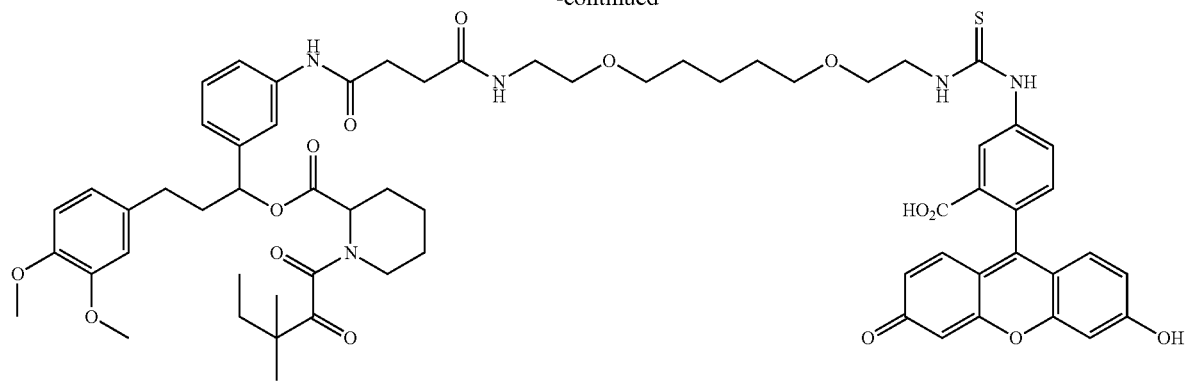
Chemical Formula: $C_{63}H_{73}N_5O_{16}S$
Exact Mass: 1187.48
Molecular Weight: 1188.36
SLF-EC20:
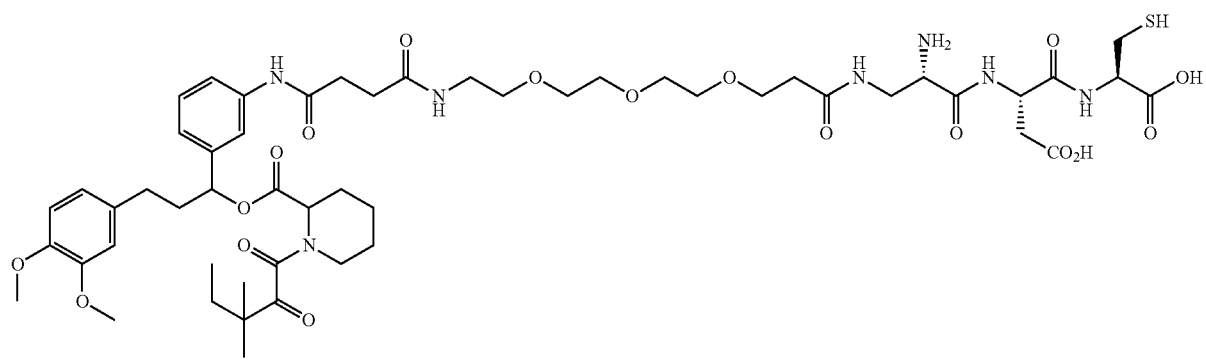
Chemical Formula: $C_{53}H_{77}N_7O_{18}S$
Exact Mass: 1131.50
Molecular Weight: 1132.29
Synthesis Procedure:
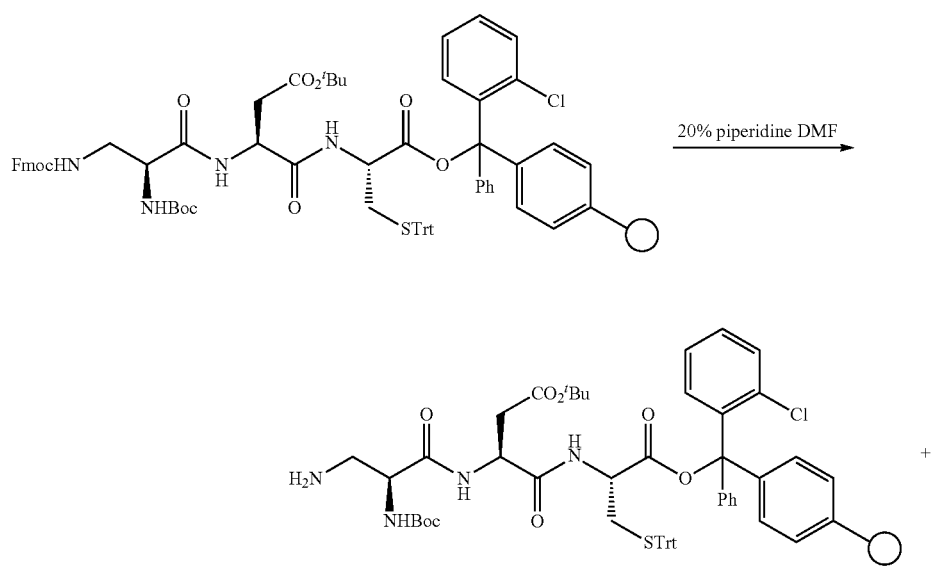

-continued
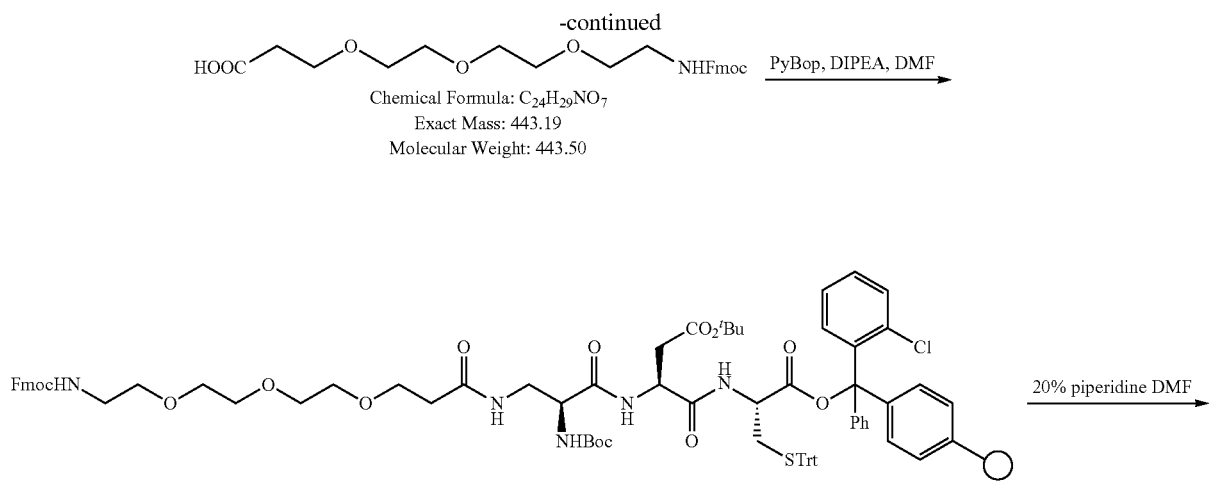
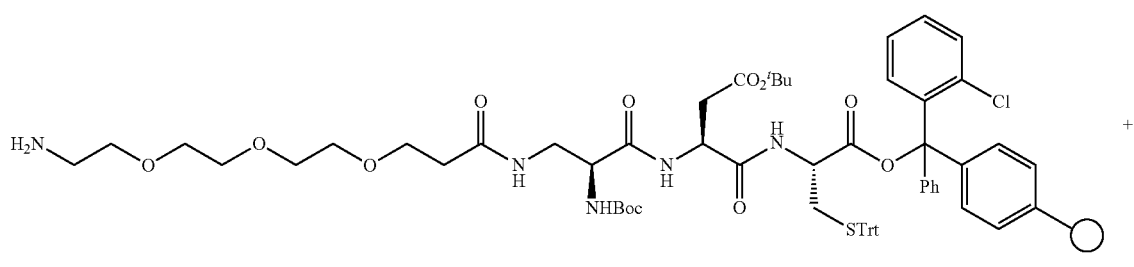
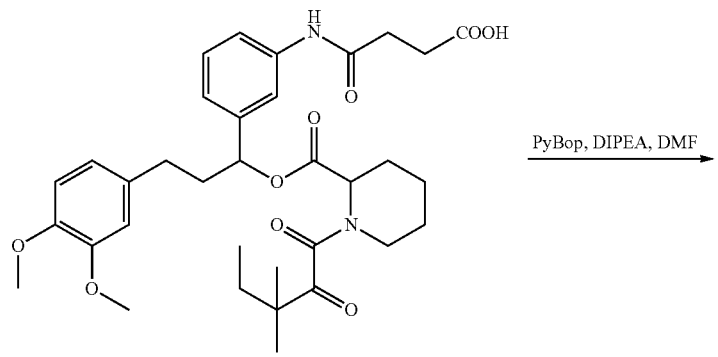
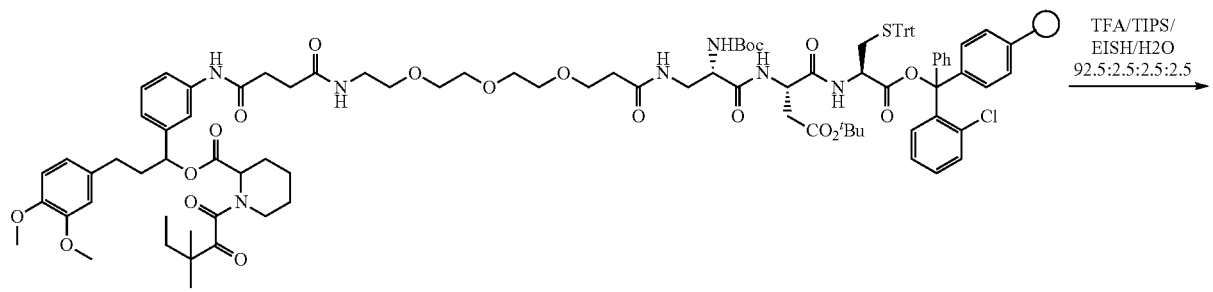

-continued
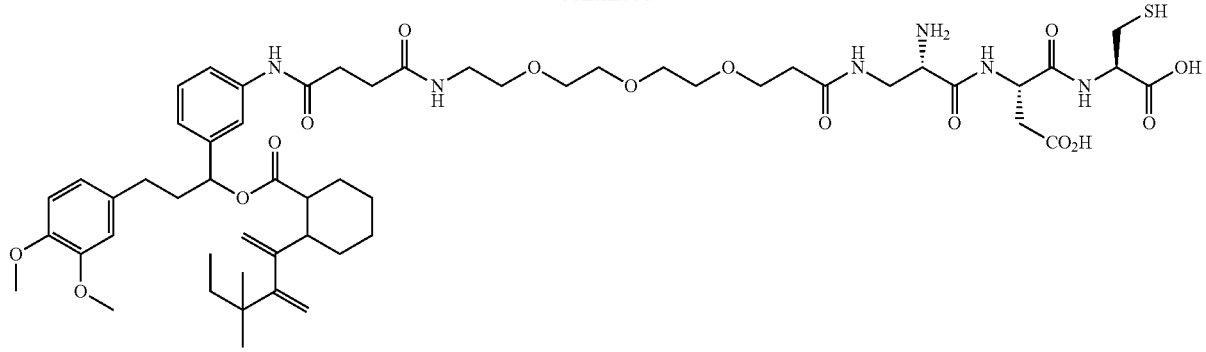
Chemical Formula: $C_{53}H_{77}N_7O_{18}S$
Exact Mass: 1131.50
Molecular Weight: 1132.29
SLF-Tubulysin:
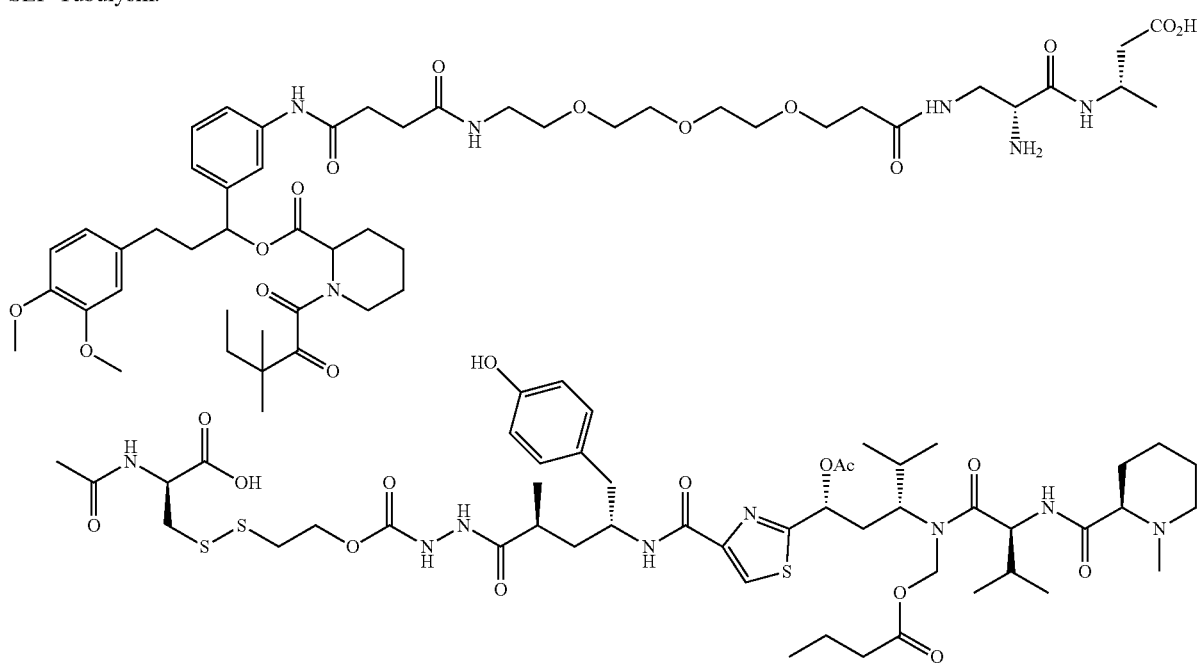
Molecular Weight: 2078.48
Synthesis Procedure:
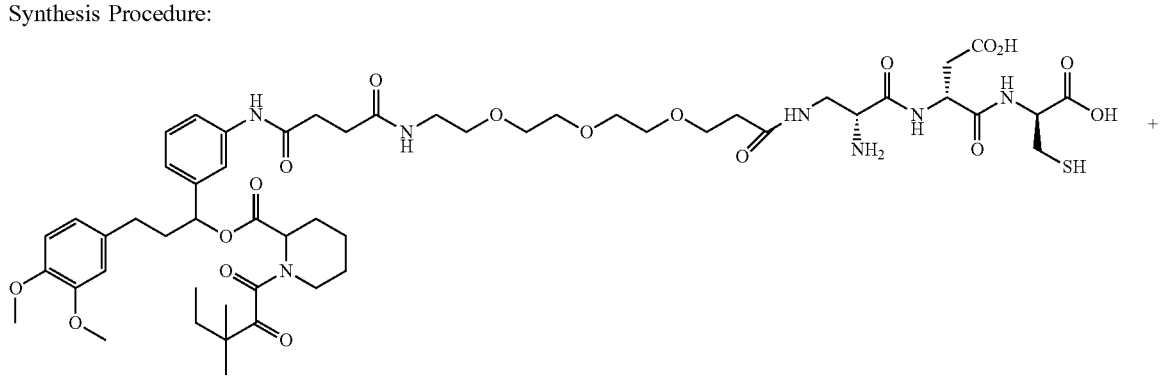
Chemical Formula: $C_{53}H_{77}N_7O_{10}S$
Exact Mass: 1131.50
Molecular Weight: 1132.29

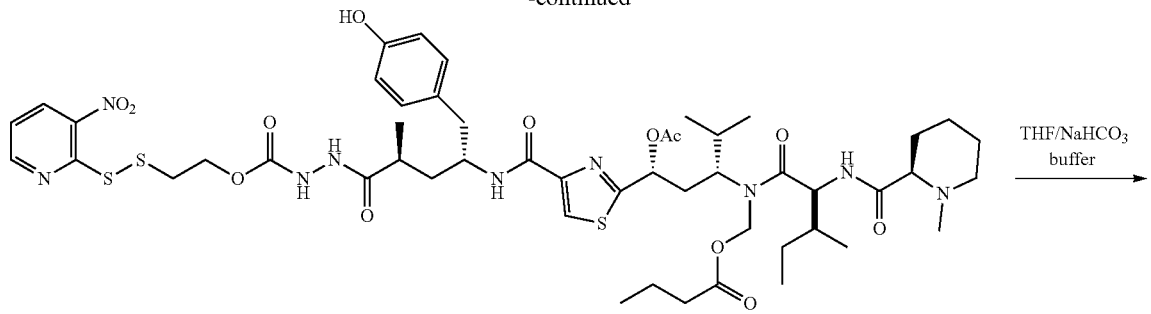
Exact Mass: 1101.43
Molecular Weight: 1102.35
THF/NaHCO₃ buffer →
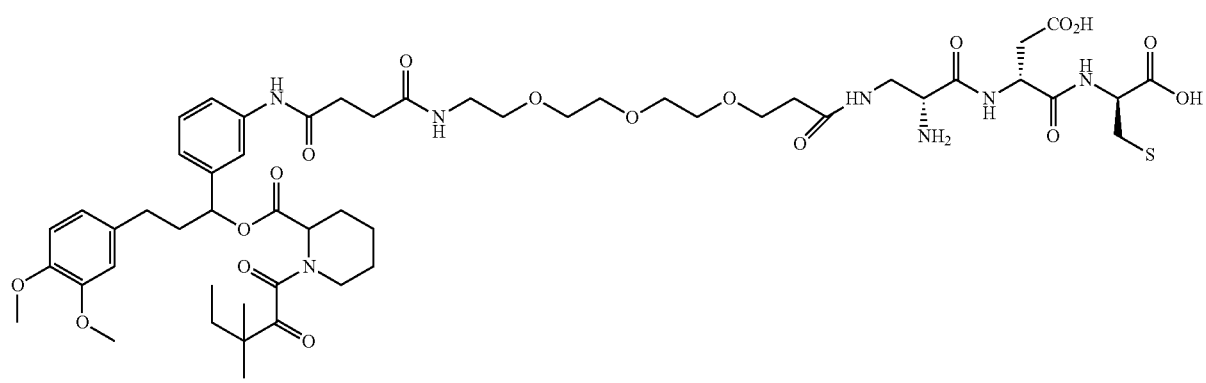
Molecular Weight: 2078.48
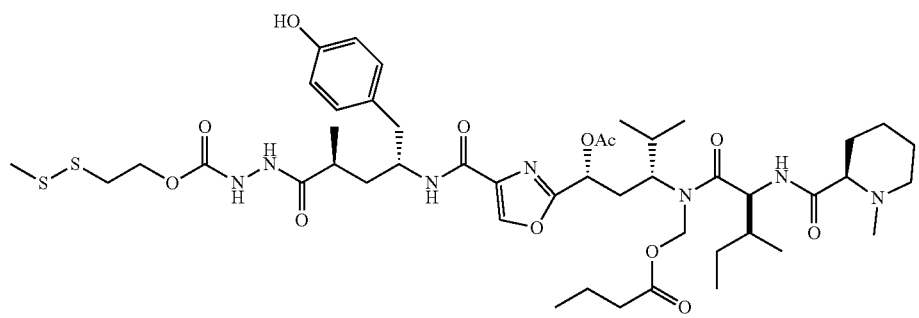
FITC-AF647:
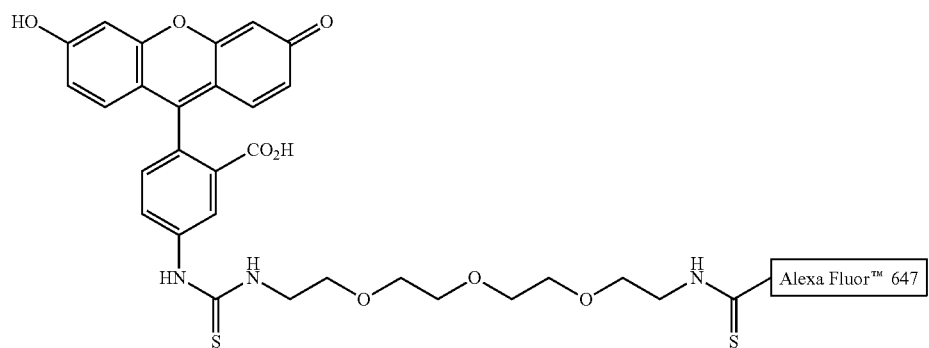 [SMILES: CC(=S)NCCOCCOCCOCCNC(=S)Nc1ccc(-c2c3ccc(=O)cc-3oc3cc(O)ccc23)c(C(=O)O)c1]

Synthesis Procedure:
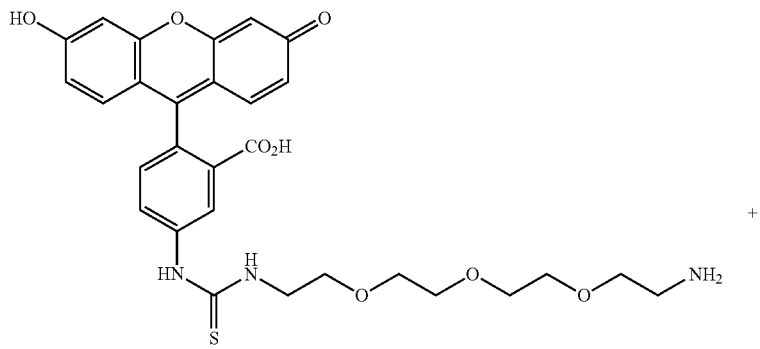
Chemical Formula: $C_{29}H_{31}N_3O_8S$
Exact Mass: 581.18
Molecular Weight: 581.64
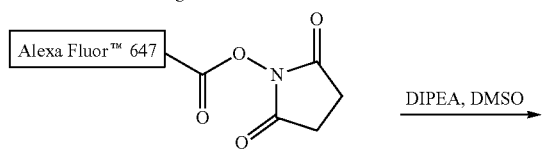
Alexa Fluor™ 647 NHS Ester (Succinimidyl Ester)
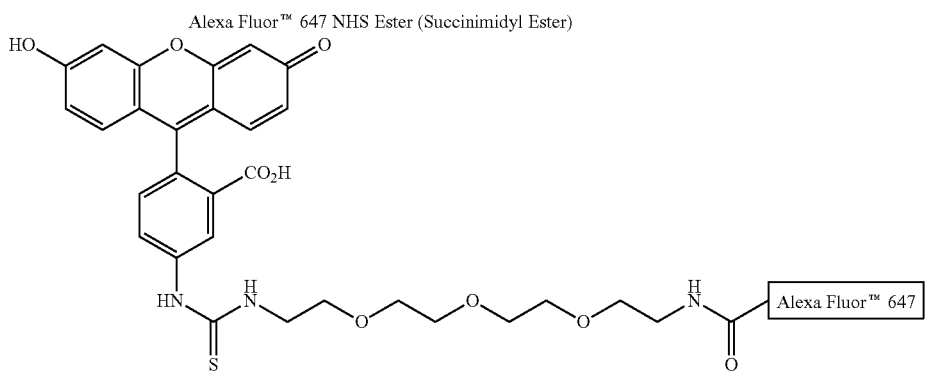
FITC-DM4:
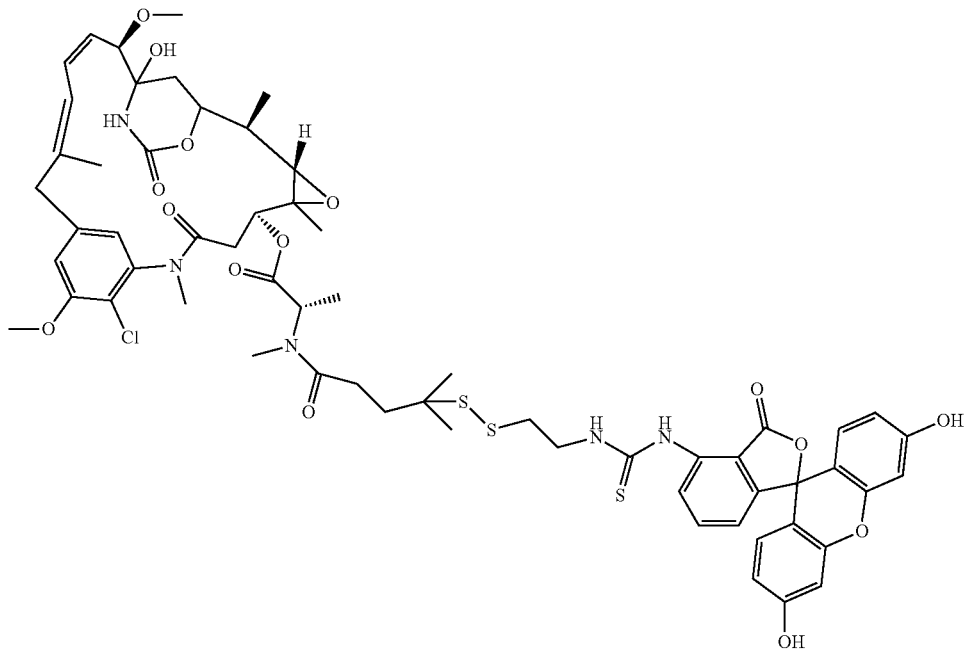 [SMILES: COc1cc2cc(c1Cl)N(C)C(=O)C[C@H](OC(=O)[C@H](C)N(C)C(=O)CCC(C)(C)SSCCNC(=S)Nc1cccc3c1C(=O)OC31c3ccc(O)cc3Oc3cc(O)ccc31)C1(C)O[C@H]1[C@H](C)C1CC(O)(NC(=O)O1)[C@H](OC)/C=C\C=C(\C)C2]

Synthesis Procedure:
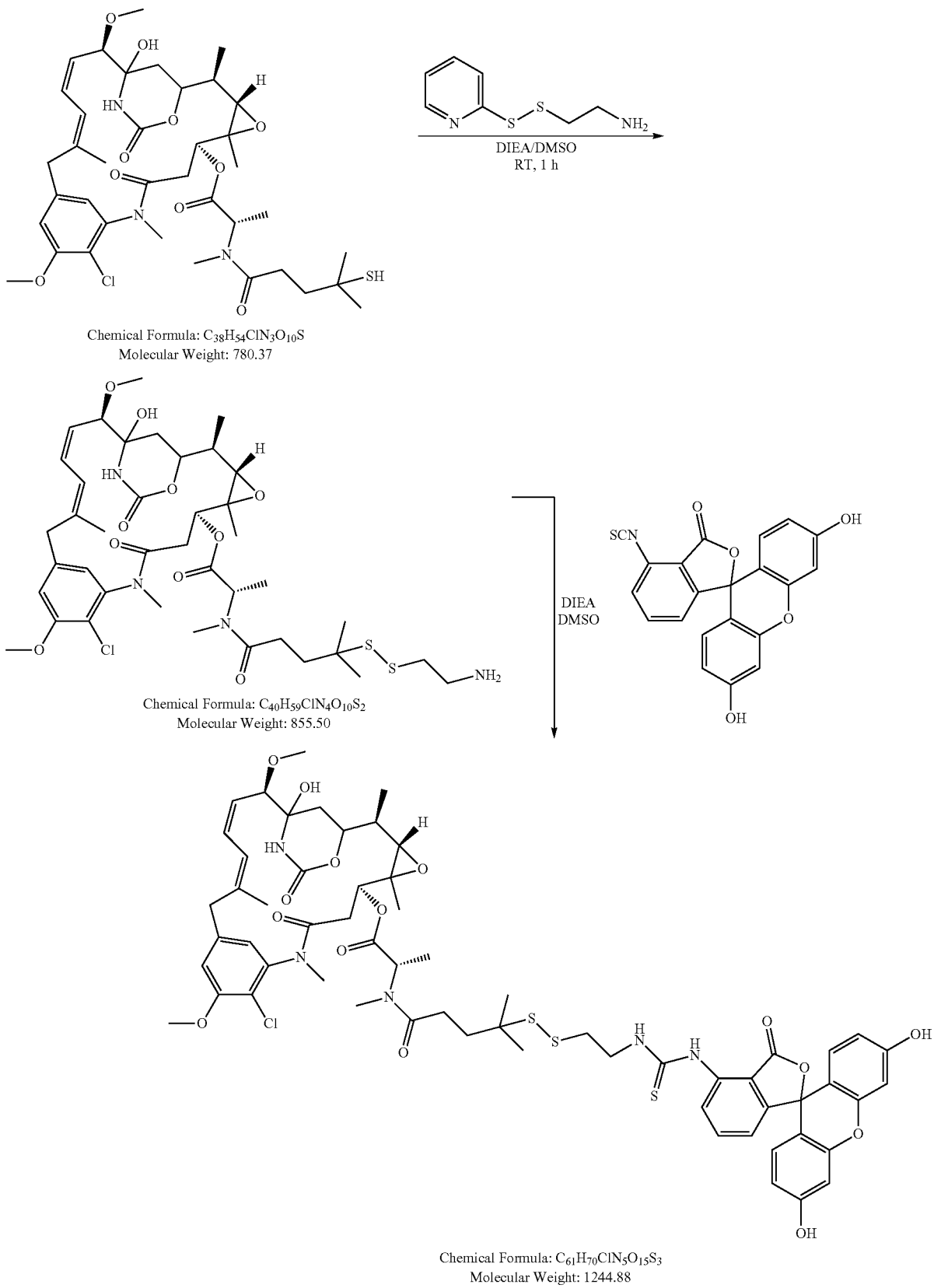

Procedure: DM4 (1.0 equiv.) in dimethylsulfoxide was reacted with 2-(pyridin-2-yldisulfaneyl) ethan-1-amine (1.0 equiv.) and diisopropylethylamine (3.0 equiv.) for 1 h at room temperature. The resulting crude product was then reacted with FITC (1.0 equiv.) and the reaction mixture was stirred for 1 h. The final FITC-DM4 conjugate was isolated after purification on preparative reverse-phase HPLC with a UV detector (monitored at wavelength of 280 nm). The crude product was loaded onto an Xterra RP18 preparative HPLC column (Waters) and eluted with gradient conditions starting with 95% 5 mM sodium phosphate (mobile phase A, pH7.4) and 5% acetonitrile (mobile phase B) and reaching 0% A and 100% B in 10 min at a flow rate of 12 mL/min. Retention time of the product peak=4.23 min during the gradient (0-100% B) in a 7 min analytical HPLC-MS analysis. ESI m/z=1244.8. Abbreviations: FITC fluorescein isothiocyanate; HPLC=High Performance Liquid Chromatography.

FITC-Tub

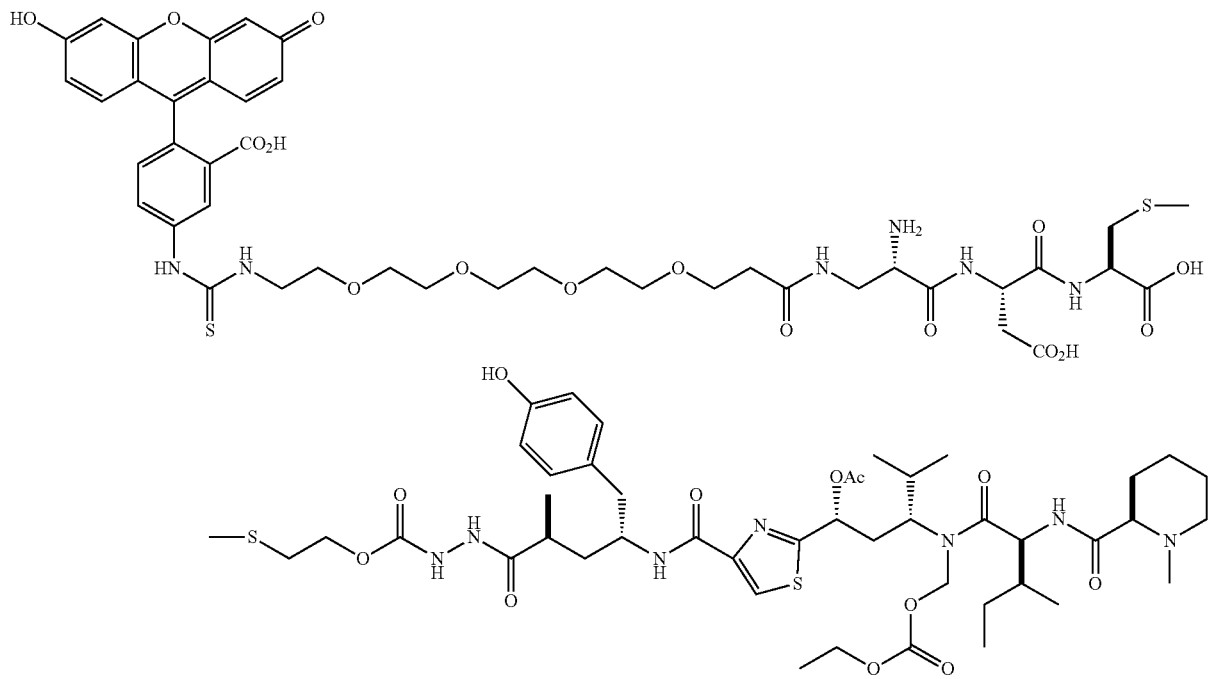

Chemical Formula: $C_{87}H_{117}N_{13}O_{27}S_4$
Exact Mass: 1903.71
Molecular Weight: 1905.20

Synthesis Procedure:

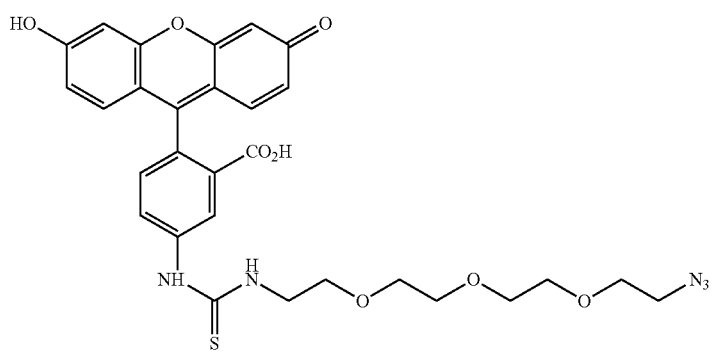

Chemical Formula: $C_{29}H_{29}N_5O_8S$
Exact Mass: 607.17
Molecular Weight: 607.64

-continued
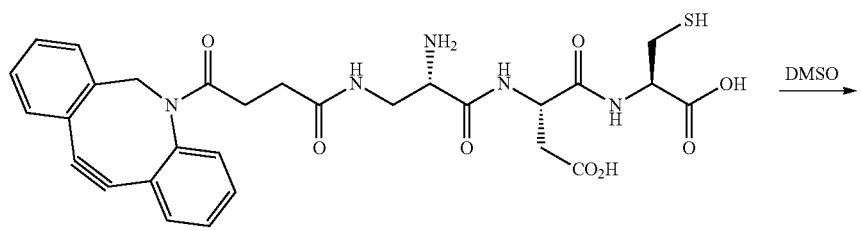
Chemical Formula: C$_{29}$H$_{31}$N$_5$O$_8$S
Exact Mass: 609.19
Molecular Weight: 609.65
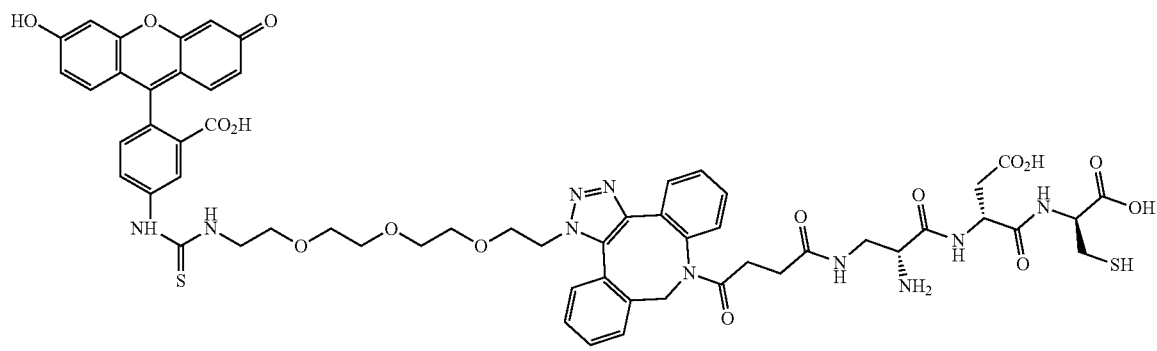
Chemical Formula: C$_{58}$H$_{60}$N$_{10}$O$_{16}$S$_2$
Exact Mass: 1216.36
Molecular Weight: 1217.29
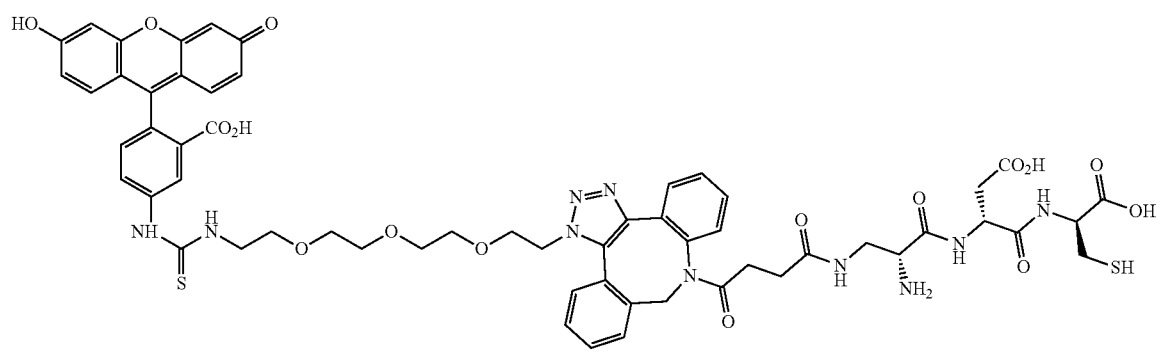
Chemical Formula: C$_{58}$H$_{60}$N$_{10}$O$_{16}$S$_2$
Exact Mass: 1216.36
Molecular Weight: 1217.29
+
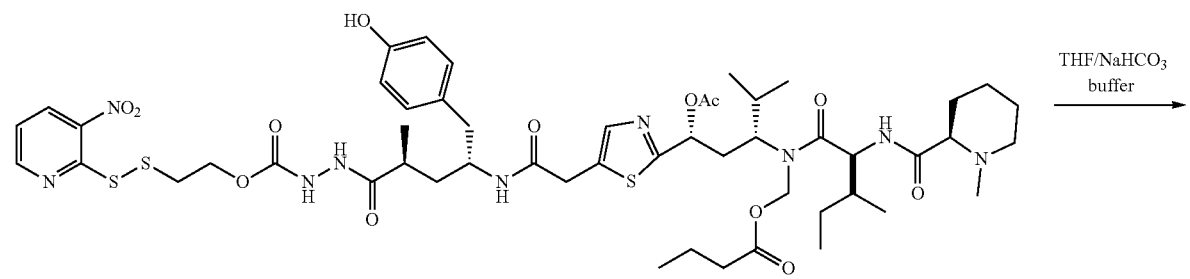
Exact Mass: 1101.43
Molecular Weight: 1102.35

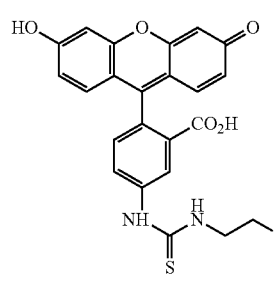
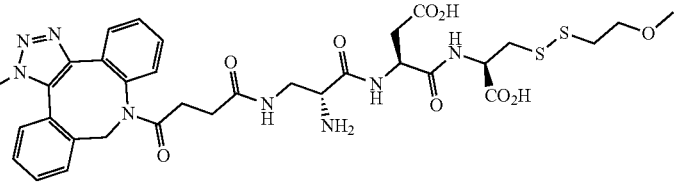
Exact Mass: 2161.80
Molecular Weight: 2163.48
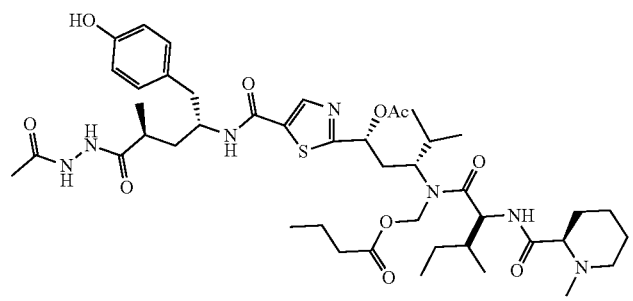
FITC-EC20
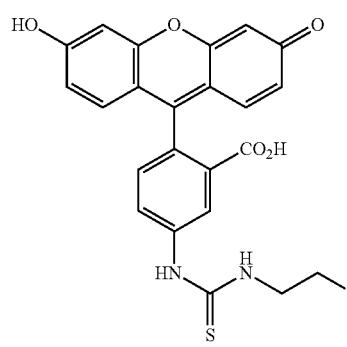
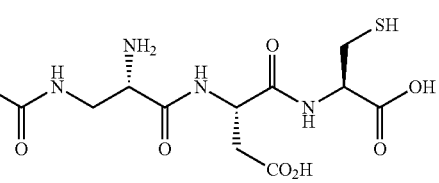
Chemical Formula: $C_{42}H_{50}N_6O_{16}S_2$
Exact Mass: 958.27
Molecular Weight: 959.01

Synthesis Procedure:
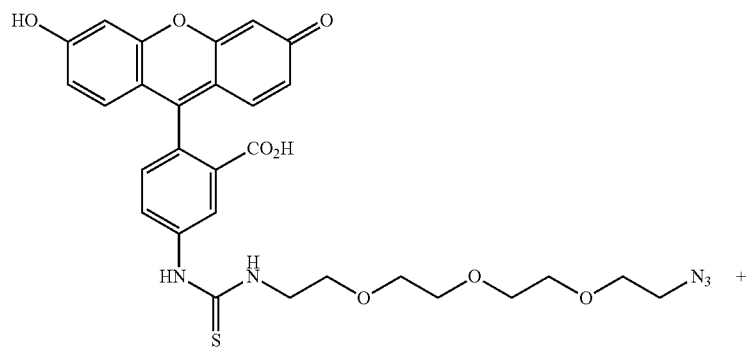
Chemical Formula: C₂₉H₂₉N₅O₈S
Exact Mass: 607.17
Molecular Weight: 607.64
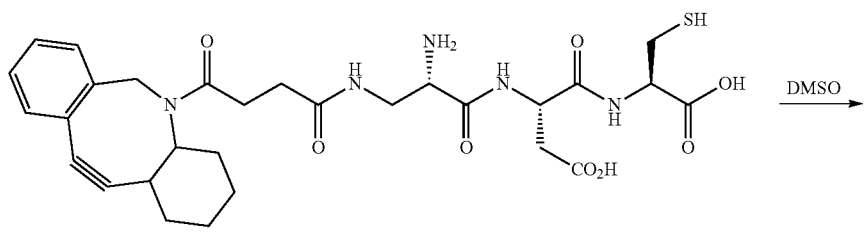
Chemical Formula: C₂₉H₃₁N₅O₈S
Exact Mass: 609.19
Molecular Weight: 609.65
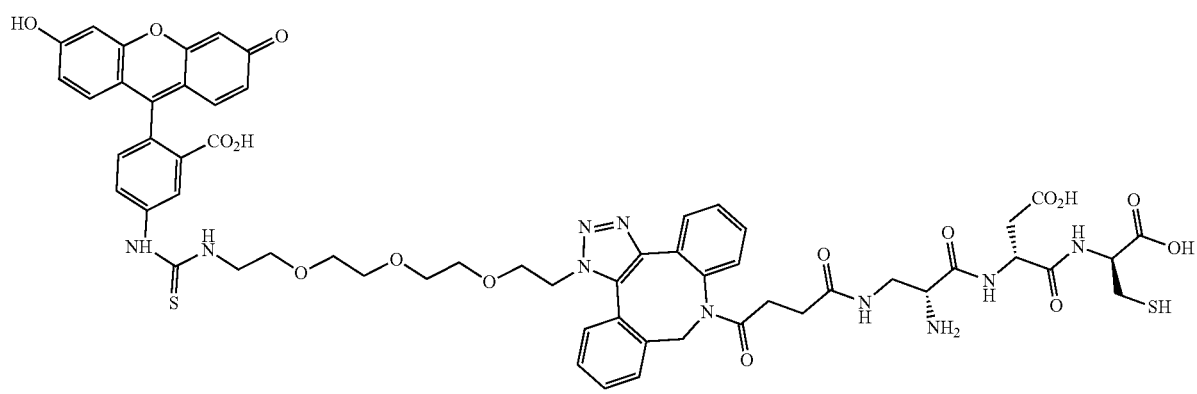
Chemical Formula: C₅₈H₆₀N₁₀O₁₆S₂
Exact Mass: 1216.36
Molecular Weight: 1217.29

FITC-Dasatinib
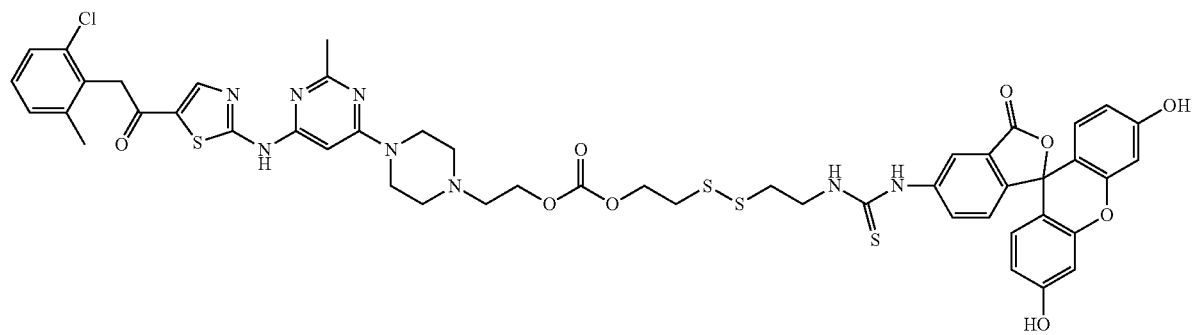
Molecular Weight: 1055.65
Synthesis Procedure:
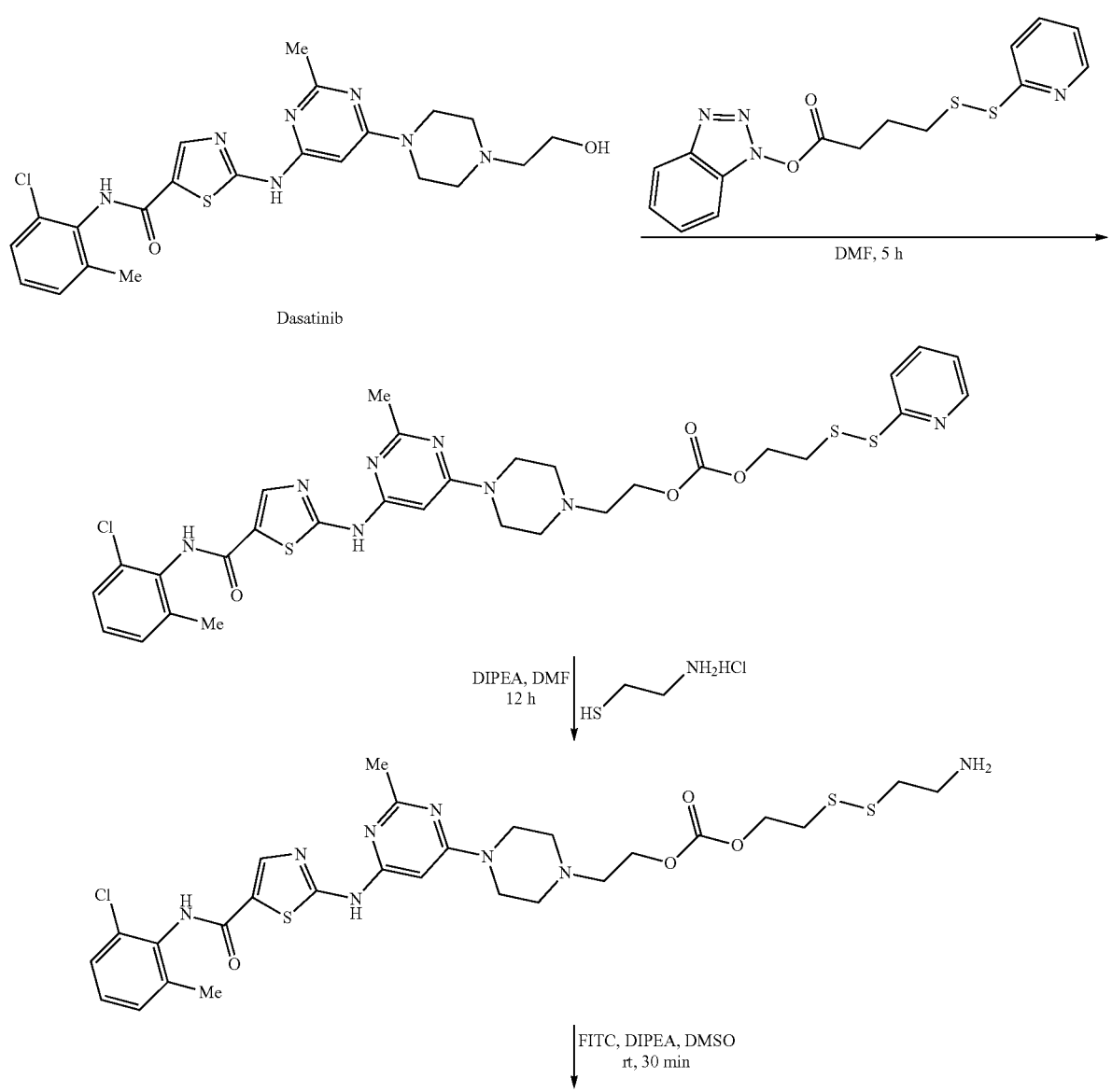

-continued

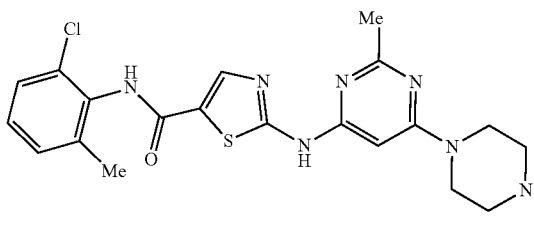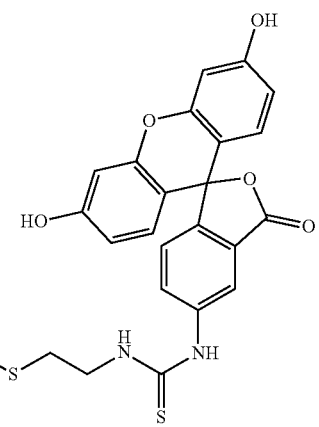

The Experiment Procedure:
Cell Culture

293TN cells were cultured in DMEM with 10% FBS, no antibiotic for lentivirus packaging. Raji and Jurkat cells were cultured in RPMI-1640 with 10% FBS, 10% Penicillin/ Streptomycin. Primary human T cells were isolated from hPBMC using ficoll, enriched by negative selection with EasySep™ Human T Cell Enrichment Kit (19051, Stemcell Tech), activated by Dynabeads CD3/CD28 (11161D, Thermo Fisher) for 1 days, cultured with TexMACS medium supplemented with 30IU hIL2 (130-097-745, Miltenyi Biotec Inc.). T cells were cryopreserved in RPMI-1640 with 20% human AB serum (HP1022, Valley Biomedical) and 10% DMSO.

Lentivirus Packaging

Pantropic VSV-G pseudotyped lentivirus was produced via transfection of 293TN cell with the transgene expression vector and packaging plasmid mix (CPCP-K2A, Cellecta) using Lipofectamine 2000. At 24 h, viral supernatant was harvested, concentrated and then added to certain cell lines or the primary T cells that were thawed the same day. For T cell transduction, cells were centrifuged at 2500 rpm for 90 mins, 37 degree after adding the virus supernatant and 8 ug/ml polybrene.

Binding Assay

For binding assay, cells were incubated with ligand-dye alone or with ligand-dye and free ligands (100×, preincubated for 30 min) for 30 min, at 4 degree. Cells were washed 3 times after incubation, and re-suspended in 2% FBS PBS, 7-AAD were added to gate out the dead cells. FRET imaging of FK506-Rhodamine and FA-S0456: To understand the occupation of the fusion receptor, FKBP-FRa+ jurkat cells are incubated with FA/FA-S0456, FK506/FK506-Rhodamine at the indicated sequence and concentration. FRET is visualized by the loss of intensity of FA-Rhodamine as its energy transferred to FA-OTL38 on the same or nearby receptor, detected by BD Fortessa flow cytometer. Results were analyzed using Flow Jo software.

PI-PLC Treatment to Release the GPI Anchored Protein $1×10^5$ cells were incubated with 5mU or 50mU PI-PLC (P5542-5UN, Sigma) in digestion buffer (2% BSA) at 37 degree for 30 min; after incubation, cells were washed three times by PBS and then incubated with ligand-dye for 30 min on ice.

Cell Viability Assay

Cells were seeded to 96 well plate and incubated with different concentration of certain ligand-cytotoxic drug for 2 h, with or without 100× preincubation of the free ligand competition. After 2 h incubation, cells were washed by warm medium 3 times and replenished with fresh medium. After 72 h, cell number were tested by CellTiter-Glo® assay (G7570, Promega) or quantified by ligand-dye staining of receptor positive cell.

CAR T Cell Lysis Effect $1×10^5$ CAR T and certain number of Raji cell were co-incubated in 96 well plate, according to the E:T ratio, with or without the treatment drug. After 24 h, 100 ul supernatant were taken out for LDH assay. Lysis percentage were calculated as (treatment group-CAR T only)/(maximum lysis-CAR T only) %

Exhaustion of CAR T Cell $1×10^6$ Raji cell were repeated added to $1×10^6$ CAR T cell in 24 well plate every 12 h, without changing the medium. Exhaustion status were characterized by lower lysis effect and higher expression of co-inhibitory molecules: PD-1, LAG-3 and Tim-3.

In Vivo Ablation of the Fusion Receptor Positive CAR T by Ligand-Cytotoxic Drug $4×10^5$ luc+Raji cells were iv injected into the NSG mice. After 6 days, $1×10^7$ fusion receptor positive CAR T cells were iv injected. On Day 8, ligand-cytotoxic drug (0.5 umole/kg, 1umole/kg) were iv injected once. IL2, INFr were measured by ELISA using serum sample taken every 3 days after the CAR T injection. CAR T cell in peripheral blood were counted by flow cytometry.

In Vivo Modulation of Fusion Receptor Positive CAR T by Ligand-Drug $4×10^5$ luc+Raji cells were iv injected into the NSG mice. After 6 days, $1×10^7$ fusion receptor positive CAR T cells were iv injected. On Day 7, ligand-drug drug (0.5 umole/kg, 1 umole/kg) were iv injected once. In the case of CAR T exhaustion model, $1×10^5$ CAR T were iv injection on Day 6, once the CAR T population were shown in peripheral blood and tumor burden is not stabilized and continue to increase, ligand-drug (0.5 umole/kg, 1 umole/kg) were iv injected.

In Vivo Imaging and Tracking of Fusion Receptor Positive CAR T $2×10^6$ Raji were subcutaneously injected to the right should of NSG mice. 14 days later, $1×10^7$ fusion receptor positive CAR T were iv injected. On Day 16, animals were administrated 99mTc-bound conjugates (10 nmol, 150 μCi) by iv injection and imaged by SPECT imaging machine.

EXAMPLES

1. Design of Fusion Protein and its Expression
1.1 Design of FKBP-FR Fusion Receptor (SEQ ID NO:2)

Figure 4C:
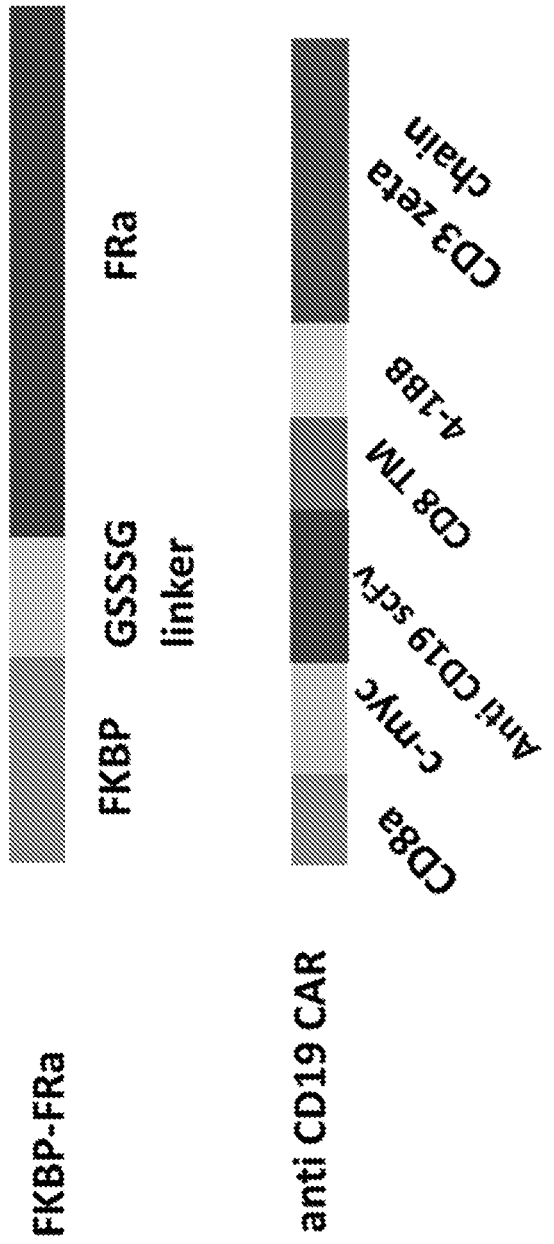
FIG. 4: a. pWPI expression vector map with FKBP-FRa insert (hFRa 1-24: red, FKBP: yellow, hFRa 25-258: red) b. FKBP-FRa transduced K562 cells show a higher band around 50 kDa (37 kDa for FRa plus 12 kDa for FKBP) compare to FRa positive KB cells and non-transduced K562 cells, c. payload carrier construct and CAR T construct design d. The construct design of FKBPFR3GS (noted as FF3). From N terminal to C terminal, it has 1-24 aa of human FRa as the signal peptide, human FKBP protein, three Gly-Ser linker and then 25-258 aa of human FRa. In FKBPFRIGS (noted as FF1), the three Gly-Ser liner of FF3 is substituted with one Gly-Ser linker with other parts unchanged, e. The construct design of 4m5.3FR. From N terminal to C terminal, it has hCD8 signal peptide, scFv of 4M5.3 antibody against FITC, GS linker, 25-258aa of human FRa.

Synthesis of FK506 derivatives: FK506-Rhodamine and FK506-tubulysin Synthesis was described in materials and methods section.

hFRa is a GPI anchored membrane protein, which has 24 amino acids on the N terminal as a signal peptide. In order to preserve the membrane presentation and internalization property, we choose to use the full length of FRa, and incorporate the hFKBP sequence as well as a flexible peptide linker (SGGGS) between T24 and R25 of hFRa (FIG. 4a). The flexible linker is chosen to be resistant to common enzyme digestions in human body. The whole sequence is then inserted into a pWPI lentivirus expression vector, with EF1a as the desired promoter for protein expression in transduced T cell.

1.2 Expression of FKBP-FR Fusion Receptor in Transduced Cells

Expression of FKBP-FRa is confirmed by western blot in lentivirus transduced K562. Transduced K562 cell lysis shows specific band around 50 kDa compared to non-transduced cells against hFRa antibody (FIG. 4b).

1.3 Construction of Fusion Protein of FKBPFR3GS (Noted as FF3)

See FIG. 4d (SEQ ID NO: 12). From N terminal to C terminal it has 1-24 aa of human FRa as the signal peptide, human FKBP protein, three Gly-Ser linker and then 2-258 aa of human FRa. In a construct design of FKBPFRIGS (noted as FF1), the three Gly-Ser linker of FF3 is substituted with one Gly-Ser linker with other parts unchanged. As will be shown in the binding assays, increasing linker length reduces the interference between the two components in the fusion protein.

1.4 Construction of Fusion Protein of FITC-svFv-FR with GS Linker.

See FIG. 4e. The construct is also named as 4M5.3 FR (SEQ ID NO: 13). From N-terminal to C-terminal, it has hCD8 signal peptide, svFv of 4M5.3 (against FITC), GS linker, 25-258 aa of human FRa.

1.5. In Vivo Noninvasive Tracking of FKBP-FRa/FKBPtFRa Positive Cells by FK506-99mTc PET Imaging For CAR T cell model, 1×10⁶ KB cells are subcutaneously implanted in NSG (Jackson laboratory). After the tumor reaches 100 mm³, 15 million anti-FITC CAR+ FKBP-FRa+ or anti-FITC CAR+ FKBP-FRa− human T cells are intravenously injected to the mice. FITC-FA is injected at the indicated days to induce the proliferation of the CAR T. Mice are imaged every two days after the CAR T implantation by the following procedure. At the day of imaging, FK506-EC20 head is formulated with 99mTc according to previous report. 200 uCi 99mTc in 100 ul solution is i.v. injected to each mouse and whole body image is taken by MiLab PET/CT, focusing on the tumor area, spleen and lymph nodes. 3D images are reconstructed by PMOD software. After the last imaging at around day 10 after CAR T implantation, mice are euthanized and 99mTc distribution in each organ are counted by gamma counter.

For Hematopoietic Stem Cell transplantation model, humanized NSG mice are generated as reported before. 10 million CD34+ FKBP-FRa+ hHSC are i.v infused into the humanized NSG mice. 4 months later, whole body image is taken using FK506-99mTc as mentioned above, focusing on the bone marrow and spine.

2. FKBP-FRa Fusion Receptor Specifically Binds and Internalizes FK506-Payload 2.1 FKBP-FRa Fusion Receptor Specifically Binds FK506-Rhodamine For binding assay, cells were incubated with ligand-dye alone or with ligand-dye and free ligands (100×, preincubated for 30 min) for 30 min, at 4 degree. Cells were washed 3 times after incubation, and re-suspended in 2% FBS PBS, 7-AAD were added to gate out the dead cells. BD Fortessa flow cytometer were used. Results were analyzed using FlowJo software.

2.2. Binding of FK506-Rhodamine by FKBP-FRa Fusion Receptor (FRET Imaging of FK506-Rhodamine and FA-S0456)

To understand the occupation of the fusion receptor, FKBP-FRa+ jurkat cells are incubated with FA/FA-S0456, FK506/FK506-Rhodamine at the indicated sequence and concentration. FRET is visualized by the loss of intensity of FA-Rhodamine as its energy transferred to FA-OTL38 on the same or nearby receptor, detected by BD Fortessa flow cytometer.

Figure 5:
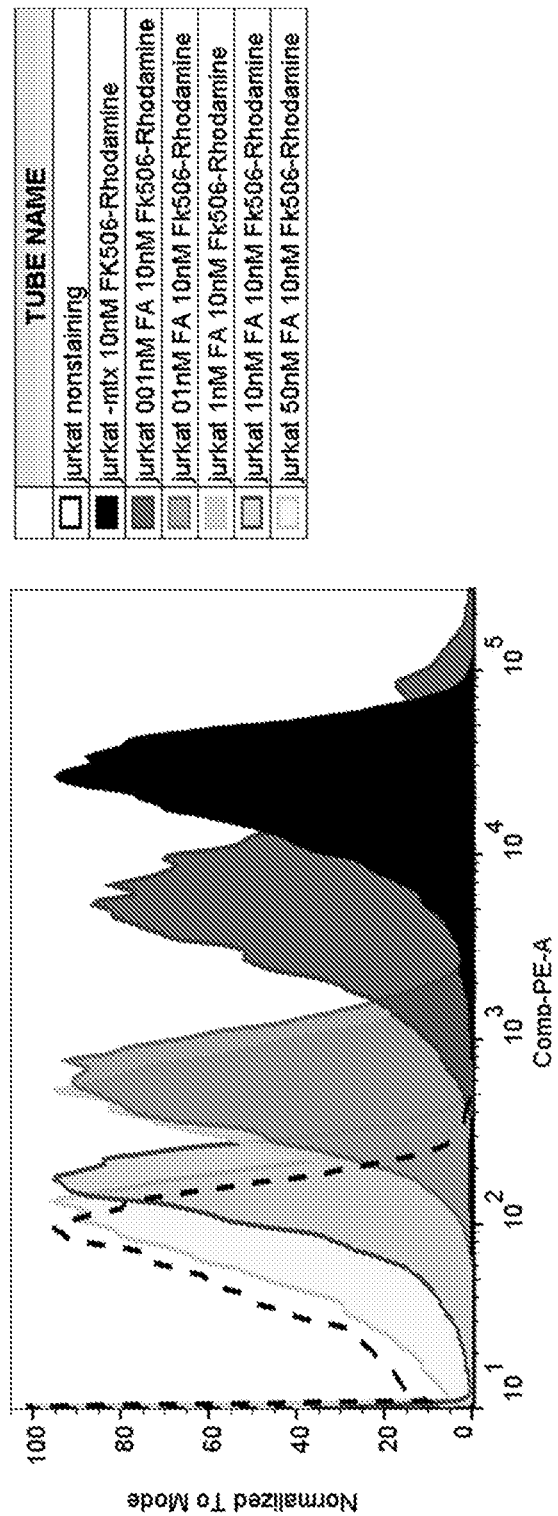
FIG. 5. Interference between the FR and FKBP in FKBP-FRIGS fusion receptor. Binding of Folate acid in FKBP-FRIGS fusion protein blocks the binding of FK506-Rhodamine at as low as 0.01 nM and totally abolish FK506-Rhodamine binding at 50 nM.

FIG. 5 shows binding of Folate acid in FKBPFR1GS fusion protein blocks the binding of FK506-Rhodamine at as low as 0.01 nM and totally abolishes FK506 Rhodamine binding at 50 nM.

Figure 6:
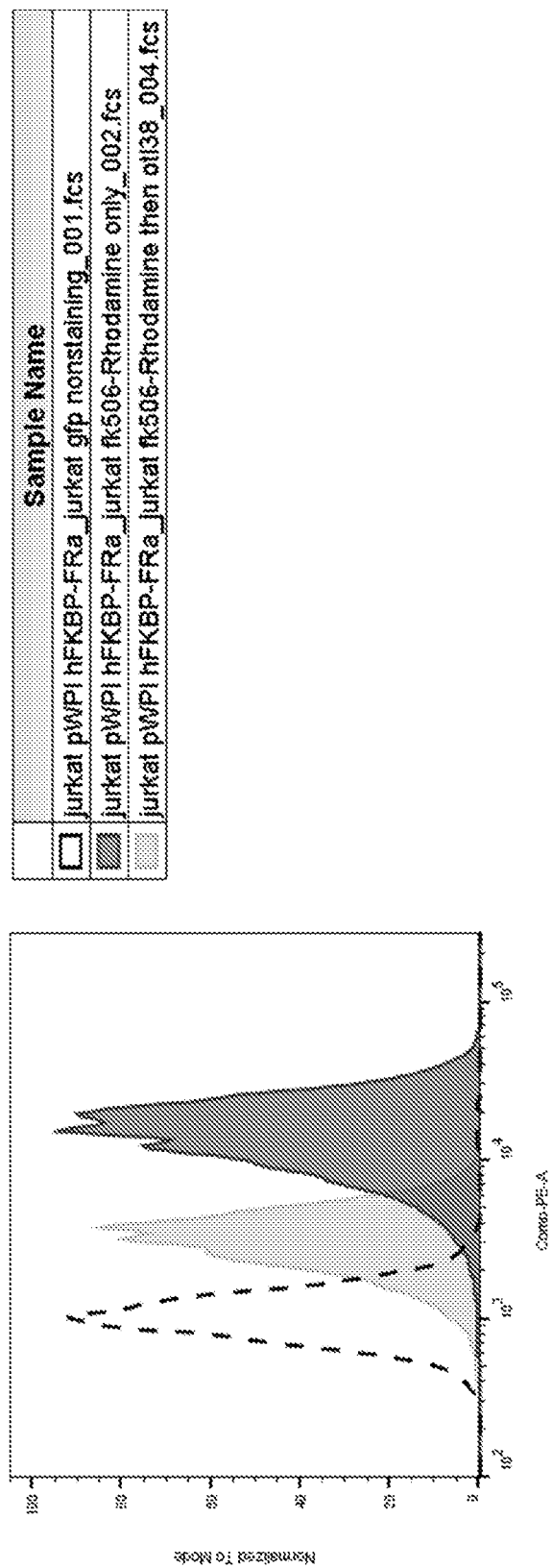
FIG. 6. FKBPFRIGS jurkat cell shows decreased FK506-Rhodamine intensity after binding to OTL38. FRET from FK506-Rhodamine (donor) to OTL38 (FA-S0456, acceptor, ex/em: 774/794 nm) within the fusion receptor indicates the interaction between FR and FKBP.

FIG. 6 shows FKBPFR1GS jurkat cells have decreased FK506-Rhodamine intensity after binding to OTL38, a folate receptor targeted dye. FRET from FK506-Rhodamine (donor) to OTL38 (FA-S0456, acceptor, ex/em: 774/794 nm) indicates the interaction between FR and FKBP within the fusion receptor.

Figure 7:
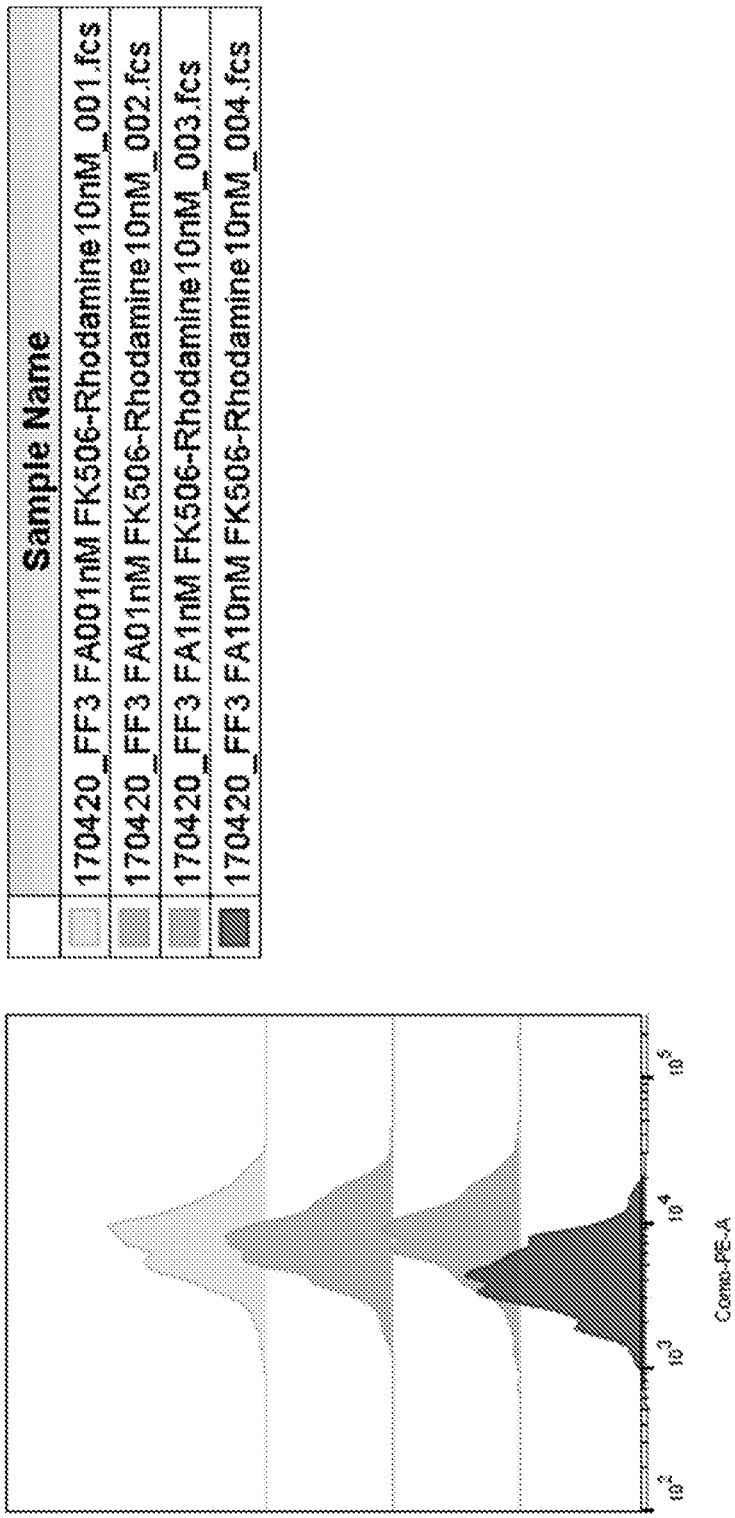
FIG. 7. Increasing the linker length between FKBP and FR significantly lowers the interference between the two parts. Compare to FF1 (1GS between FKBP and FR), FF3 (3GS between FKBP and FR) preserves the binding of FK506-Rhodamine in the presence of 10 nM FA, which is comparable to the physiological concentration of FA in human body.

FIG. 7 shows increasing the linker length between FKBP and FR significantly lowers the interference between the two components of the fusion protein. Compare to FF1 (1GS between FKBP and FR), FF3 (3GS between FKBP and FR) preserves the binding of FK506-Rhodamine in the presence of 10 nM FA, which is comparable to the physiological concentration of FA in human body.

2.3. Release of GPI Anchored FF3 Fusion Receptor

Figure 8:
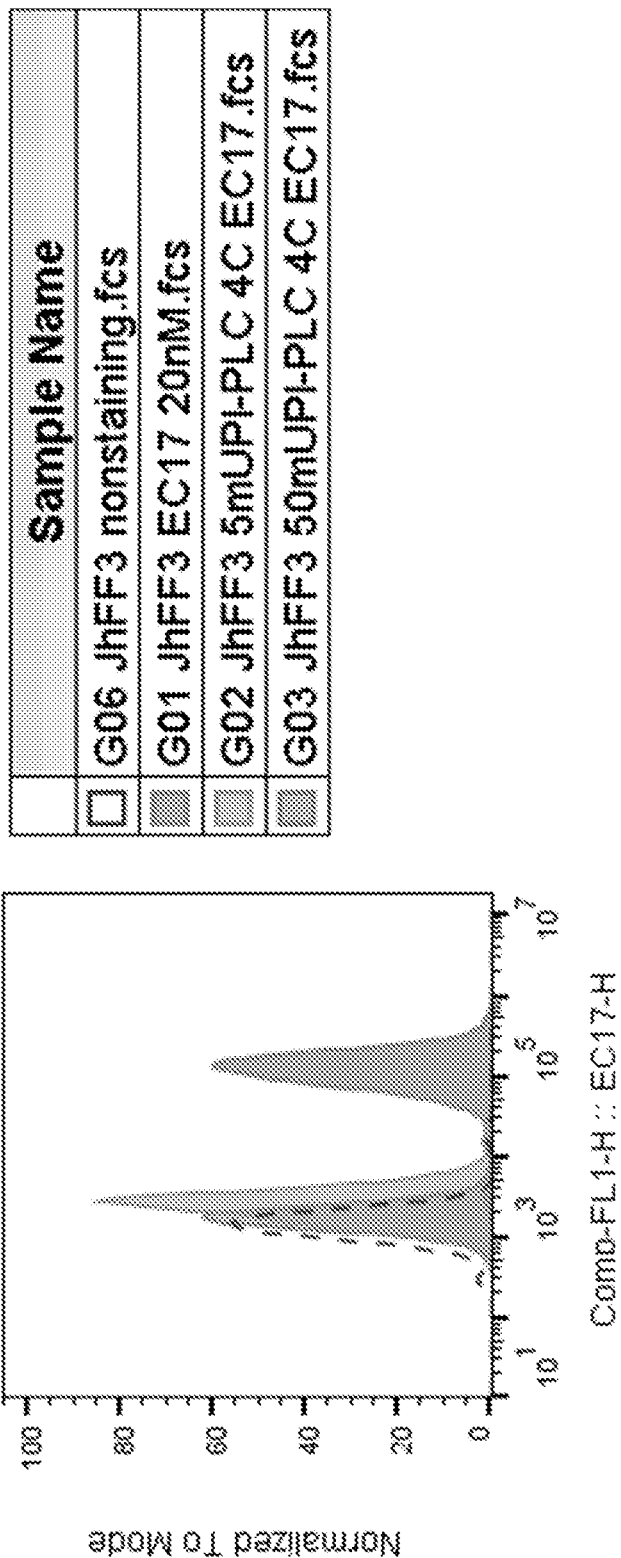
FIG. 8. PI-PLC treatment releases the GPI anchored fusion receptor FF3. Jurkat T cell with FF3 fusion receptor shows saturated binding with 20 nM FA-FITC (EC17), while after 5 mU PI-PLC or 50mU PI-PLC treatment, the FA-FITC loses binding to the cell, which indicates the release of the GPI anchored FF3 fusion receptor.

Using PI-PLC treat T cells having FF3 fusion protein resulted the release of GPI anchored receptor FF3. Jurkat T cell with FF3 fusion receptor shows saturated binding with 20 nM FA-FITC (EC17), while after 5mU PI-PLC or 50mU PI-PLC treatment, the FA-FITC loses binding to the cell, which indicates the release of the GPI anchored FF3 fusion receptor. See FIG. 8.

2.4 Fusion Protein FKBPFR3GS in Human T Cell Retains FR Binding Property

Figure 9:
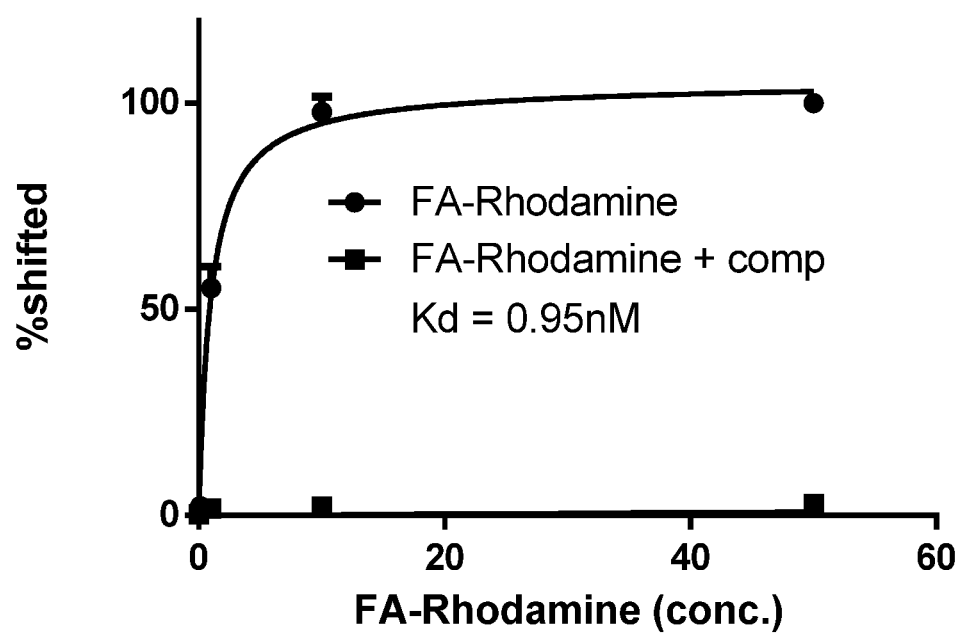
FIG. 9. FA-Rhodamine binding curve in FKBPFR3GS fusion receptor. FKBPFR3GS fusion receptor that stably expressed on human T cell can bind to folate acid derivative (FA-Rhodamine) with high affinity (Kd=0.95 nM), which is comparable to the affinity of FA-Rhodamine in FR+KB cell (Kd around 1 nM). Therefore, the binding property of FR in the fusion receptor is preserved.

FA-Rhodamine binding curve is shown in FKBPFR3GS fusion receptor. FKBPFR3GS fusion receptor that stably expressed on human T cell can bind to folate acid derivative (FA-Rhodamine) with high affinity (Kd=0.95 nM), which is comparable to the affinity of FA-Rhodamine in FR+KB cell (Kd around I nM). Therefore, the binding property of FR in the fusion receptor is preserved. See FIG. 9.

2.5 Fusion Protein FKBPFR3GS in Human T Cell Retains FKBP Binding Property

Figure 10:
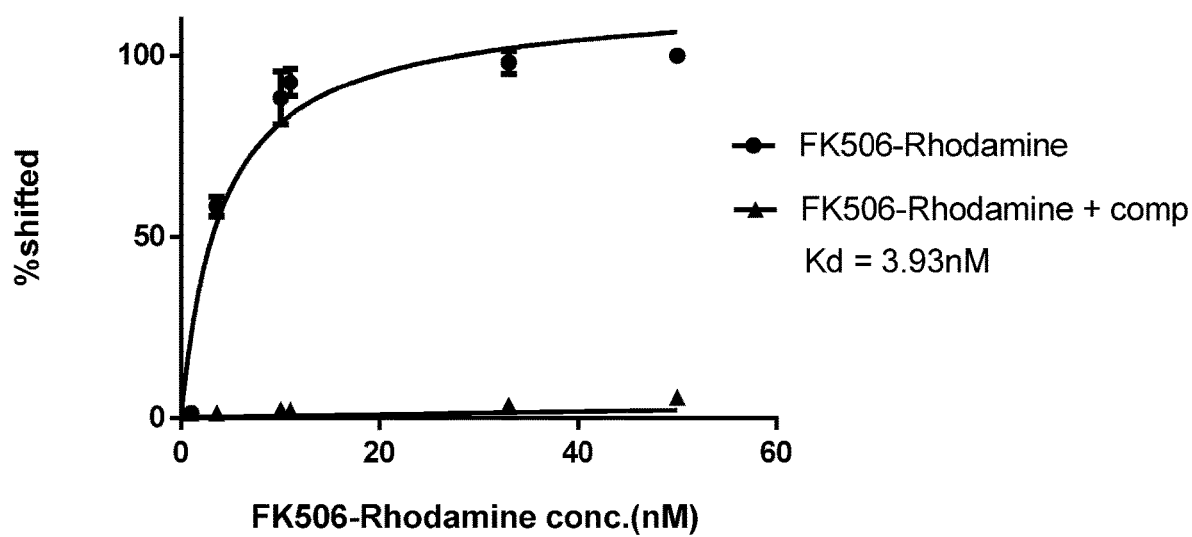
FIG. 10. FK506-Rhodamine binding curve in FKBPFR3GS fusion receptor. FKBPFR3GS fusion receptor that stably expressed on human T cell is able to bind to FK506 derivative (FK506-Rhodamine) with high affinity (Kd=3.93 nM), which means the binding property of FKBP in the fusion receptor is preserved.

FK506-Rhodamine binding curve in FKBPFR3GS fusion receptor. FKBPFR3GS fusion receptor that stably expressed on human T cell is able to bind to FK506 derivative (FK506-Rhodamine) with high affinity (Kd=3.93 nM), which means the binding property of FKBP in the fusion receptor is preserved. See FIG. 10.

2.6 SLF-FITC Binds to FKBPFR3GS Fusion Receptor with Relative High Binding Affinity (Kd=62 nM)

Figure 11:
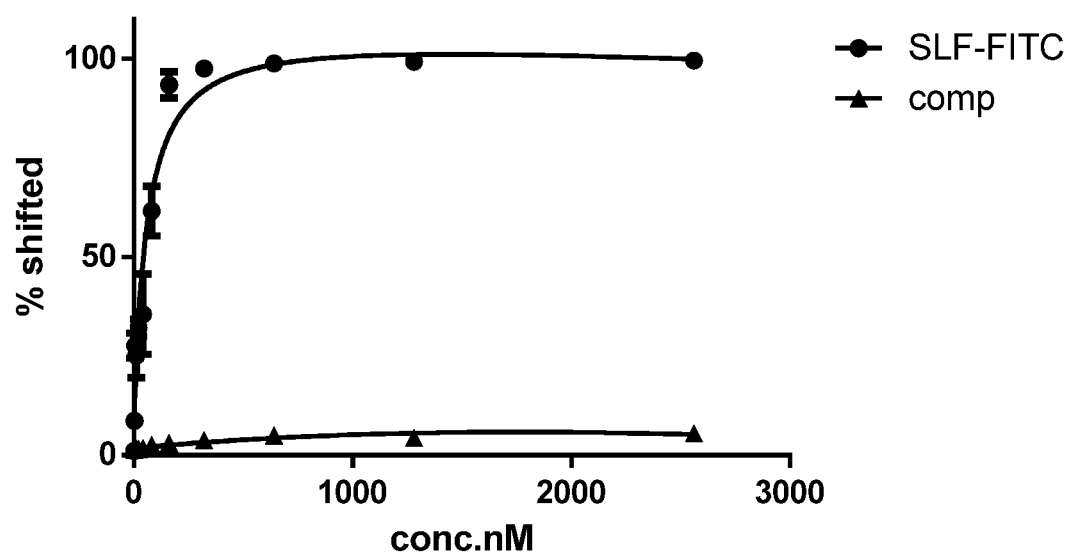
FIG. 11. SLF-FITC binds to FKBPFR3GS fusion receptor with relatively high binding affinity (Kd=62 nM), while competition with free SLF (100×, preincubation) blocks this binding. SLF, a mimic of FK506, presents a 10 times lower binding affinity to FKBPFR fusion receptor, compare to the parent ligand FK506, which is consistent with previous report.

Competition of free SLF (100, preincubation) blocks SLF-FITC binding. SLF, a mimic of FK506, presents a 10 times lower binding affinity to FKBPFR fusion receptor, compared to the parent ligand FK506. See FIG. 11 and compare with FIG. 10.

2.7 Binding Curve of FA-Rhodamine in 4M5.3FR Fusion Receptor.

Figure 12:
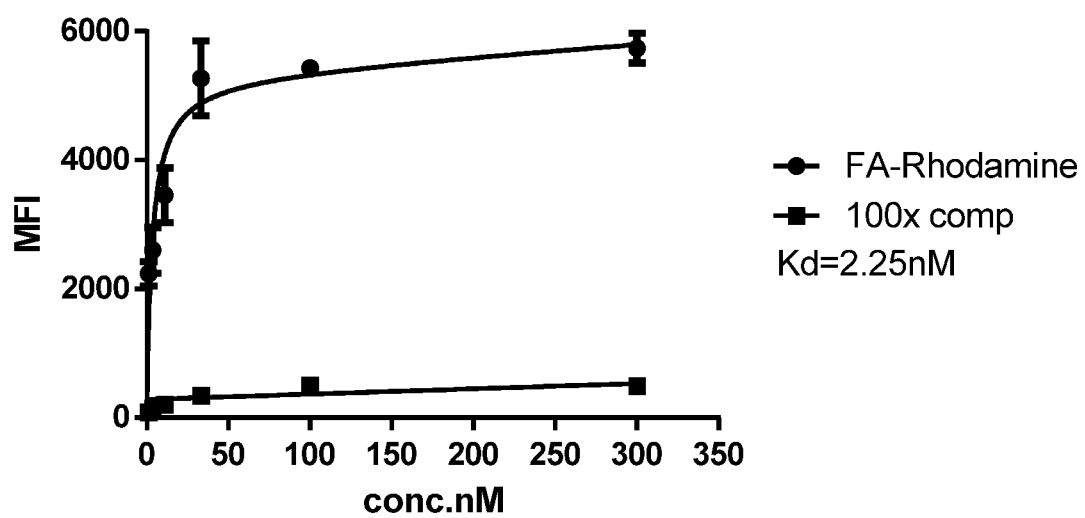
FIG. 12. FA-Rhodamine binding curve in 4M5.3FR fusion receptor. FA-Rhodamine can binds to 4M5.3FR fusion receptor that stably expressed on human T cell with high affinity (Kd=2.25 nM), which is comparable to the affinity of FA-Rhodamine in FR+KB cell (Kd around InM). Therefore, FR binding property is preserved in 4M5.3FR fusion receptor.

FA-Rhodamine can bind to 4M5.3FR fusion receptor that stably expressed on human T cell with high affinity (Kd=2.25 nM), which is comparable to the affinity of FA-Rhodamine in FR+KB cell (Kd around 1 nM). Therefore, FR binding property is preserved in 4M5.3FR fusion receptor. See FIG. 12.

2.8 FITC-AF647 Binding Curve in 4M5.3FR Fusion Receptor.

Figure 13:
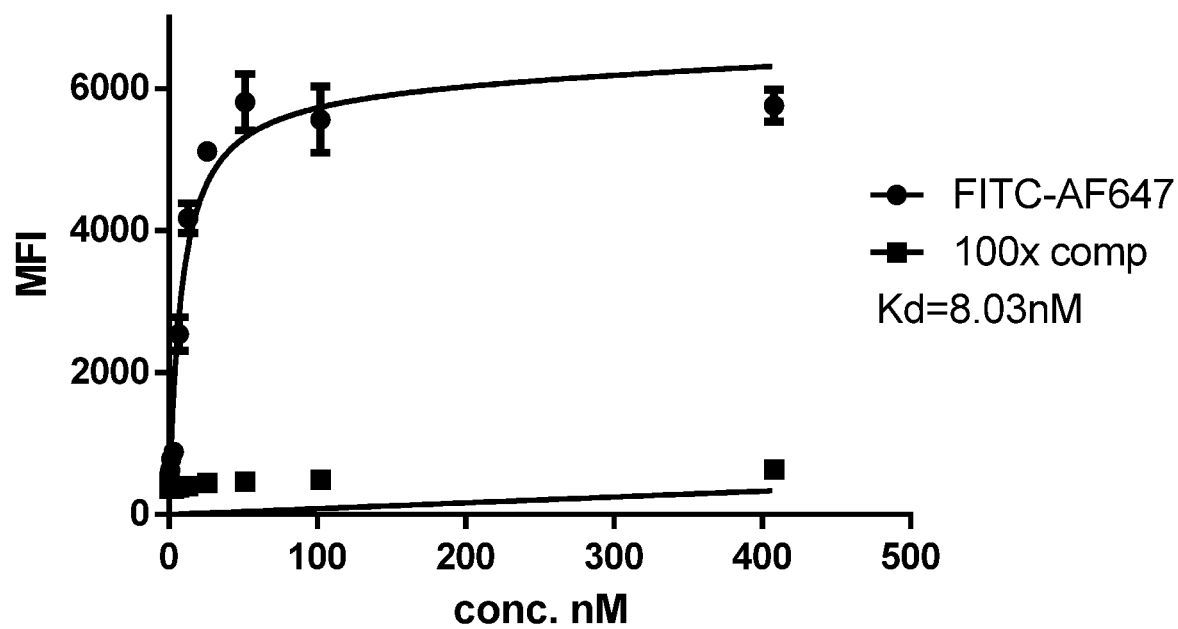
FIG. 13. FITC-AF647 binding curve in 4M5.3FR fusion receptor. FITC-AF647 can binds to 4M5.3FR fusion receptor that stably expression on human T cell with high affinity (Kd=8.03 nM). 100× comp indicates free FITC sodium. The binding property of scFv 4M5.3 with FITC is preserved in 4M5.3FR fusion receptor.

FITC-AF647 can bind to 4M5.3FR fusion receptor that stably expression on human T cell with high affinity (Kd=8.03 nM). 100× comp indicates free FITC sodium. The binding property of scFv 4M5.3 with FITC is preserved in 4M5.3FR fusion receptor. See FIG. 13.

3.1. FA-Tubulysin Killing Effect Against FF3+ Human T Cell

Figure 14:
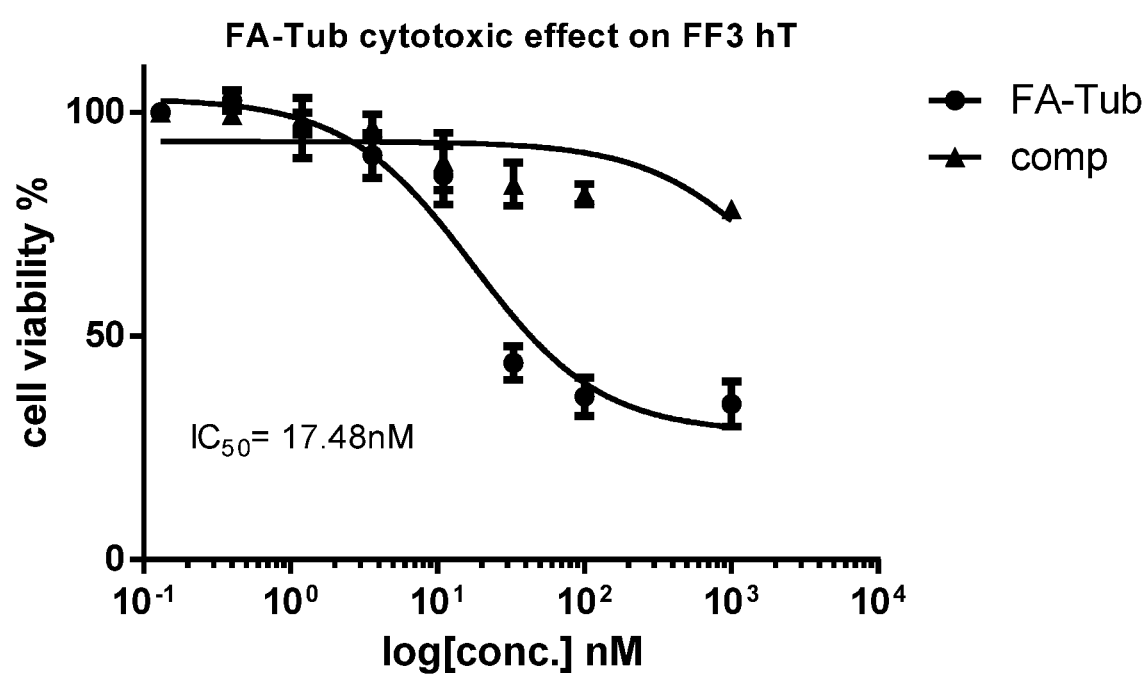
FIG. 14. FA-Tubulysin is able to mediate a receptor specific killing effect against FF3+ human T cell. Compensation with FA (100× preincubation with FA) blocks the effect. This implies the successful internalization and release of the free drug Tubulysin through the FF3 fusion receptor system.

FA-Tubulysin is able to mediate a receptor specific killing effect against FF3+ human T cell. Compensation with FA (100× preincubation with FA) blocks the effect. This implies the successful internalization and release of the free drug Tubulysin through the FF3 fusion receptor system. See FIG. 14.

3.2 FA-Tubulysin Killing Effect Against hFF3+ Population in a Mixed Human T Cell Culture.

Figure 15:
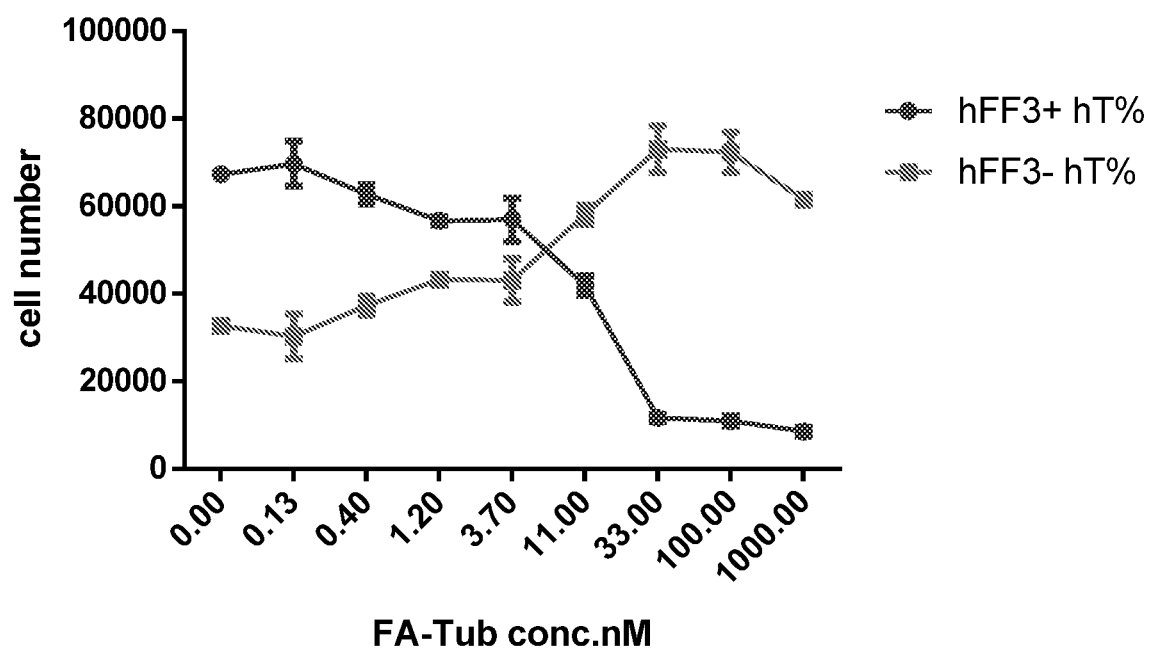
FIG. 15. FA-Tubulysin specifically kill the hFF3+ population in a mixed human T cell culture. Absolute number of hFF3+ cell decrease as the FA-Tub concentration increases, while hFF3-cells are killed also through released drugs and bystander effect at high concentration.

FA-Tubulysin specifically kills the hFF3+ population in a mixed human T cell culture. Percentage of hFF3+ cell decrease as the FA-Tub concentration increases. See FIG. 15.

3.3 SLF-Tub Specifically Kill the hFF3+ Jurkat Cells with a $IC_{50}$=138 nM.

Figure 16:
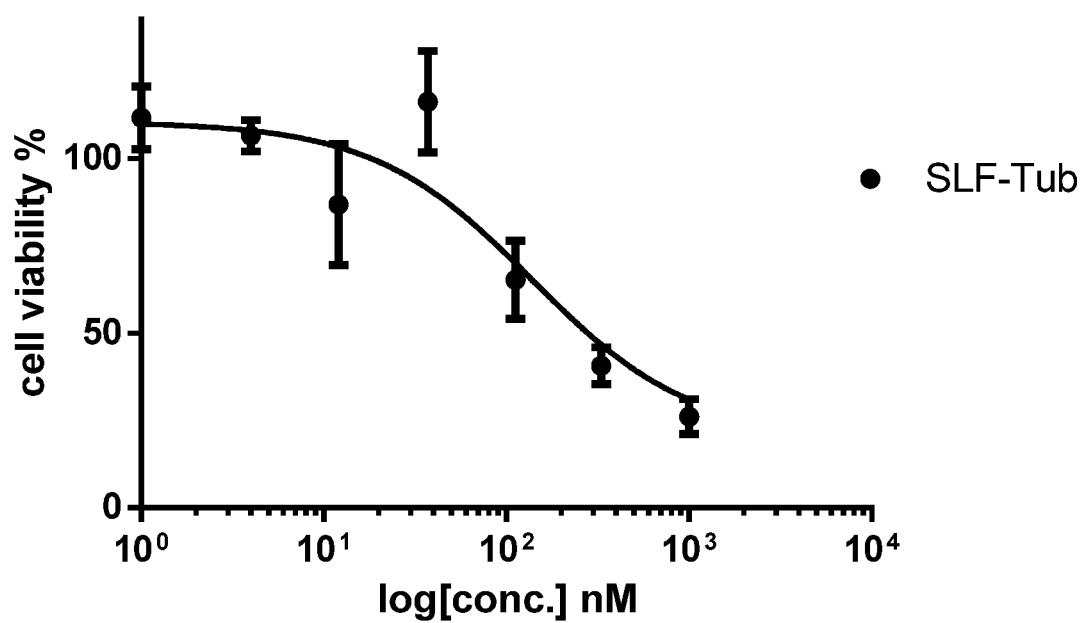
FIG. 16. SLF-Tub specifically kill the hFF3+ Jurkat cells with a $IC_{50}$=138 nM. This indicates the successful internalization of SLF-Tub by the FKBPFR3GS fusion receptor and the release of the Tubulysin inside the cell.

2 h incubation of SLF-Tub with hFF3 Jurkat cells is able to kill the receptor positive cells. This indicates the successful internalization of SLF-Tub by the FKBPFR3GS fusion receptor and the release of the Tubulysin inside the cell. See FIG. 16.

3.4. FITC-DM4 and FITC-Tub Killing Effects Against 4M5.3FR+ Human T cells

Figure 17:
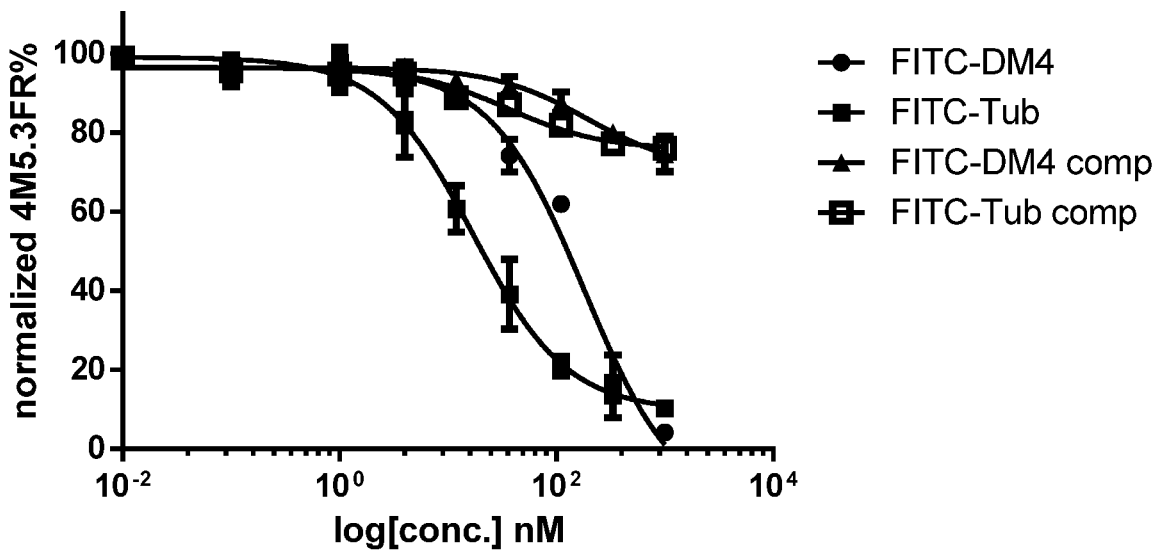
FIG. 17. Both FITC-DM4 and FITC-Tub can specifically kill the 4M5.3FR+ human T cells, while FITC-Tub has a higher $IC_{50}$. Compensation of free FITC sodium (100× preincubation) blocks the receptor mediated killing effect. This implies the successful internalization and release of FITC-cytotoxic drug into T cell through 4M5.3FR fusion receptor.

Both FITC-DM4 and FITC-Tub can specifically kill the 4M5.3FR+ human T cells, while FITC-Tub has a higher $IC_{50}$. Compensation of free FITC sodium (100× preincubation) blocks the receptor mediated killing effect. This implies the successful internalization and release of FITC-cytotoxic drug into T cell through 4M5.3FR fusion receptor. See FIG. 17.

3.5. FITC-Tubulysin Specifically Kill the 4M5.3FR+ Population in a Mixed Human T Cell Culture.

Figure 18:
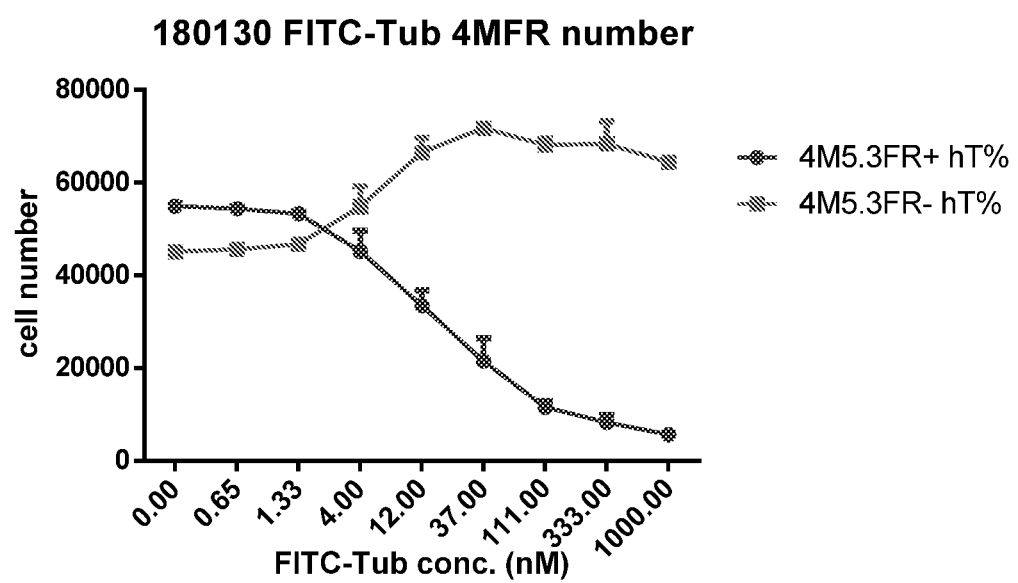
FIG. 18 FITC-Tubulysin specifically kill the 4M5.3FR+ population in a mixed human T cell culture. Absolute number of 4M5.3FR+ cell decrease as the FITC-Tub concentration increases, while the 4M5.3FR-cells are killed also through released drugs and bystander effect at high concentration.

Absolute number of 4M5.3FR+ cell decrease as the FITC-Tub concentration increases, while 4M5.3FR-cells are killed also through released drugs and bystander effect at high concentration. See FIG. 18.

3.6. FITC-DM4 Specifically Kill the 4M5.3FR+ Population in a Mixed Human T Cell Culture.

Figure 19:
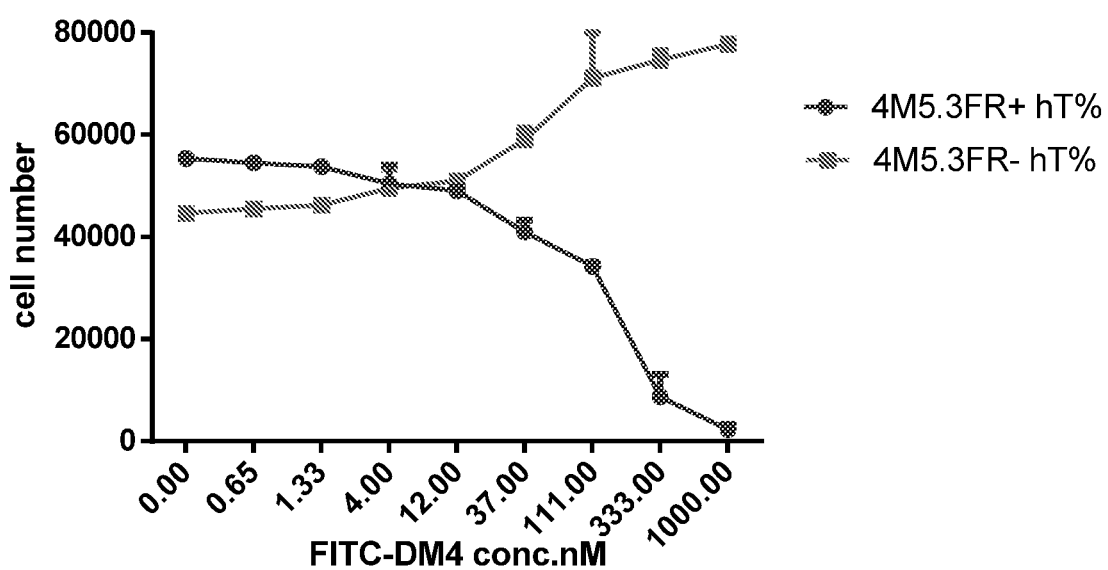
FIG. 19 FITC-DM4 specifically kill the 4M5.3FR+ population in a mixed human T cell culture. Absolute number of 4M5.3FR+ cell decrease as the FITC-DM4 concentration increases, while the 4M5.3FR-cells are killed also through released drugs and bystander effect at high concentration.

Absolute number of 4M5.3FR+ cell decrease as the FITC-DM4 concentration increases, while 4M5.3FR-cells are killed also through released drugs and bystander effect at high concentration. See FIG. 19.

Figure 20:
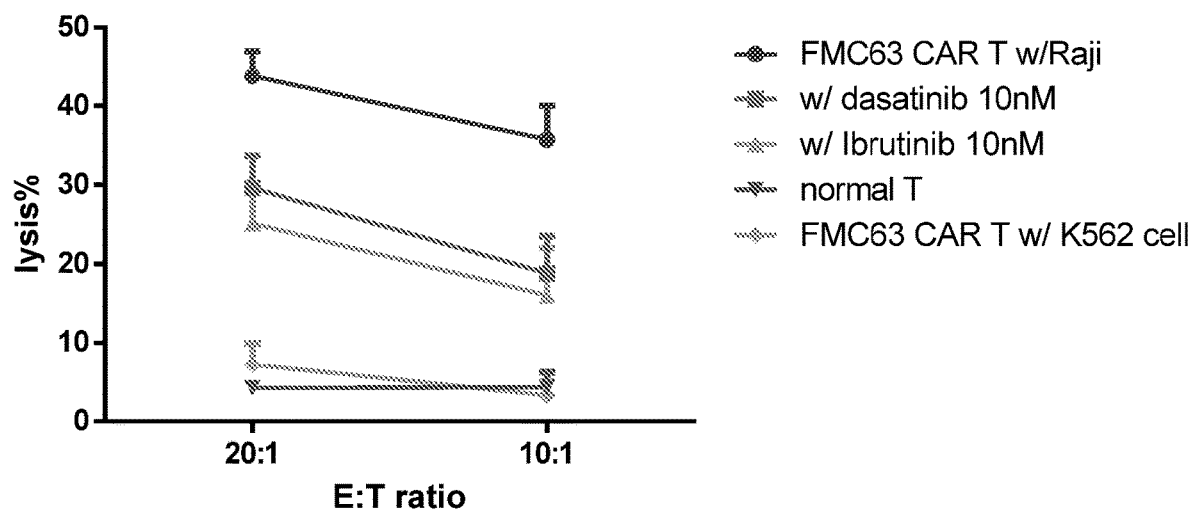
FIG. 20. Dasatinib (Lck inhibitor) and Ibrutinib (ITK inhibitor) at 10 nM concentration decrease the lysis effect of antiCD19 CAR T cell (FMC63 CAR T, Effector) against CD19+ Raji tumor cell (Target). Two Effector: Target ratio (E:T) have been tested. Normal T cell and antiCD19 CAR T with CD19-K562 cell were used as negative control.

3.7 Kinase Inhibitors Modulation Effect on Anti CD19 CAR T Cells Against CD19+Raji Dasatinib (Lck inhibitor) and Ibrutinib (ITK inhibitor) at 10 nM concentration decrease the lysis effect of antiCD19 CAR T cell (FMC63 CAR T, Effector) against CD 19+Raji tumor cell (Target). Two Effector:Target ratio (E:T) have been tested. Normal T cell and antiCD19 CAR T with CD19-K562 cell were used as negative control. See FIG. 20.

3.8. FITC-Dasatinib can Decrease the Lysis Effect of FMC63+4MFR+hT Cell Towards Raji Cell.

Figure 21:
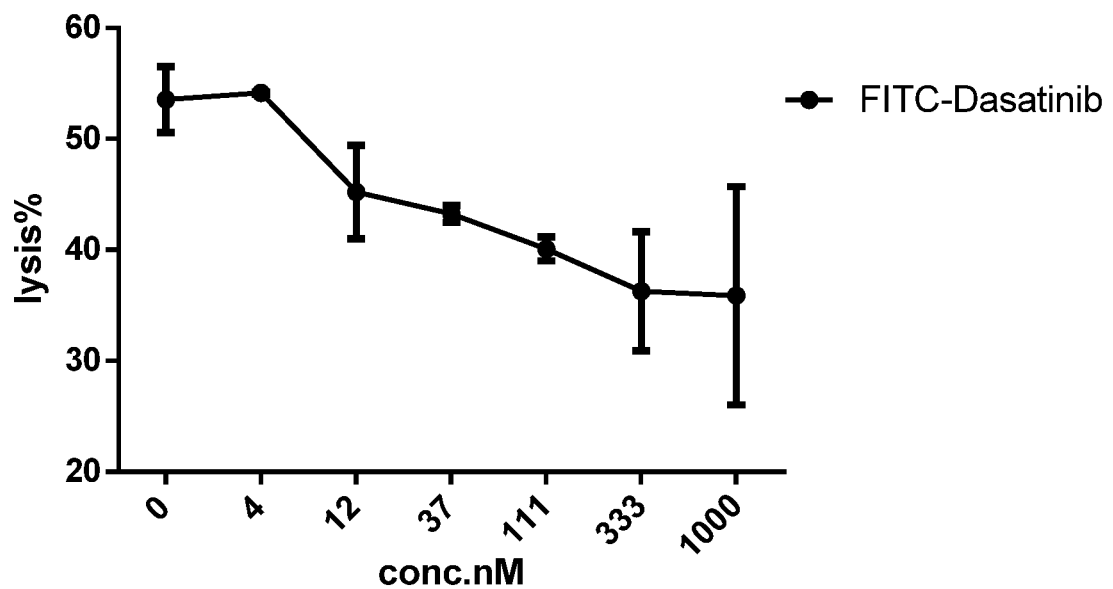
FIG. 21. FITC-Dasatinib can decrease the lysis effect of FMC63+4M5.3FR+hT cell towards Raji cell. This implies the successful internalization and release of FTTC-Dasatinib into T cell through 4M5.3FR fusion receptor and the release of Dasatinib into T cell.

This implies the successful internalization and release of FITC-Dasatinib into T cell through 4M5.3FR fusion receptor and the release of Dasatinib into T cell. See FIG. 21.

Figure 22:
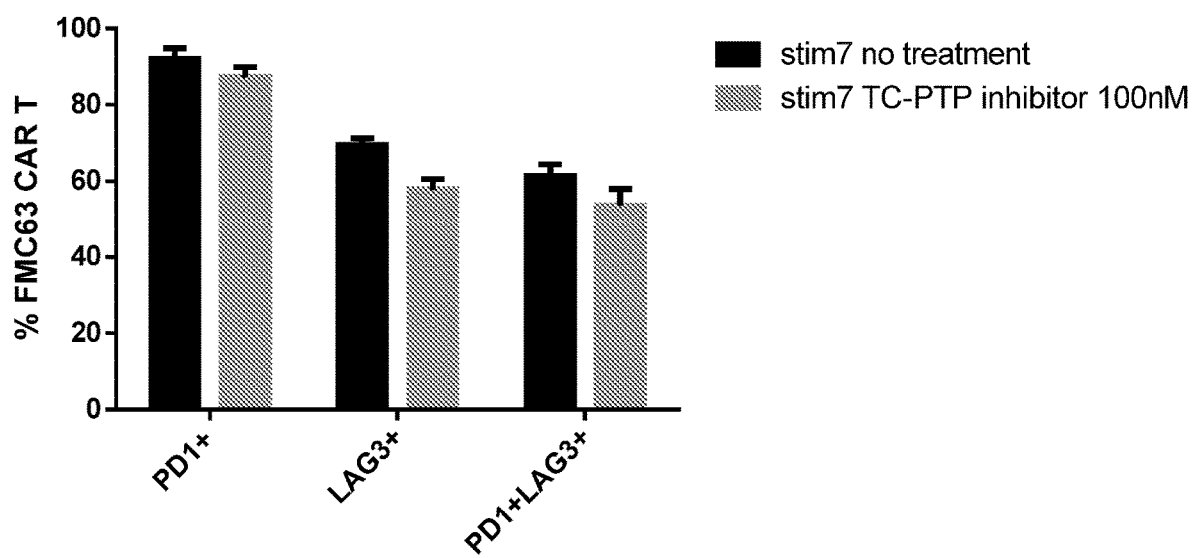
FIG. 22. TC-PTP inhibitor at 100 nM concentration decrease the co-inhibitor molecule population in exhausted antiCD19 CAR T cell (generated by 7 times of stimulation with CD19+Raji cells, see detailed procedure below). Both PD-1, LAG3 and double positive population decreases upon treatment. This implies that phosphatase inhibitors, like TC-PTP inhibitor may be used as a payload for the secret gateway platform for rejuvenating the exhausted CAR T cell.

3.9 TC-PTP Inhibitor at 100 nM Concentration Decrease the Co-Inhibitor Molecule Population in Exhausted antiCD19 CAR T Cell Exhausted antiCD19 CAR T cells are generated by 7 times of stimulation with CD19+Raji cells, see detailed procedure in material and methods section). PD-1 positive, LAG3 positive and double positive population decreases upon treatment. See FIG. 22.

4. Other FK506-Payload to Control the Activity of Cell Therapy

The technical advantageous feature of this drug payload delivery system is to have multi-functionality. The potential payloads and corresponding effects are listed below (Table 1). The small molecule payloads are selected based on the following parameters: 1. the functionality assay of the free drug, both in vitro and in vivo, has been confirmed by either published literature or work in our lab. 2. The chemical structure of the drug has relatively more accessible free amine for derivatization. 3. Any of the following will be preferable: FDA proved drug; commercially available for reasonable price. The FK506-payload will be tested first for in vitro experiments, T cell activation and stem cell cytokine release will be monitored by multiplex immunoassays. For in vivo disease models, we have well established CAR T therapy and bone fracture mouse models in our lab, and several potential collaborators for the neurodegenerative mouse models.

| Disease Model | Subtype | Cell Type | Cell source | Payload type |
| --- | --- | --- | --- | --- |
| stem cell therapy | HSC transplant | BMSC | Murine BM | GSK3b inhibitor |
| Tumor | tumor micro-environment | CAR T | hPBMCT cell | GSK3b inhibitor, HDAC inhibitor, MAPK inhibitor |

The invention claimed is:

1. A drug delivery platform for cell therapy comprising:
   an engineered protein on a target cell for transplant, wherein the engineered protein is selected from the group consisting of SEQ ID NOS: 1 and 2;
   a small molecule ligand conjugated to a linker, wherein the small molecule ligand has intrinsic high affinity to the engineered protein; and
   at least one payload of drug conjugated to the linker, wherein the at least one payload of drug is associated with the target cell when the small molecule ligand binds to the engineered protein.

2. The drug delivery platform according to claim 1, wherein the target cell for transplant is a CAR T cell expressing amino acid sequence selected from SEQ ID NOS: 3 and 4.

3. The drug delivery platform according to claim 1, wherein the small molecule ligand conjugate has the formula I

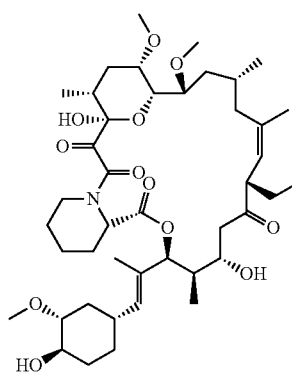
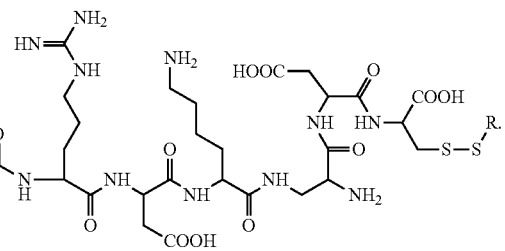

4. The drug delivery platform according to claim 1, wherein the target cell for transplant is a stem cell, a progenitor cell, an immune cell, a chimeric antigen receptor (CAR) T cell or a transplanted cell designed to synthesize a biochemical that is deficient in a patient.

5. The drug delivery platform according to claim 1, wherein the small molecule ligand is further conjugated to a fluorescent dye or radioactive probe.

6. The drug delivery platform according to claim 1, wherein the small molecule ligand is further conjugated to a regulator of endogenous gene expression.

7. The drug delivery platform according to claim 1, wherein the small molecule ligand is further conjugated to a regulator of a transduced transgene expression.

8. The drug delivery platform according to claim 1, wherein the at least one payload of drug is an imaging agent.

9. The drug delivery platform according to claim 8, wherein the imaging agent is selected from the group consisting of fluorescent dye rhodamine, fluorescein, and S0456.

10. The drug delivery platform according to claim 2, wherein imaging agent is selected from the group consisting of radioisotope chelating imaging moieties, EC 20 chelating head, NOTA and DOTA.

11. The drug delivery platform according to claim 1, wherein the at least one payload of drug is a cytotoxic drug.

12. The drug delivery platform according to claim 3, wherein the cytotoxic drug is selected from the group consisting of tubulysin, DM1, DM4, and an auristatin.

13. The drug delivery platform according to claim 1, wherein the at least one payload of drug is a modulator of gene expression.

14. The drug delivery platform according to claim 13, wherein the modulator is selected from the group consisting of Dasatinib, MEK1/2 inhibitor, and PI3K inhibitor.

15. The drug delivery platform according to claim 13, wherein the modulator is selected from the group consisting of HDAC inhibitor, kinase inhibitor and metabolic inhibitor.

16. The drug delivery platform according to claim 13, wherein the modulator is selected from the group consisting of GSK3 beta inhibitor, MAO-B inhibitor and Cdk5 inhibitor.

17. The drug delivery platform according to claim 13, wherein the modulator is an RORγt agonist.

18. The drug delivery platform according to claim 13, wherein the modulator is a siRNA.

19. The drug delivery platform according to claim 13, wherein the modulator is a phosphatase inhibitor.

20. The drug delivery platform according to claim 14, wherein the phosphatase inhibitor is against SHP1/2 or TC-PTP.

21. The drug delivery platform according to claim 1, wherein the at least one payload of drug is a modulator of the cell's activity.

22. The drug delivery platform according to claim 1, wherein the linker to connect the small molecule ligand and the at least one payload of drug is selected from the group consisting of:

153

-continued

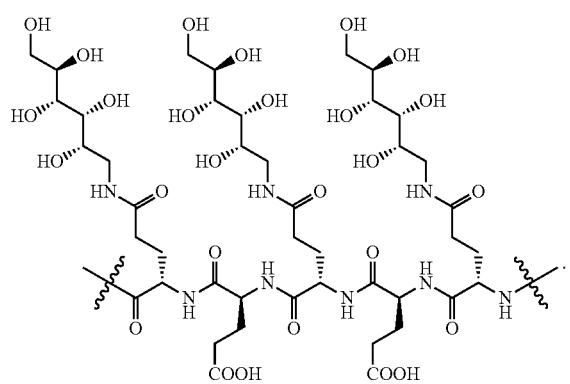

(SEQ ID NO: 22)

23. The drug delivery platform according to claim 1, wherein the small molecule ligand is selected from the group consisting of FK506, FK506 derivatives, synthetic ligand of FKBP (SLF), SLF derivatives, folic acid (FA), and FA derivatives.

24. The drug delivery platform according to claim 1, wherein the small molecule ligand is FK506 or its derivative.

25. A drug delivery platform for cell therapy comprising:
an engineered protein on a target cell for transplant, wherein the engineered protein is selected from the group consisting of SEQ ID NOS: 12, 13, 14, and 15;
a small molecule ligand conjugated to a linker, wherein the small molecule ligand has intrinsic high affinity to the engineered protein; and
at least one payload of drug conjugated to the linker, wherein the at least one payload of drug is associated with the target cell when the small molecule ligand binds to the engineered protein.

26. The drug delivery platform according to claim 25, wherein the at least one payload of drug is an imaging agent.

27. The drug delivery platform according to claim 26, wherein the imaging agent is selected from the group consisting of fluorescent dye rhodamine, fluorescein, and S0456.

28. The drug delivery platform according to claim 26, wherein imaging agent is selected from the group consisting of radioisotope chelating imaging moieties, EC 20 chelating head, NOTA and DOTA.

29. The drug delivery platform according to claim 25, wherein the at least one payload of drug is a cytotoxic drug.

30. The drug delivery platform according to claim 29, wherein the cytotoxic drug is selected from the group consisting of tubulysin, DM1, DM4, and an auristatin.

31. The drug delivery platform according to claim 25, wherein the at least one payload of drug is a modulator of gene expression.

32. The drug delivery platform according to claim 31, wherein the modulator is selected from the group consisting of Dasatinib, MEK1/2 inhibitor, and PI3K inhibitor.

33. The drug delivery platform according to claim 31, wherein the modulator is selected from the group consisting of HDAC inhibitor, kinase inhibitor and metabolic inhibitor.

34. The drug delivery platform according to claim 31, wherein the modulator is selected from the group consisting of GSK3 beta inhibitor, MAO-B inhibitor and Cdk5 inhibitor.

35. The drug delivery platform according to claim 31, wherein the modulator is an RORγt agonist.

154

36. The drug delivery platform according to claim 31, wherein the modulator is a siRNA.

37. The drug delivery platform according to claim 31, wherein the modulator is a phosphatase inhibitor.

38. The drug delivery platform according to claim 37, wherein the phosphatase inhibitor is against SHP1/2 or TC-PTP.

39. The drug delivery platform according to claim 25, wherein the at least one payload of drug is a modulator of the cell's activity.

40. The drug delivery platform according to claim 25, wherein the linker to connect the small molecule ligand and the at least one payload of drug is selected from the group consisting of (SEQ ID NO: 22)

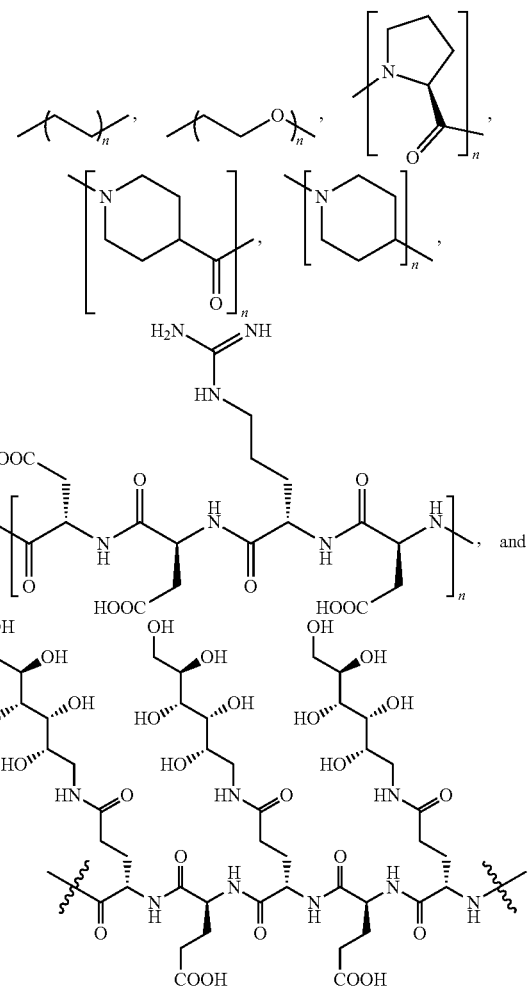

41. The drug delivery platform according to claim 25, wherein the small molecule ligand is selected from the group consisting of FK506, FK506 derivatives, synthetic ligand of FKBP (SLF), SLF derivatives, folic acid (FA), and FA derivatives.

42. The drug delivery platform according to claim 25, wherein the small molecule ligand is FK506 or its derivative.

43. The drug delivery platform according to claim 25, wherein the target cell for transplant is a CAR T cell expressing amino acid sequence selected from SEQ ID NOS: 3 and 4.

44. The drug delivery platform according to claim 25, wherein the small molecule ligand conjugate has formula I

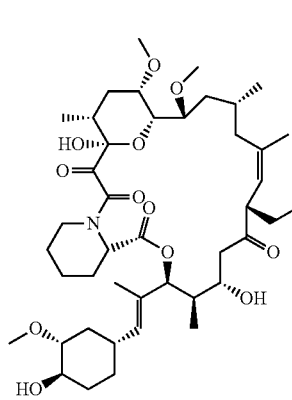
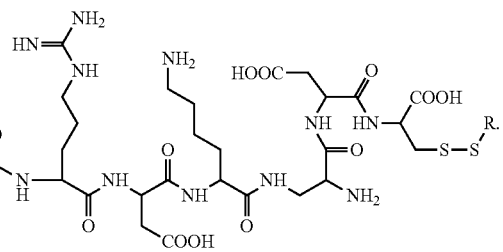

45. The drug delivery platform according to claim 25, wherein the target cell for transplant is a stem cell, a progenitor cell, an immune cell, a chimeric antigen receptor (CAR) T cell or a transplanted cell designed to synthesize a biochemical that is deficient in a patient.

46. The drug delivery platform according to claim 25, wherein the small molecule ligand is further conjugated to a fluorescent dye or radioactive probe.

47. The drug delivery platform according to claim 25, wherein the small molecule ligand is further conjugated to a regulator of endogenous gene expression.

48. The drug delivery platform according to claim 25, wherein the small molecule ligand is further conjugated to a regulator of a transduced transgene expression.

* * * * *

UNITED STATES PATENT AND TRADEMARK OFFICE
CERTIFICATE OF CORRECTION

PATENT NO. : 12,343,403 B2  
APPLICATION NO. : 16/486632  
DATED : July 1, 2025  
INVENTOR(S) : Low et al.

Page 1 of 1

It is certified that error appears in the above-identified patent and that said Letters Patent is hereby corrected as shown below:

In the Claims

In Column 151, Line 40, in Claim 10, delete "claim 2," and insert --claim 8,-- therefor In Column 151, Line 41, in Claim 10, after "wherein", insert --the--

In Column 151, Line 46, in Claim 12, delete "claim 3," and insert --claim 11,-- therefor In Column 152, Line 29, in Claim 20, delete "claim 14," and insert --claim 19,-- therefor In Column 154, Line 14, in Claim 40, after "of", insert --:--

Signed and Sealed this  
Twenty-seventh Day of January, 2026

John A. Squires  
*Director of the United States Patent and Trademark Office*